US012590312B2

(12) United States Patent
Schlabach et al.

(10) Patent No.: US 12,590,312 B2
(45) Date of Patent: Mar. 31, 2026

(54) NR4A SUPER-REPRESSORS AND METHODS OF USE THEREOF

(71) Applicant: KSQ Therapeutics, Inc., Cambridge, MA (US)

(72) Inventors: Michael Schlabach, Belmont, MA (US); Brian Alexander Sosa-Alvarado, Cambridge, MA (US)

(73) Assignee: KSQ Therapeutics, Inc., Cambridge, MA (US)

( * ) Notice: Subject to any disclaimer, the term of this patent is extended or adjusted under 35 U.S.C. 154(b) by 1089 days.

(21) Appl. No.: 17/612,934

(22) PCT Filed: May 21, 2020

(86) PCT No.: PCT/US2020/033980
§ 371 (c)(1),
(2) Date: Nov. 19, 2021

(87) PCT Pub. No.: WO2020/237040
PCT Pub. Date: Nov. 26, 2020

(65) Prior Publication Data
US 2022/0228155 A1     Jul. 21, 2022

Related U.S. Application Data

(60) Provisional application No. 62/851,554, filed on May 22, 2019.

(51) Int. Cl.

| | |
|---|---|
| *C12N 15/63* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/725* | (2006.01) |

(52) U.S. Cl.
CPC ............ *C12N 15/635* (2013.01); *A61K 40/11* (2025.01); *A61K 40/31* (2025.01); *A61K 40/4242* (2025.01); *A61P 35/00* (2018.01); *C07K 14/7051* (2013.01); *A61K 2239/38* (2023.05); *C07K 2319/03* (2013.01); *C07K 2319/40* (2013.01)

(58) Field of Classification Search
None
See application file for complete search history.

(56) References Cited

U.S. PATENT DOCUMENTS

| | | | | |
|---|---|---|---|---|
| 5,981,829 | A | 11/1999 | Mountz et al. | |
| 11,608,500 | B2 * | 3/2023 | Benson .............. | C07K 14/4705 |
| 2006/0040298 | A1 | 2/2006 | Schmidt et al. | |
| 2006/0063727 | A1 | 3/2006 | Chang | |
| 2019/0284553 | A1 * | 9/2019 | Benson ................... | A61P 35/04 |
| 2022/0228155 | A1 * | 7/2022 | Schlabach .......... | A61K 40/4242 |

FOREIGN PATENT DOCUMENTS

| | | |
|---|---|---|
| KR | 20150084469 A | 7/2015 |
| WO | WO-2005017112 A2 | 2/2005 |
| WO | WO-2019104245 A1 | 5/2019 |

OTHER PUBLICATIONS

Achatz, G., et al., "Functional Domains of the Human Orphan Receptor ARP-1/COUP-TFII Involved in Active Repression and Transrepression," Molecular and Cellular Biology 17(9):4914-4932, Taylor & Francis, United States (Sep. 1997).

Beerli, R.R., and Barbas, C.F., "Engineering Polydactyl Zinc-finger Transcription Factors," Nature Biotechnology 20(2):135-141, Nature America Publishing, United States (Feb. 2002).

Brudno, J.N., and Kochenderfer, J.N., "Chimeric Antigen Receptor T-cell Therapies for Lymphoma," Nature Reviews Clinical Oncology 15(1):31-46, Nature Publishing Group, United Kingdom (Jan. 2018).

Chen, J., et al., "NR4A Transcription Factors Limit CAR T Cell Function in Solid Tumours," Nature 567(7749):530-534, Nature Publishing Group, United Kingdom (Feb. 2019).

Choo, Y., and Isalan, M., "Advances in Zinc Finger Engineering," Current Opinion in Structural Biology 10(4):411-416, Elsevier, Netherlands (Aug. 2000).

Choo, Y., et al., "In Vivo Repression by a Site-specific DNA-binding Protein Designed Against an Oncogenic Sequence," Nature 372(6507):642-645, Nature Publishing Group, United Kingdom (Dec. 1994).

Fu, Y., et al., "NR4A Orphan Nuclear Receptors Modulate Insulin Action and the Glucose Transport System: Potential Role in Insulin Resistance," The Journal of Biological Chemistry 282(43):31525-31533, Elsevier Inc. on behalf of American Society for Biochemistry and Molecular Biology, United States (Sep. 2007).

Gilbert, L.A., et al., "CRISPR-mediated Modular RNA-guided Regulation of Transcription in Eukaryotes," Cell 154(2):442-451, Cell Press, United States (Jul. 2013).

Isalan, M., et al., "A Rapid, Generally Applicable Method to Engineer Zinc Fingers Illustrated by Targeting the HIV-1 Promoter," Nature Biotechnology 19(7):656-660, Nature America Publishing, United States (Jul. 2001).

Johnson, L.A., et al., "Gene Therapy With Human and Mouse T-cell Receptors Mediates Cancer Regression and Targets Normal Tissues Expressing Cognate Antigen," Blood 114(3):535-546, Elsevier, Netherlands (Jul. 2009).

(Continued)

*Primary Examiner* — Blaine Lankford
(74) *Attorney, Agent, or Firm* — Sterne, Kessler, Goldstein & Fox P.L.L.C.

(57) ABSTRACT

The present disclosure provides super-repressors capable of inhibiting the transcription of NR4A1, NR4A2, and NR4A3 target genes. The super-repressors can be used to enhance the effector functions of immune cells, e.g., for adoptive cell therapy. Methods of treating disorders using the modified immune cells are also provided.

19 Claims, 7 Drawing Sheets
Specification includes a Sequence Listing.

(56)     References Cited

OTHER PUBLICATIONS

Kochenderfer, J.N., et al., "B-cell Depletion and Remissions of Malignancy Along With Cytokine-associated Toxicity in a Clinical Trial of Anti-CD19 Chimeric-antigen-receptor-transduced T Cells," Blood 119(12):2709-2720, Elsevier, Netherlands (Mar. 2012).

Lamers, C.H., et al., "Treatment of Metastatic Renal Cell Carcinoma With CAIX Car-engineered T Cells: Clinical Evaluation and Management of on-target Toxicity," Molecular Therapy 21(4):904-912, Cell Press, United States (Feb. 2013).

Nordzell, M., et al., "Defining an N-terminal Activation Domain of the Orphan Nuclear Receptor Nurr1," Biochemical and Biophysical Research Communications 313(1):205-211, Elsevier, Netherlands (Jan. 2004).

Pabo, C.O., et al., "Design and Selection of Novel $Cys_2His_2$ Zinc Finger Proteins," Annual Review of Biochemistry 70:313-340, Annual Reviews, United States (Jul. 2001).

Paulsen, R.F., et al., "Three Related Brain Nuclear Receptors, NGFI-B, Nurr1, and NOR-1, as Transcriptional Activators," Journal of Molecular Neuroscience 6(4):249-255, Humana Press, United States (Dec. 1995).

Philips, A., et al., "Novel Dimeric Nur77 Signaling Mechanism in Endocrine and Lymphoid Cells," Molecular and Cellular Biology 17(10):5946-5951, Taylor & Francis, United States (Oct. 1997).

Radvanyi, L.G., et al., "Specific Lymphocyte Subsets Predict Response to Adoptive Cell Therapy Using Expanded Autologous Tumor-infiltrating Lymphocytes in Metastatic Melanoma Patients," Clinical Cancer Research 18(24):6758-6770, American Association for Cancer Research, United States (Dec. 2012).

Safe, S., et al., "Nuclear Receptor 4A (NR4A) Family—Orphans No More," The Journal of Steroid Biochemistry and Molecular Biology 157:48-60, Pergamon, United Kingdom (Mar. 2016).

Segal, D.J., and Barbas 3rd, C.F., "Custom DNA-Binding Proteins Come of Age: Polydactyl Zinc-Finger Proteins," Current Opinion in Biotechnology 12(6):632-637, Elsevier, Netherlands (Dec. 2001).

Song, C-H., et al., "Testicular Steroidogenesis is Locally Regulated by Androgen via Suppression of Nur77," Biochemical and Biophysical Research Communications 422(2):327-332, Elsevier, Netherlands (Jun. 2012).

Thakore, P.I., et al., "Editing the Epigenome: Technologies for Programmable Transcription and Epigenetic Modulation," Nature Methods 13(2):127-137, Nature Publishing Group, United Kingdom (Feb. 2016).

UniProtKB, "NR4A2_Human," Accession No. P43354, accessed at https://www.uniprot.org/uniprotkb/P43354/entry, accessed on Mar. 25, 2025, 10 pages.

UniProtKB, "NR4A3_Human," Accession No. Q92570, accessed at https://www.uniprot.org/uniprotkb/Q92570/entry, accessed on Mar. 25, 2025, 12 pages.

UniProtKB, "NR4A1_Human," Accession No. P22736, accessed at https://www.uniprot.org/uniprotkb/P22736/entry, accessed on Mar. 25, 2025, 17 pages.

Warren, R.S., et al., "Clinical Studies of Regional and Systemic Gene Therapy with Autologous CC49-zeta Modified T Cells in Colorectal Cancer Metastatic to Liver," Cancer Gene Therapy 5:S1-S2, pp. 1-3, Springer Nature, Germany (1998).

Wilson, T.E., et al., "Participation of Non-zinc Finger Residues in DNA Binding by Two Nuclear Orphan Receptors," Science 256(5053):107-110, American Association for the Advancement of Science, United States (Apr. 1992).

Yeo, N.C., et al., "An Enhanced CRISPR Repressor for Targeted Mammalian Gene Regulation," Nature Methods 15(8):611-616, Nature Publishing Group, United Kingdom (Aug. 2018).

Nakagawara, K., "NR4A Ablation Improves Mitochondrial Fitness for Long Persistence in Human CAR-T Cells Against Solid Tumors," Journal for Immunotherapy of Cancer 12(8):e008665, pp. 1-16, BMJ Publishing Group Ltd., United Kingdom (Aug. 2024).

Srirat, T., et al., "NR4a1/2 Deletion Promotes Accumulation of TCF1+ Stem-like Precursors of Exhausted CD8+ T Cells in the Tumor Microenvironment," Cell Reports 43(3):113898, pp. 1-25, Cell Press, United States (Mar. 2024).

* cited by examiner

NCOR1 (Trunc):DBD:LBD

NBRE 8X

NurRE 5X

NR4A SUPER-REPRESSORS AND METHODS OF USE THEREOF

CROSS-REFERENCE TO RELATED APPLICATIONS

This application is a U.S. National Phase of International Application No. PCT/US2020/033980, filed on May 21, 2020, which claims the benefit of U.S. Provisional Patent Application No. 62/851,554, filed on May 22, 2019, each of which is incorporated herein by reference in its entirety.

REFERENCE TO SEQUENCE LISTING SUBMITTED ELECTRONICALLY

The content of the electronically submitted sequence listing in ASCII text file (Name: 4195_0100001_Seqlisting_ST25.txt; Size: 89,555 bytes; and Date of Creation: Nov. 16, 2021), filed with the application, is incorporated herein by reference in its entirety.

FIELD

The disclosure relates to repressors of nuclear receptor transcription factors NR4A1, NR4A2, and NR4A3 and uses thereof, e.g., to increase the efficacy of adoptive cell therapy.

BACKGROUND

Adoptive cell transfer utilizing genetically modified T cells, in particular CAR-T cells have entered clinical testing as therapeutics for solid and hematologic malignancies. Results to date have been mixed. In hematologic malignancies (especially lymphoma, CLL and ALL), the majority of patients in several Phase 1 and 2 trials exhibited at least a partial response, with some exhibiting complete responses (Kochenderfer et al., 2012 Blood 1 19, 2709-2720). In 2017, the FDA approved two CAR-T therapies, Kymriah™ and Yescarta™ both for the treatment of hematological cancers. However, in most tumor types (including melanoma, renal cell carcinoma and colorectal cancer), fewer responses have been observed (Johnson et al., 2009 Blood 1 14, 535-546; Lamers et al., 2013 Mol. Ther. 21, 904-912; Warren et al., 1998 Cancer Gene Ther. 5, S1-S2). Success has largely been limited to CAR-T cells approaches targeting hematological malignancies of the B cell lineage.

It has been reported that CAR-T cells enter a hyporesponsive state that decreases their effectiveness, and that CAR-T cells lacking nuclear receptor transcription factors NR4A1, NR4A2, and NR4A3 (triple knockouts) promote tumor regression and prolong the survival of tumor-bearing mice (Chen et al. Nature 567: 530-534 (2019)). However, knocking out three genes is technically challenging. As such, there is considerable room for improvement with adoptive cell therapies.

SUMMARY

The present invention provides repressors of nuclear receptor transcription factors NR4A1, NR4A2, and NR4A3. Such repressors are capable of decreasing the activity of all three NR4A transcription factors using a single element.

Provided herein are polynucleotides encoding polypeptides comprising a DNA-binding domain that specifically binds to the NBRE element, to the NurRE element, or to both the NBRE element and the NurRE element, wherein the polypeptide does not comprise a transcription activation domain.

Provided herein are also polynucleotides encoding polypeptides comprising a DNA-binding domain that specifically binds to the NBRE element, to the NurRE element, or to both the NBRE element and the NurRE element, wherein the polypeptide inhibits the activity of NR4A1, NR4A2, and NR4A3.

Provided herein are also polynucleotides encoding polypeptides comprising a DNA-binding domain that specifically binds to the NBRE element, to the NurRE element, or to both the NBRE element and the NurRE element, wherein the polypeptide is capable of inhibiting transcription of a gene operably associated with the NBRE element, the NurRE element, or both the NBRE element and the NurRE element.

In certain instances, the polypeptide does not comprise a transcription activation domain.

In certain instances, the DNA-binding domain is a polypeptide comprising the amino acid sequence of the DNA-binding domain of NR4A1, NR4A2, or NR4A3. In certain instances, the DNA-binding domain comprises the amino acid sequence of the DNA-binding domain of NR4A3. In certain instances, the DNA-binding domain is a polypeptide comprising an amino acid sequence that is at least 80%, at least 85%, at least 90%, at least 95%, at least 96%, at least 97%, at least 98%, or at least 99% identical to the amino acid sequence of the DNA-binding domain of NR4A1, NR4A2, or NR4A3. In certain instances, the DNA-binding domain is a polypeptide comprising the amino acid sequence of SEQ ID NO:4 or 5. In certain instances, the DNA-binding domain is a polypeptide comprising the amino acid sequence of SEQ ID NO:50 or 51. In certain instances, the DNA-binding domain is a polypeptide comprising the amino acid sequence of SEQ ID NO:52 or 53.

In certain instances, the DNA-binding domain comprises a TAL effector DNA binding domain. In certain instances, the DNA-binding domain comprises the amino acid sequence of SEQ ID NO:6, 7, 8, or 10.

In certain instances, the DNA-binding domain comprises a zinc finger. In certain instances, the zinc finger binds to a polynucleotide comprising the nucleic acid sequence of any one of SEQ ID NOs:44-47 or to a polynucleotide comprising GATATT (SEQ ID NO:48) and GCCAAT (SEQ ID NO:49), optionally wherein SEQ ID NO:48 is 5' to SEQ ID NO:49. In certain instances, the DNA-binding domain comprises the amino acid sequence of SEQ ID NO:11, 12, 13, or 14.

In certain instances, the DNA-binding domain comprises a DNA-binding domain from a meganuclease.

In certain instances, the polypeptide further comprises the amino acid sequence of the ligand-binding domain (LBD) of NR4A1, NR4A2, or NR4A3. In certain instances, the amino acid sequence of the LBD is C-terminal to the DNA-binding domain. In certain instances, the amino acid sequence of the LBD is N-terminal to the DNA-binding domain.

In certain instances, the polypeptide further comprises a Krdppel-associated box (KRAB) domain. In certain instances, the KRAB domain is C-terminal to the DNA-binding domain. In certain instances, the KRAB domain is N-terminal to the DNA-binding domain.

In certain instances, the polypeptide further comprises NCOR1 or a fragment thereof. In certain instances, NCOR1 or fragment thereof is C-terminal to the DNA-binding domain. In certain instances, the NCOR1 or fragment thereof is N-terminal to the DNA-binding domain.

In certain instances, the polypeptide further comprises a heterologous domain. In certain instances, the heterologous domain is a dimerization domain, a transcriptional repressor domain, or a chromatin compaction domain. In certain instances, the heterologous domain is C-terminal to the DNA-binding domain. In certain instances, the heterologous domain is N-terminal to the DNA-binding domain.

In certain instances, the polypeptide further comprises a linker. In certain instances, the linker is located between the DNA-binding domain and the LBD, the KRAB domain, the NCOR1 or fragment thereof, or heterologous domain. In certain instances, the linker comprises the amino acid sequence of any one of SEQ ID NOs:9 and 25-28.

In certain instances, the polypeptide comprises the amino acid sequence of any one of SEQ ID NOs:29-43.

Provided herein are also vectors comprising any polynucleotide provided herein. In certain instances, the vector is a retroviral vector. In certain instances, the retroviral vector is a lentiviral vector. In certain instances, the vector further comprises a polynucleotide encoding an engineered immune receptor.

Provided herein are also compositions comprising any polynucleotide or vector provided herein.

Provided herein are also compositions comprising any polynucleotide or vector provided herein, wherein the composition further comprises a vector comprising a polynucleotide encoding an engineered immune receptor.

In certain vectors or compositions provided herein, the engineered immune receptor is (a) a chimeric antigen receptor (CAR) comprising an antigen-binding domain, a transmembrane domain, and an intracellular signaling domain or (b) an engineered T cell receptor (TCR).

In certain vectors or compositions provided herein, the engineered immune receptor specifically binds to an antigen expressed on a target cell, wherein the antigen is a tumor-associated antigen.

Provided herein are also polypeptides encoded by any polynucleotide provided herein.

Provided herein are also cells comprising any polynucleotide, vector, composition, or polypeptide provided herein. In certain instances, the cell is an immune effector cell. In certain instances, the immune effector cell is a T cell, a natural killer (NK) cell, or an NKT cell. In certain instances, a polynucleotide, vector, composition, or polypeptide provided herein enhances an effector function of the cell. In certain instances, the effector function is selected from cell proliferation, cell viability, tumor infiltration, cytotoxicity, anti-tumor immune responses, and/or resistance to exhaustion.

In certain instances, the cell further comprises an engineered immune receptor. In certain instances, the engineered immune receptor is (a) a chimeric antigen receptor (CAR) comprising an antigen-binding domain, a transmembrane domain, and an intracellular signaling domain or (b) an engineered T cell receptor (TCR). In certain instances, the engineered immune receptor specifically binds to an antigen expressed on a target cell, wherein the antigen is a tumor-associated antigen.

Provided herein are also compositions comprising any cell provided herein. In certain instances, the composition is suitable for administration to a subject in need thereof. In certain instances, the composition comprises autologous cells derived from the subject in need thereof. In certain instances, the composition comprises allogeneic cells derived from a donor subject.

Provided herein are also methods of producing a modified immune effector cell comprising introducing any polynucleotide, vector, composition, or polypeptide provided herein into an immune effector cell. In certain instances, the cell is a tumor infiltration lymphocyte. In certain instances, the method further comprises introducing a polynucleotide sequence encoding an engineered immune receptor into the immune effector cell, optionally wherein the engineered immune receptor is selected from a CAR and a TCR. In certain instances, the polynucleotide, vector, composition, or polypeptide provided herein and/or the polynucleotide encoding the engineered immune receptor are introduced to the immune effector cell by transfection, transduction, electroporation, or physical disruption of the cell membrane by a microfluidics device.

Provided herein are also methods of producing a modified immune effector cell comprising: obtaining a population of immune effector cells; expanding the population of immune effector cells; and introducing any polynucleotide, vector, composition, or polypeptide provided herein into the population of immune effector cells.

Provided herein are also methods of producing a modified immune effector cell comprising: obtaining a population of immune effector cells; expanding the population of immune effector cells in a first round expansion and a second round of expansion; and introducing any polynucleotide, vector, composition, or polypeptide provided herein into the population of immune effector cells. In certain instances, the polynucleotide, vector, composition, or polypeptide provided herein is introduced to the population of immune effector cells prior to the first and second rounds of expansion. In certain instances, the polynucleotide, vector, composition, or polypeptide provided herein is introduced to the population of immune effector cells after the first round of expansion and prior to the second round of expansion. In certain instances, the polynucleotide, vector, composition, or polypeptide provided herein is introduced to the population of immune effector cells after the first and second rounds of expansion. In certain instances, the introduction enhances one or more effector functions. In certain instances, the one or more effector functions are selected from cell proliferation, cell viability, cytotoxicity, tumor infiltration, increased cytokine production, anti-tumor immune responses, and/or resistance to exhaustion.

Also provided herein are methods of treating a disease or disorder in a subject in need thereof comprising administering to the subject an effective amount of any cells provided herein or any composition provided herein. In certain instances, the disease or disorder is a cell proliferative disorder, an inflammatory disorder, or an infectious disease. In certain instances, the disease or disorder is a cancer or a viral infection. In certain instances, the cancer is selected from a leukemia, a lymphoma, or a solid tumor. In certain instances, the cells are autologous to the subject. In certain instances, the cells are allogenic to the subject.

Also provided herein are methods of treating a cancer in a subject in need thereof comprising administering to the subject an effective amount of any cell provided herein or any composition provided herein. In certain instances, the administration inhibits tumor regrowth and/or inhibits tumor metastasis.

5

6 lack at least the TAF domain. The NR4A super-repressor proteins may also contain additional non-NR4A domains such NCOR1, a fragment thereof, or a KRAB domain. (See Example 1.)

Figure 2:
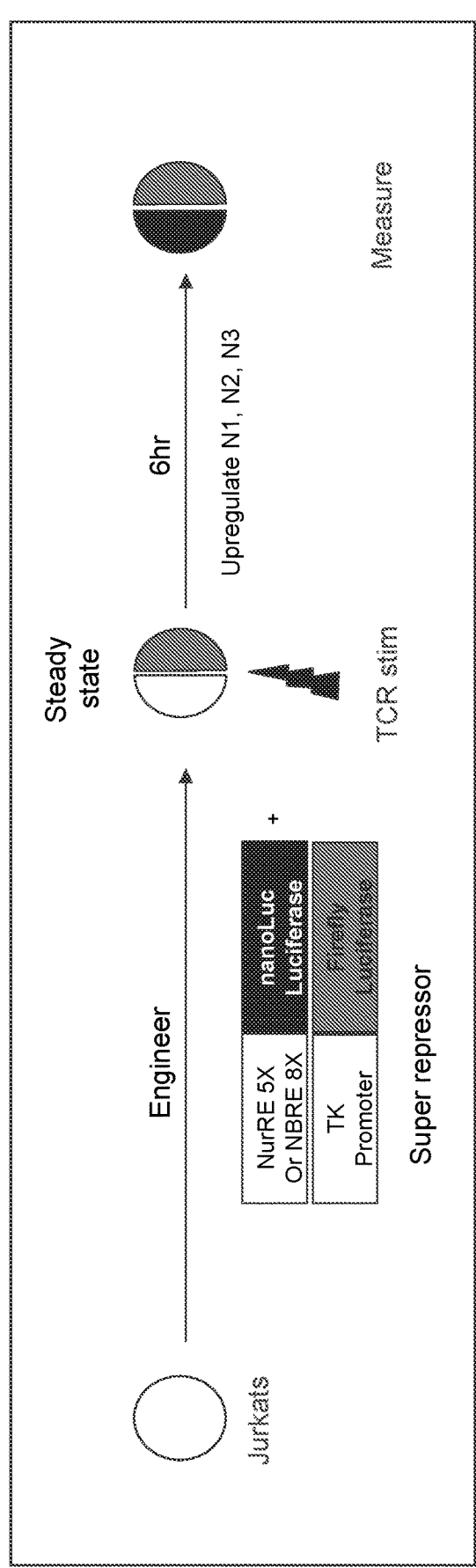

FIG. 2 shows a schematic of a super-repressor assay, which can be used to evaluate the ability of proteins to inhibit transcription of NR4A target genes. (See Example 2.)

Figure 3:
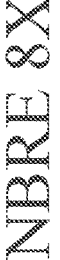
Figure 3:
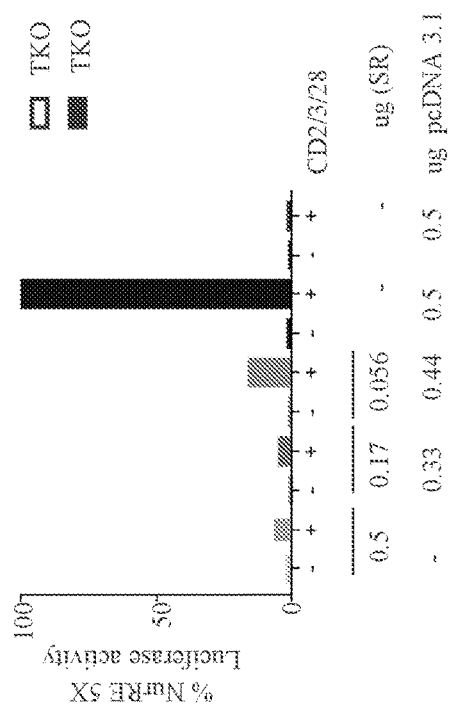
Figure 3:
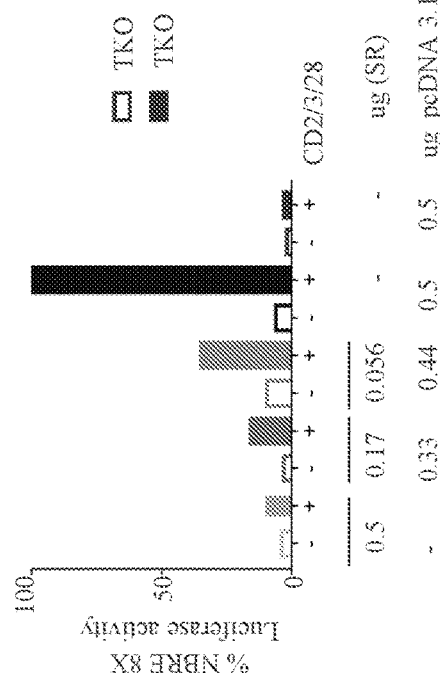

FIG. 3 shows the activity of the NR4A DBD domain in the super-repressor assay. In each graph, the two bars on the far right show the activity of the triple knock-out (TKO) in the absence (open bar; second bar from right) and presence (shaded bar; bar on far right) of T-cell activator stimulation. (See Example 2.)

Figure 4:
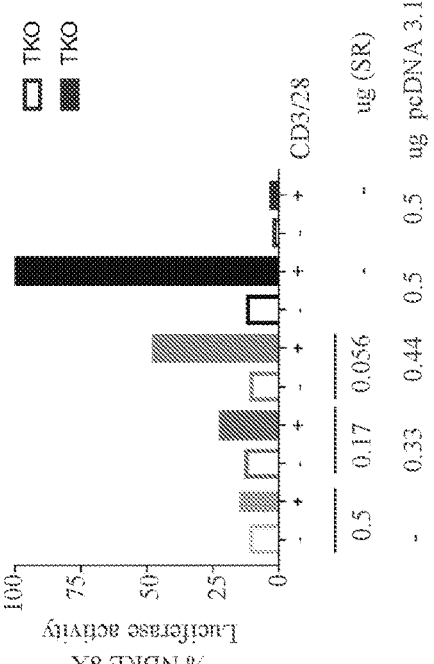

FIG. 4 shows the activity of the NR4A DBD and LBD domains in the super-repressor assay. In each graph, the two bars on the far right show the activity of the triple knock-out (TKO) in the absence (open bar; second bar from right) and presence (shaded bar; bar on far right) of T-cell activator stimulation. (See Example 2.)

Figure 5:
Figure 5:
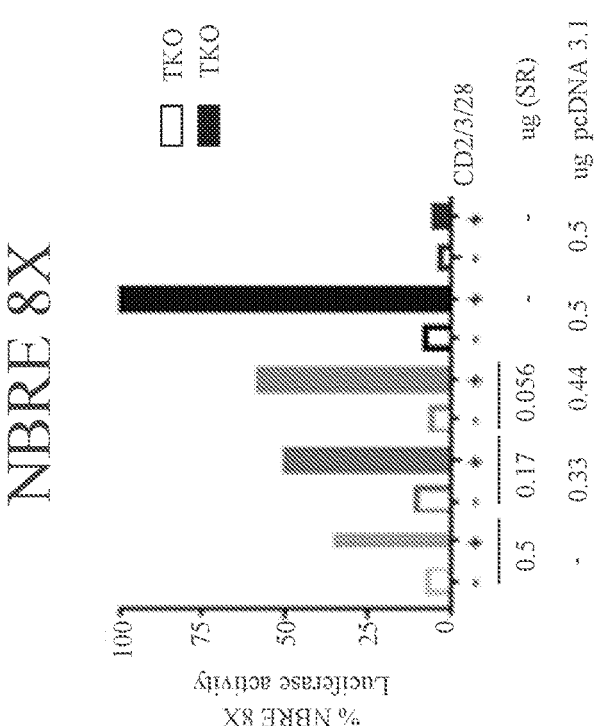

FIG. 5 shows the activity of a fusion protein comprising NCOR1 and the NR4A DBD and LBD domains in the super-repressor assay. In the graph, the two bars on the far right show the activity of the triple knock-out (TKO) in the absence (open bar; second bar from right) and presence (shaded bar; bar on far right) of T-cell activator stimulation. (See Example 2.)

Figure 6:
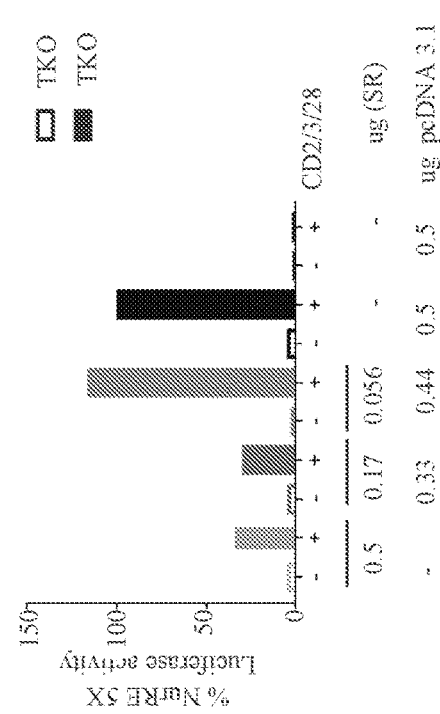
Figure 6:
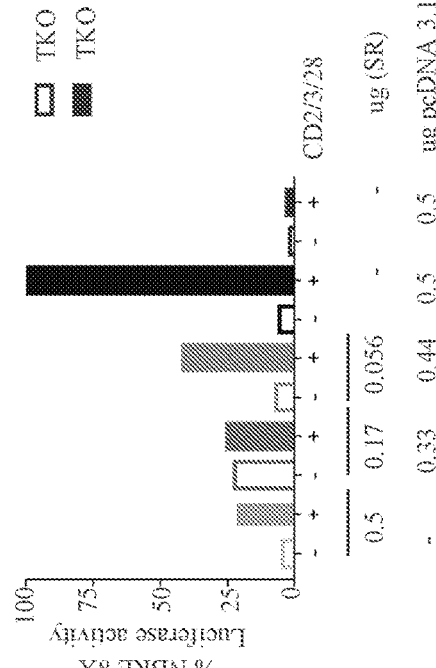
Figure 6:
Figure 6:

FIG. 6 shows the activity of a fusion protein comprising a truncated region of NCOR1 and the NR4A DBD and LBD domains in the super-repressor assay. In each graph, the two bars on the far right show the activity of the triple knock-out (TKO) in the absence (open bar; second bar from right) and presence (shaded bar; bar on far right) of T-cell activator stimulation. (See Example 2.)

Figure 7:
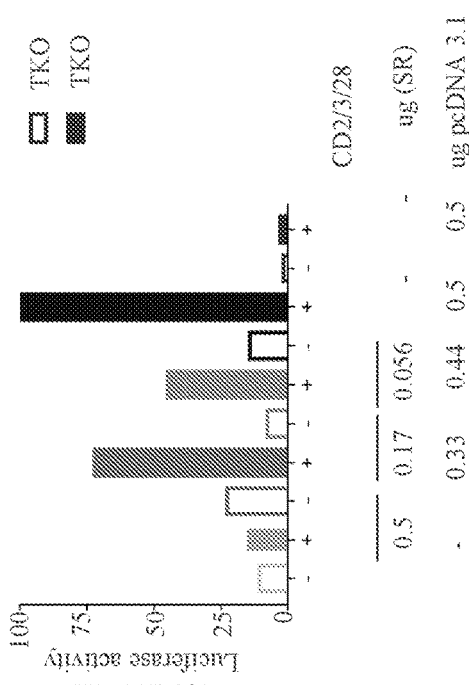

FIG. 7 shows the activity of a fusion protein comprising the NR4A DBD and KRAB in the super-repressor assay. In each graph, the two bars on the far right show the activity of the triple knock-out (TKO) in the absence (open bar) and presence (shaded bar; bar on far right) of T-cell activator stimulation. (See Example 2.)

DETAILED DESCRIPTION

Using genome-wide screens in CD8 T-cells, it was discovered that knocking out NR4A1, NR4A2, and NR4A3 can drive robust tumor killing effects. (See e.g., U.S. application Ser. No. 16/354,102 (US Application Publication No. US 2019/0284553), filed Mar. 14, 2019, which is herein incorporated by reference in its entirety.) However, the therapeutic use of knocking out three genes in a cell brings with it significant technical challenges. In order to avoid the technical challenges associated with knocking out three genes at once, the present disclosure provides super-repressors capable of inhibiting the transcription of NR4A1, NR4A2, and NR4A3 target genes. The super-repressors bind to the NBRE and/or NurRE response elements (e.g., via the DNA-binding domain of an NR4A transcription factor, a TAL effector (TALE), a zinc finger protein, or a guide RNA), but are not capable of activating transcription from these elements. Accordingly, the super-repressors inhibit the activity of NR4A1, NR4A2, and NR4A3. The present disclosure also provides polynucleotides encoding the super-repressors. As disclosed herein, the super-repressors and polynucleotides encoding the same can be used in adoptive cell therapy.

I. Definitions

As used herein, the singular forms "a," "an" and "the" include plural references unless the content clearly dictates otherwise.

As used herein, the term "and/or" means either "and" or "or" unless indicated otherwise.

As used herein, unless the context requires otherwise, the words "comprise", or variations such as "comprises" or "comprising", will be understood to imply the inclusion of a stated element or integer or group of elements or integers but not the exclusion of any other element or integer or group of elements or integers.

The term "nuclear receptor subfamily 4 group A member 1" or "NR4A1," as used herein refers to any native NR4A1 polypeptide or NR4A1-encoding polynucleotide. The term "NR4A1" encompasses "full-length," unprocessed NR4A1 polypeptide as well as any forms of NR4A1 that result from processing within the cell. The term also encompasses naturally occurring variants of NR4A1, e.g., those encoded by splice variants and allelic variants. The NR4A1 polypeptides described herein can be isolated from a variety of sources, such as from human tissue types or from another source, or prepared by recombinant or synthetic methods. Human NR4A1 sequences are known and include, for example, the sequences publicly available as UniProt No. P22736 (including isoforms). As used herein, the term "human NR4A1 protein" refers to NR4A1 protein comprising the amino acid sequence set forth in SEQ ID NO: 1.

```
                                        (SEQ ID NO: 1)
MPCIQAQYGTPAPSPGPRDHLASDPLTPEFIKPTMDLASPEAAPAAPTAL

PSFSTFMDGYTGEFDTFLYQLPGTVQPCSSASSSASSTSSSSATSPASAS

FKFEDFQVYGCYPGPLSGPVDEALSSSGSDYYGSPCSAPSPSTPSFQPPQ

LSPWDGSFGHFSPSQTYEGLRAWTEQLPKASGPPQPPAFFSFSPPTGPSP

SLAQSPLKLFPSQATHQLGEGESYSMPTAFPGLAPTSPHLEGSGILDTPV

TSTKARSGAPGGSEGRCAVCGDNASCQHYGVRTCEGCKGFFKRTVQKNAK

YICLANKDCPVDKRRRNRCQFCRFQKCLAVGMVKEVVRTDSLKGRRGRLP

SKPKQPPDASPANLLTSLVRAHLDSGPSTAKLDYSKFQELVLPHFGKEDA

GDVQQFYDLLSGSLEVIRKWAEKIPGFAELSPADQDLLLESAFLELFILR

LAYRSKPGEGKLIFCSGLVLHRLQCARGFGDWIDSILAFSRSLHSLLVDV

PAFACLSALVLITDRHGLQEPRRVEELQNRIASCLKEHVAAVAGEPQPAS

CLSRLLGKLPELRTLCTQGLQRIFYLKLEDLVPPPPIIDKIFMDTLPF
```

The two zinc fingers in the DNA binding domain (DBD) of SEQ ID NO:1 are amino acids 267-287 and 303-327, respectively. The DNA binding domain (DBD) of SEQ ID NO:1 is amino acids 264-339. The ligand binding domain (LBD) of SEQ ID NO:1 is amino acids 360-595.

The term "nuclear receptor subfamily 4 group A member 2" or "NR4A2," as used herein refers to any native NR4A2 polypeptide or NR4A2-encoding polynucleotide. The term "NR4A2" encompasses "full-length," unprocessed NR4A2 polypeptide as well as any forms of NR4A2 that result from processing within the cell. The term also encompasses naturally occurring variants of NR4A2, e.g., those encoded by splice variants and allelic variants. The NR4A2 polypeptides described herein can be isolated from a variety of sources, such as from human tissue types or from another source, or prepared by recombinant or synthetic methods. Human NR4A2 sequences are known and include, for example, the sequences publicly available as UniProt No. P43354 (including isoforms). As used herein, the term "human NR4A2 protein" refers to NR4A2 protein comprising the amino acid sequence set forth in SEQ ID NO:2.

(SEQ ID NO: 2)

```
MPCVQAQYGSSPQGASPASQSYSYHSSGEYSSDFLTPEFVKFSMDLTNTE

ITATTSLPSFSTFMDNYSTGYDVKPPCLYQMPLSGQQSSIKVEDIQMENY

QQHSHLPPQSEEMMPHSGSVYYKPSSPPTPTTPGFQVQHSPMWDDPGSLH

NFHQNYVATTHMIEQRKTPVSRLSLFSFKQSPPGTPVSSCQMRFDGPLHV

PMNPEPAGSHHVVDGQTFAVPNPIRKPASMGFPGLQIGHASQLLDTQVPS

PPSRGSPSNEGLCAVCGDNAACQHYGVRTCEGCKGFFKRTVQKNAKYVCL

ANKNCPVDKRRRNRCQYCRFQKCLAVGMVKEVVRTDSLKGRRGRLPSKPK

SPQEPSPPSPPVSLISALVRAHVDSNPAMTSLDYSRFQANPDYQMSGDDT

QHIQQFYDLLTGSMEIIRGWAEKIPGFADLPKADQDLLFESAFLELFVLR

LAYRSNPVEGKLIFCNGVVLHRLQCVRGFGEWIDSIVEFSSNLQNMNIDI

SAFSCIAALAMVTERHGLKEPKRVEELQNKIVNCLKDHVTFNNGGLNRPN

YLSKLLGKLPELRTLCTQGLQRIFYLKLEDLVPPPAIIDKLFLDTLPF
```

The two zinc fingers in the DNA binding domain (DBD) of SEQ ID NO:2 are amino acids 263-283 and 299-323, respectively. The DNA binding domain (DBD) of SEQ ID NO:2 is amino acids 260-335. The ligand binding domain (LBD) of SEQ ID NO:2 is amino acids 360-595.

The term "nuclear receptor subfamily 4 group A member 3" or "NR4A3," as used herein refers to any native NR4A3 polypeptide or NR4A3-encoding polynucleotide. The term "NR4A3" encompasses "full-length," unprocessed NR4A3 polypeptide as well as any forms of NR4A3 that result from processing within the cell. The term also encompasses naturally occurring variants of NR4A3, e.g., those encoded by splice variants and allelic variants. The NR4A3 polypeptides described herein can be isolated from a variety of sources, such as from human tissue types or from another source, or prepared by recombinant or synthetic methods. Human NR4A3 sequences are known and include, for example, the sequences publicly available as UniProt No. Q92570 (including isoforms). As used herein, the term "human NR4A3 protein" refers to NR4A3 protein comprising the amino acid sequence set forth in SEQ ID NO:3.

(SEQ ID NO: 3)

```
MPGVQAQYSPSPPGSSYAAQTYSSEYTTEIMNPDYTKLTMDLGSTEITAT

ATTSLPSISTFVEGYSSNYELKPSCVYQMQRPLIKVEEGRAPSYHHHHHH

HHHHHHHHQQQHQQPSIPPASSPEDEVLPSTSMYFKQSPPSTPTTPAFPP

QAGALWDEALPSAPGCIAPGPLLDPPMKAVPTVAGARFPLFHFKPSPPHP

PAPSPAGGHHLGYDPTAAAALSLPLGAAAAAGSQAAALESHPYGLPLAKR

AAPLAFPPLGLTPSPTASSLLGESPSLPSPPSRSSSSGEGTCAVCGDNAA

CQHYGVRTCEGCKGFFKRTVQKNAKYVCLANKNCPVDKRRRNRCQYCRFQ

KCLSVGMVKEVVRTDSLKGRRGRLPSKPKSPLQQEPSQPSPPSPPICMMN

ALVRALTDSTPRDLDYSRYCPTDQAAAGTDAEHVQQFYNLLTASIDVSRS

WAEKIPGFTDLPKEDQTLLIESAFLELFVLRLSIRSNTAEDKFVFCNGLV

LEIRLQCLRGFGEWLDSIKDFSLNLQSLNLDIQALACLSALSMITERHGL

KEPKRVEELCNKITSSLKDHQSKGQALEPTESKVLGALVELRKICTLGLQ

RIFYLKLEDLVSPPSIIDKLFLDTLPF
```

The two zinc fingers in the DNA binding domain (DBD) of SEQ ID NO:3 are amino acids 292-312 and 328-352, respectively. The DNA binding domain (DBD) of SEQ ID NO:3 is amino acids 289-364. The ligand binding domain (LBD) of SEQ ID NO:3 is amino acids 394-623.

The term "NR4A super-repressor" refers to an agent that binds to the NBRE and/or NurRE response elements and inhibits the transcriptional activity of NR4A1, NR4A2, and NR4A3.

As used herein, the terms "about" and "approximately" are used as equivalents. Any numerals used herein with or without about/approximately are meant to cover any normal fluctuations appreciated by one of ordinary skill in the relevant art. In certain embodiments, the term "approximately" or "about" refers to a range of values that fall within 10% (for example, 9%, 8%, 7%, 6%, 5%, 4%, 3%, 2%, or 1%) or less in either direction (greater than or less than) of the stated reference value unless otherwise stated or otherwise evident from the context (except where such number would exceed 100% of a possible value).

"Decrease" or "reduce" refers to a decrease or a reduction in a particular value of at least 5%, for example, a 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or 100% decrease as compared to a reference value.

"Increase" refers to an increase in a particular value of at least 5%, for example, a 5%, 6%, 7%, 8%, 9%, 1, 1%, 20%, 25%, 30%, 35%, 40%, 45%, 50%, 55%, 60%, 65%, 70%, 75%, 80%, 85%, 90%, 95%, 99%, 100%, 200%, 300%, 400%, 500%, or more increase as compared to a reference value.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

"Fragment" refers to a portion of a polypeptide or polynucleotide molecule containing less than the entire polypeptide or polynucleotide sequence. In some embodiments, a fragment of a polypeptide or polynucleotide comprises at least 10%, 20%, 30%, 40%, 50%, 60%, 70%, 80%, 90%, 95%, 96%, 97%, 98%, or 99% of the entire length of the reference polypeptide or polynucleotide. In some embodiments, a polypeptide or polynucleotide fragment may contain 5, 10, 15, 20, 25, 30, 35, 40, 45, 50, 60, 70, 80, 90, 100, 200, 300, 400, 500, 600, 700, 800, 900, 1000, or more nucleotides or amino acids.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared.

"Complementary" refers to the capacity for pairing, through base stacking and specific hydrogen bonding, between two sequences comprising naturally or non-naturally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a complementary nucleic acid) under the appropriate in vitro and/or in vivo conditions of temperature and solution ionic strength.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The term "modified" refers to a substance or compound (e.g., a cell, a polynucleotide sequence, and/or a polypeptide sequence) that has been altered or changed as compared to the corresponding unmodified substance or compound.

The term "naturally-occurring" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

"Isolated" refers to a material that is free to varying degrees from components which normally accompany it as found in its native state.

An "expression cassette" or "expression construct" refers to a DNA polynucleotide sequence operably linked to a promoter. "Operably linked" refers to a juxtaposition wherein the components so described are in a relationship permitting them to function in their intended manner. For instance, a promoter is operably linked to a polynucleotide sequence if the promoter affects the transcription or expression of the polynucleotide sequence.

The term "recombinant vector" as used herein refers to a polynucleotide molecule capable transferring or transporting another polynucleotide inserted into the vector. The inserted polynucleotide may be an expression cassette. In some embodiments, a recombinant vector may be viral vector or a non-viral vector (e.g., a plasmid).

The term "sample" refers to a biological composition (e.g., a cell or a portion of a tissue) that is subjected to analysis and/or genetic modification. In some embodiments, a sample is a "primary sample" in that it is obtained directly from a subject; in some embodiments, a "sample" is the result of processing of a primary sample, for example to remove certain components and/or to isolate or purify certain components of interest.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

"Administration" refers herein to introducing an agent or composition into a subject.

Administration "in combination with" one or more further therapeutic agents includes simultaneous (concurrent) or consecutive administration in any order.

"Treating" as used herein refers to delivering an agent or composition to a subject to affect a physiologic outcome.

As used herein, the term "effective amount" refers to at least the minimum amount of an agent or composition required to result in a particular physiological effect. The effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

"Population" of cells refers to any number of cells greater than 1, but is preferably at least $1\times10^3$ cells, at least $1\times10^4$ cells, at least at least $1\times10^5$ cells, at least $1\times10^6$ cells, at least $1\times10^7$ cells, at least $1\times10^8$ cells, at least $1\times10^9$ cells, at least $1\times10^{10}$ cells, or more cells. A population of cells may refer to an in vitro population (e.g., a population of cells in culture) or an in vivo population (e.g., a population of cells residing in a particular tissue).

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

II. NR4A Super-Repressors

NR4A super-repressors are molecules that bind to the NBRE and/or NurRE response elements but do not activate transcription and therefore inhibit the transcriptional activity of NR4A1, NR4A2, and NR4A3. As described in more detail herein, the super-repressors comprise a DNA-binding domain that binds to the NBRE and/or NurRE response elements and may also contain additional domains. The super-repressors do not contain a transcriptional activation domain.

A. DNA-Binding Domains of NR4A Super-Repressors

A DNA-binding domain that binds to NBRE and/or NurRE response elements can be any type of DNA-binding domain including, e.g., the DNA-binding domain of an NR4A transcription factor, a TAL effector (TALE), or a zinc finger protein.

The DNA-binding domain (DBD) can comprise the amino acid sequence of the DBD of NR4A1, NR4A2, or NR4A3. Thus, a DBD can comprise amino acids 264-339 of SEQ ID NO:1, amino acids 260-335 of SEQ ID NO:2, and/or amino acids 289-364 of SEQ ID NO:3.

Exemplary DBD sequences comprising the amino acid sequences of the DBD of NR4A1 are shown below as SEQ ID NOs: 50 and 51.

```
                                    (SEQ ID NO: 50)
SEGRCAVCGDNASCQHYGVRTCEGCKGFFKRTVQKNAKYICLANKDCPVD

KRRRNRCQFCRFQKCLAVGMVKEVVRTDSLKGRRGRLPSKPK (SEQ ID NO: 51)
SEGRCAVCGDNASCQHYGVRTCEGCKGFFKRTVQKNAKYICLANKDCPVD

KRRRNRCQFCRFQKCLAVGMVKEVVRTDSLKGRRGRLPSKPKQ
```

Exemplary DBD sequences comprising the amino acid sequences of the DBD of NR4A2 are shown below as SEQ ID NOs: 52 and 53.

```
                                    (SEQ ID NO: 52)
NEGLCAVCGDNAACQHYGVRTCEGCKGFFKRTVQKNAKYVCLANKNCPV
DKRRRNRCQYCRFQKCLAVGMVKEVVRTDSLKGRRGRLPSKPK (SEQ ID NO:53)
NEGLCAVCGDNAACQHYGVRTCEGCKGFFKRTVQKNAKYVCLANKNCPV
DKRRRNRCQYCRFQKCLAVGMVKEVVRTDSLKGRRGRLPSKPKS
```

Exemplary DBD sequences comprising the amino acid sequence of the DBD of NR4A3 are shown below as SEQ ID NO:4 and SEQ ID NO:5.

```
                                    (SEQ ID NO: 4)
GEGTCAVCGDNAACQHYGVRTCEGCKGFFKRTVQKNAKYVCLANKNCPV
DKRRRNRCQYCRFQKCLSVGMVKEVVRTDSLKGRRGRLPSKPK (SEQ ID NO: 5)
GEGTCAVCGDNAACQHYGVRTCEGCKGFFKRTVQKNAKYVCLANKNCPV
DKRRRNRCQYCRFQKCLSVGMVKEVVRTDSLKGRRGRLPSKPKS
```

The DNA-binding domain (DBD) can comprise a TAL. TAL effectors are proteins that are secreted by *Xanthomonas* bacteria via their type III secretion system when they infect plants. The DNA binding domain contains a repeated, highly conserved, 33-34 amino acid sequence with divergent 12th and 13th amino acids. These two positions, referred to as the Repeat Variable Diresidue (RVD), are highly variable and strongly correlated with specific nucleotide recognition. Therefore, the TAL effector domains can be engineered to bind specific target DNA sequences by selecting a combination of repeat segments containing the appropriate RVDs. The nucleic acid specificity for RVD combinations is as follows: HD targets cytosine, NI targets adenenine, NG targets thymine, and NN targets guanine (though, in some embodiments, NN can also bind adenenine with lower specificity).

As provided herein, a TAL can bind to NBRE and/or NurE.

A DBD comprising a TAL that is capable of binding NBRE can comprise e.g., the amino acid sequence of SEQ ID NO:6.

```
                                    (SEQ ID NO: 6)
MLTPEQVVAIASNHGGKQALETVQRLLPVCQAHGLTPEQVVAIASNIGG

KQALETVQRLLPVCQAHGLTPEQVVAIASNGGGKQALETVQRLLPVCQA

HGLTPEQVVAIASNIGGKQALETVQRLLPVCQAHGLTPEQVVAIASNGG

GKQALETVQRLLPVCQAHGLTPEQVVAIASNGGGKQALETVQRLLPVCQ

AHGLTPEQVVAIASNGGGKQALETVQRLLPVCQAHG
```

A DBD comprising a TAL that is capable of binding NurE, can comprise e.g., the amino acid sequences of SEQ ID NO:7 and/or 8.

```
                                    (SEQ ID NO: 7)
MLTPEQVVAIASNHGGKQALETVQRLLPVCQAHGLTPEQVVAIASNIGG

KQALETVQRLLPVCQAHGLTPEQVVAIASNGGGKQALETVQRLLPVCQA

HGLTPEQVVAIASNIGGKQALETVQRLLPVCQAHGLTPEQVVAIASNGG

GKQALETVQRLLPVCQAHGLTPEQVVAIASNGGGKQALETVQRLLPVCQ

AHGLTPEQVVAIASNGGGKQALETVQRLLPVCQAHG (SEQ ID NO: 8)
LTPEQVVAIASNIGGKQALETVQRLLPVCQAHGLTPEQVVAIASNIGGK

QALETVQRLLPVCQAHGLTPEQVVAIASNIGGKQALETVQRLLPVCQAH

GLTPEQVVAIASNGGGKQALETVQRLLPVCQAHGLTPEQVVAIASNHGG

KQALETVQRLLPVCQAHGLTPEQVVAIASHDGGKQALETVQRLLPVCQA

HGLTPEQVVAIASHDGGKQALETVQRLLPVCQAHG
```

In a TAL comprising the amino acid sequences of SEQ ID NO:7 and 8, the amino acid sequences of SEQ ID NO:7 and SEQ ID NO:8 can be connected by a linker. The linker can comprise the amino acid sequence of GGSGNGEGSGNG (SEQ ID NO:9). Accordingly, a TAL that is capable of binding to NurE can comprise the amino acid sequence of SEQ ID NO: 10.

```
                                          (SEQ ID NO: 10)
MLTPEQVVAIASNHGGKQALETVQRLLPVCQAHGLTPEQVVAIASNIGG

KQALETVQRLLPVCQAHGLTPEQVVAIASNGGGKQALETVQRLLPVCQA

HGLTPEQVVAIASNIGGKQALETVQRLLPVCQAHGLTPEQVVAIASNGG

GKQALETVQRLLPVCQAHGLTPEQVVAIASNGGGKQALETVQRLLPVCQ

AHGLTPEQVVAIASNGGGKQALETVQRLLPVCQAHGGGSGNGEGSGNGL

TPEQVVAIASNIGGKQALETVQRLLPVCQAHGLTPEQVVAIASNIGGKQ

ALETVQRLLPVCQAHGLTPEQVVAIASNIGGKQALETVQRLLPVCQAHG

LTPEQVVAIASNGGGKQALETVQRLLPVCQAHGLTPEQVVAIASNHGGK

QALETVQRLLPVCQAHGLTPEQVVAIASHDGGKQALETVQRLLPVCQAH

GLTPEQVVAIASHDGGKQALETVQRLLPVCQAHG
```

The DNA-binding domain (DBD) can comprise a zinc finger protein. A "zinc finger DNA binding domain," "zinc finger protein," or "ZFP" is a protein, or a domain within a larger protein, that binds DNA in a sequence-specific manner through one or more zinc fingers, which are regions of amino acid sequence within the binding domain whose structure is stabilized through coordination of a zinc ion. Typically, a single zinc finger domain is about 30 amino acids in length. An individual zinc finger binds to a three-nucleotide (i.e., triplet) sequence (or a four-nucleotide sequence which can overlap, by one nucleotide, with the four-nucleotide binding site of an adjacent zinc finger). Therefore the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. Binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain. In some embodiments, the DNA-binding domains of individual ZFNs comprise between three and six individual zinc finger repeats and can each recognize between 9 and 18 base pairs.

Zinc finger binding domains can be engineered to bind to a sequence of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416. An engineered zinc finger binding domain can have a novel binding specificity, compared to a naturally-occurring zinc finger protein. Engineering methods include, but are not limited to, rational design and various types of selection.

As provided herein, a ZFP can bind to NBRE and/or NurE. A ZFP can bind to the nucleotide sequence AAAGGT-CAA (SEQ ID NO:44). A ZFP can bind to the nucleotide sequence GATATT(N)GCCAAT; wherein (N) represents a gap of any nucleotide(s) (SEQ ID NO:45). A ZFP can bind to a nucleotide sequence comprising GATATT (SEQ ID NO:48) and GCCAAT (SEQ ID NO:49), optionally wherein SEQ ID NO:48 is 5' to SEQ ID NO:49.

A DBD comprising a ZFP can comprise, e.g., the amino acid sequence of SEQ ID NO: 11.

```
                                          (SEQ ID NO: 11)
LEPGEKPYKCPECGKSFSQSGNLTEHQRTHTGEKPYKCPECGKSFSTSG

HLVRHQRTHTGEKPYKCPECGKSFSQRANLRAHQRTHTGKKTS
```

A DBD comprising a ZFP can comprise, e.g., the amino acid sequence of SEQ ID NO: 12 and/or SEQ ID NO: 13.

```
                                          (SEQ ID NO: 12)
LEPGEKPYKCPECGKSFSHKNALQNHQRTHTGEKPYKCPECGKSFSTSG

NLVRHQRTHTGKKTS
```

```
                                          (SEQ ID NO: 13)
LEPGEKPYKCPECGKSFSDCRDLARHQRTHTGEKPYKCPECGKSFSTTG

NLTVHQRTHTGKKTS
```

In a zinc finger protein comprising the amino acid sequences of SEQ ID NO: 12 and 13, the amino acid sequences of SEQ ID NO:12 and SEQ ID NO:13 can be connected by a linker. The linker can comprise the amino acid sequence of GGSGNGEGSGNG (SEQ ID NO:9). Accordingly, a zinc finger protein can comprise the amino acid sequence of SEQ ID NO: 14.

```
                                          (SEQ ID NO: 14)
LEPGEKPYKCPECGKSFSHKNALQNHQRTHTGEKPYKCPECGKSFSTSG

NLVRHQRTHTGKKTSGGSGNGEGSGNGLEPGEKPYKCPECGKSFSDCRD

LARHQRTHTGEKPYKCPECGKSFSTTGNLTVHQRTHTGKKTS.
```

The DNA-binding domain (DBD) can comprise a sequence that is at least 90, 95%, 96%, 97%, 98%, or 99% identical to one of SEQ ID NOs:4-8, and 10-14, to amino acids 264-339 of SEQ ID NO:1, to amino acids 260-335 of SEQ ID NO:2, or to amino acids 289-364 of SEQ ID NO:3. The DBD can comprise the sequence of any one of SEQ ID NOs:4-8, and 10-14 or amino acids 264-339 of SEQ ID NO:1, amino acids 260-335 of SEQ ID NO:2, or amino acids 289-364 of SEQ ID NO:3.

B. Other Domains of NR4A Super-Repressors

An NR4A super-repressor can contain domains in addition to the DNA-binding domain (DBD), including e.g., domains that increase the ability of the DNA-binding domain to inhibit the transcriptional activity of NR4A1, NR4A2, and/or NR4A3.

An NR4A super-repressor can contain the ligand binding domain (LBD) of NR4A1, NR4A2, and/or NR4A3. Thus, an LBD can comprise amino acids 360-595 of SEQ ID NO:1, amino acids 360-595 of SEQ ID NO:2, and/or amino acids 394-623 of SEQ ID NO:3. An exemplary LBD can comprising the amino acid sequence of SEQ ID NO: 15 or 16.

```
                                          (SEQ ID NO: 15)
PLQQEPSQPSPPSPPICMMNALVRALTDSTPRDLDYSRYCPTDQAAAGT

DAEHVQQFYNLLTASIDVSRSWAEKIPGFTDLPKEDQTLLIESAFLELF
```

-continued

VLRLSIRSNTAEDKFVFCNGLVLHRLQCLRGFGEWLDSIKDFSLNLQSL

NLDIQALACLSALSMITERHGLKEPKRVEELCNKITSSLKDHQSKGQAL

EPTESKVLGALVELRKICTLGLQRIFYLKLEDLVSPPSIIDKLFLDTLP

F (SEQ ID NO: 16)
SPLQQEPSQPSPPSPPICMMNALVRALTDSTPRDLDYSRYCPTDQAAAG

TDAEHVQQFYNLLTASIDVSRSWAEKIPGFTDLPKEDQTLLIESAFLEL

FVLRLSIRSNTAEDKFVFCNGLVLHRLQCLRGFGEWLDSIKDFSLNLQS

LNLDIQALACLSALSMITERHGLKEPKRVEELCNKITSSLKDHQSKGQA

LEPTESKVLGALVELRKICTLGLQRIFYLKLEDLVSPPSIIDKLFLDTL

PF

The ligand-binding domain (LBD) can comprise a sequence that is at least 90, 95%, 96%, 97%, 98%, or 99% identical to SEQ ID NO:15, to SEQ ID NO:16, to amino acids 360-595 of SEQ ID NO:1, to amino acids 360-595 of SEQ ID NO:2, or to amino acids 394-623 of SEQ ID NO:3.

The LBD can be N-terminal or C-terminal to the DBD. The LBD can be linked directly to the N-terminal or C-terminal of the DBD or can be linked to the N- or C-terminus of the DBD via a linker and/or another domain.

An NR4A super-repressor can comprise a Flag domain, e.g., comprising the amino acid sequence of MDYKDHDGDYKDHDIDYKDDDDK (SEQ ID NO: 17).

The FLAG domain can comprise a sequence that is at least 90, 95%, 96%, 97%, 98%, or 99% identical to SEQ ID NO:17.

The Flag domain can be N-terminal or C-terminal to the DBD. The Flag domain can be linked directly to the N-terminal or C-terminal of the DBD or can be linked to the N- or C-terminus of the DBD via a linker and/or another domain.

An NR4A super-repressor can comprise a Krüppel-associated box (KRAB) domain, e.g., comprising the amino acid sequence of (SEQ ID NO: 18)
MDAKSLTAWSRTLVTFKDVFVDFTREEWKLLDTAQQIVYRNVMLENYKN
LVSLGYQLTKPDVILRLEKGEEP.

The KRAB domain can comprise a sequence that is at least 90, 95%, 96%, 97%, 98%, or 99% identical to SEQ ID NO: 18.

The KRAB domain can be N-terminal or C-terminal to the DBD. The KRAB domain can be linked directly to the N-terminal or C-terminal of the DBD or can be linked to the N- or C-terminus of the DBD via a linker and/or another domain.

An NR4A super-repressor can comprise an NCOR domain, e.g., comprising the amino acid sequence of (SEQ ID NO: 19)
MNMNGLMEDPMKVYKDRQFMNVWTDHEKEIFKDKFIQHPKNFGLIASYL ERKSVPDCVLYYYLTKKNENYK or (SEQ ID NO: 20)
MSSSGYPPNQGAFSTEQSRYPPHSVQYTFPNTRHQQEFAVPDYRSSHLE

VSQASQLLQQQQQQQLRRRPSLLSEFHPGSDRPQERRTSYEPFHPGPSP

-continued

VDHDSLESKRPRLEQVSDSHFQRVSAAVLPLVHPLPEGLRASADAKKDP

AFGGKHEAPSSPISGQPCGDDQNASPSKLSKEELIQSMDRVDREIAKVE

QQILKLKKKQQQLEEEAAKPPEPEKPVSPPPVEQKHRSIVQIIYDENRK

KAEEAHKIFEGLGPKVELPLYNQPSDTKVYHENIKTNQVMRKKLILFFK

RRNHARKQREQKICQRYD.

The NCOR domain can comprise a sequence that is at least 90, 95%, 96%, 97%, 98%, or 99% identical to SEQ ID NO:19 or 20.

The NCOR domain can be N-terminal or C-terminal to the DBD. The NCOR domain can be linked directly to the N-terminal or C-terminal of the DBD or can be linked to the N- or C-terminus of the DBD via a linker and/or another domain.

An NR4A super-repressor can comprise a self-cleavage domain, e.g., a T2A domain. A T2A domain can comprise the amino acid sequence (SEQ ID NO: 21)
GSGEGRGSLLTCGDVEENPGP.

The self-cleavage domain can comprise a sequence that is at least 90, 95%, 96%, 97%, 98%, or 99% identical to SEQ ID NO:21.

The self-cleavage domain can be N-terminal or C-terminal to the DBD. The self-cleavage domain can be linked directly to the N-terminal or C-terminal of the DBD or can be linked to the N- or C-terminus of the DBD via a linker and/or another domain. The self-cleavage domain can be between a DBD and an LBD.

An NR4A super-repressor can comprise a nuclear localization signal. A nuclear localization signal can comprise the amino acid sequence PAAKRVKLD (SEQ ID NO:22).

The nuclear localization signal can comprise a sequence that is at least 90, 95%, 96%, 97%, 98%, or 99% identical to SEQ ID NO:22.

The nuclear localization signal can be N-terminal or C-terminal to the DBD. The nuclear localization signal can be linked directly to the N-terminal or C-terminal of the DBD or can be linked to the N- or C-terminus of the DBD via a linker and/or another domain. The nuclear localization signal can be, e.g., in a super-repressor comprising a zinc finger DBD or a TAL DBD.

An NR4A super-repressor can comprise a dimerization domain, for example, a diZIP dimerization domain. A dimerization domain can increase the affinity of a super-repressor for a dimeric binding site. A dimerization domain can comprise the amino acid sequence SQD-PAAAMKQLEDKVEELLSKNYHLENEVARLTKLV (SEQ ID NO:23).

The dimerization domain can comprise a sequence that is at least 90, 95%, 96%, 97%, 98%, or 99% identical to SEQ ID NO:23.

The dimerization domain can be N-terminal or C-terminal to the DBD. The dimerization domain can be linked directly to the N-terminal or C-terminal of the DBD or can be linked to the N- or C-terminus of the DBD via a linker and/or another domain.

An NR4A super-repressor can comprise a transcriptional repressor domain and/or a chromatin compaction domain. The transcriptional repressor domain and/or chromatin compaction domain can comprise the amino acid sequence of SEQ ID NO:24.

(SEQ ID NO: 24)

```
MTMGDKKSPTRPKRQAKPAADEGFWDCSVCTFRNSAEAFKCSICDVRKG

TSTRKPRINSQLVAQQVAQQYATPPPPKKEKKEKVEKQDKEKPEKDKEI

SPSVTKKNTNKKTKPKSDILKDPPSEANSIQSANATTKTSETNHTSRPR

LKNVDRSTAQQLAVTVGNVTVIITDFKEKTRSSSTSSSTVTSSAGSEQQ

NQSSSGSESTDKGSSRSSTPKGDMSAVNDESF
```

The transcriptional repressor domain and/or a chromatin compaction domain can comprise a sequence that is at least 90, 95%, 96%, 97%, 98%, or 99% identical to SEQ ID NO:24.

The transcriptional repressor domain and/or a chromatin compaction domain can be N-terminal or C-terminal to the DBD. The transcriptional repressor domain and/or a chromatin compaction domain can be linked directly to the N-terminal or C-terminal of the DBD or can be linked to the N- or C-terminus of the DBD via a linker and/or another domain.

An NR4A super-repressor can comprise an epitope tag e.g., FLAG, V5, HA, etc. that can be useful for measuring the abundance of the super-repressor. The epitope tag can be N-terminal or C-terminal to the DBD. The epitope tag can be linked directly to the N-terminal or C-terminal of the DBD or can be linked to the N- or C-terminus of the DBD via a linker and/or another domain.

A super-repressor can contain any combination of the above specified domains in any order.

The various domains of NR4A super-repressors can be directly linked or can be connected via a linker. The linker can comprise, for example, GGSGNGEGSGNG (SEQ ID NO:9), GGSG (S-linker; SEQ ID NO:25), GGSGNGGSG (M-linker; SEQ ID NO:26), GGSGNGEGSGNG (L-linker; SEQ ID NO:27), or GSETPGTSESATPES (XTEN; SEQ ID NO:28).

C. Exemplary Super-Repressors

The amino acid sequences of certain exemplary NR4A super-repressors are provided in Table 1 below.

| Molecule | Sequence |
|---|---|
| NR4A3 DBD only | MDYKDFIDGDYKDHDIDYKDDDDKGGSGNGGSGGEGTCAVCGDNAAC QHYGVRTCEGCKGFFKRTVQKNAKYVCLANKNCPVDKRRRNRCQYCRF QKCLSVGMVKEVVRTDSLKGRRGRLPSKPK (SEQ ID NO: 29; aa 1-23 = FLAG; aa 24-32 = linker; aa 33-124 = DBD) |
| Delta-TAF | MDYKDFIDGDYKDHDIDYKDDDDKGGSGNGGSGGEGTCAVCGDNAAC QHYGVRTCEGCKGFFKRTVQKNAKYVCLANKNCPVDKRRRNRCQYCRF QKCLSVGMVKEVVRTDSLKGRRGRLPSKPKSPLQQEPSQPSPPSPPICMM NALVRALTDSTPRDLDYSRYCPTDQAAAGTDAEHVQQFYNLLTASIDVS RSWAEKIPGFTDLPKEDQTLLIESAFLELFVLRLSIRSNTAEDKFVFCNGLV LHRLQCLRGFGEWLDSIKDFSLNLQSLNLDIQALACLSALSMITERHGLKE PKRVEELCNKITSSLKDHQSKGQALEPTESKVLGALVELRKICTLGLQRIF YLKLEDLVSPPSIIDKLFLDTLPF (SEQ ID NO: 30; aa 1-23 = FLAG; aa 24-32 = linker; aa 33-124 = DBD; aa 125-371 = LBD) |
| DBD-KRAB | MDYKDFIDGDYKDHDIDYKDDDDKGGSGNGGSGGEGTCAVCGDNAAC QHYGVRTCEGCKGFFKRTVQKNAKYVCLANKNCPVDKRRRNRCQYCRF QKCLSVGMVKEVVRTDSLKGRRGRLPSKPKSGSETPGTSESATPESMDA KSLTAWSRTLVTFKDVFVDFTREEWKLLDTAQQIVYRNVMLENYKNLVS LGYQLTKPDVILRLEKGEEP (SEQ ID NO: 31; aa 1-23 = FLAG; aa 24-32 = linker; aa 33-124 = DBD; aa 125-140 = XTEN; aa 141-212 = KRAB) |
| KRAB-DBD | MDAKSLTAWSRTLVTFKDVFVDFTREEWKLLDTAQQIVYRNVMLENYK NLVSLGYQLTKPDVILRLEKGEEPGSETPGTSESATPESMDYKDHDGDYK DHDIDYKDDDDKGGSGNGGSGGEGTCAVCGDNAACQHYGVRTCEGCK GFFKRTVQKNAKYVCLANKNCPVDKRRRNRCQYCRFQKCLSVGMVKE VVRTDSLKGRRGRLPSKPKS (SEQ ID NO: 32; aa 1-72 = KRAB; aa 73-88 = XTEN; aa 89-110 = FLAG; aa 111-119 = linker; aa 120-212 = DBD) |
| NCOR Trunc | MNNINGLMEDPMKVYKDRQFMNVWTDHEKEIFKDKFIQHPKNFGLIASY LERKSVPDCVLYYYLTKKNENYKSGSETPGTSESATPESMDYKDHDGDY KDHDIDYKDDDDKGGSGNGGSGGEGTCAVCGDNAACQHYGVRTCEGC KGFFKRTVQKNAKYVCLANKNCPVDKRRRNRCQYCRFQKCLSVGMVK EVVRTDSLKGRRGRLPSKPKSPLQQEPSQPSPPSPPICMMNALVRALTDST PRDLDYSRYCPTDQAAAGTDAEHVQQFYNLLTASIDVSRSWAEKIPGFTD LPKEDQTLLIESAFLELFVLRLSIRSNTAEDKFVFCNGLVLHRLQCLRGFG EWLDSIKDFSLNLQSLNLDIQALACLSALSMITERHGLKEPKRVEELCNKI TSSLKDHQSKGQALEPTESKVLGALVELRKICTLGLQRIFYLKLEDLVSPP SIIDKLFLDTLPF (SEQ ID NO: 33; aa 1-71 = NCOR Trunc; aa 72-87 = XTEN; aa 88-110 = FLAG; aa 111-119 = linker; aa 120-211 = DBD; aa 212-458 = LBD) |
| KRAB-DBD-LBD | MDAKSLTAWSRTLVTFKDVFVDFTREEWKLLDTAQQIVYRNVMLENYK NLVSLGYQLTKPDVILRLEKGEEPGSGETPGTSESATPESMDYKDEEDGDY KDHDIDYKDDDDKGGSGNGGSGGEGTCAVCGDNAACQHYGVRTCEGC KGFFKRTVQKNAKYVCLANKNCPVDKRRRNRCQYCRFQKCLSVGMVK EVVRTDSLKGRRGRLPSKPKSPLQQEPSQPSPPSPPICMMNALVRALTDST PRDLDYSRYCPTDQAAAGTDAEHVQQFYNLLTASIDVSRSWAEKIPGFTD LPKEDQTLLIESAFLELFVLRLSIRSNTAEDKFVFCNGLVLHRLQCLRGFG EWLDSIKDFSLNLQSLNLDIQALACLSALSMITERHGLKEPKRVEELCNKI TSSLKDHQSKGQALEPTESKVLGALVELRKICTLGLQRIFYLKLEDLVSPP SIIDKLFLDTLPF (SEQ ID NO: 34; aa 1-72 = KRAB; aa 73-88 = XTEN; aa 89-111 = FLAG; aa 112-120 = linker; aa 121-212 = DBD; aa 213-459 = LBD) |

-continued

| Molecule | Sequence |
| --- | --- |
| RD1 | MSSSGYPPNQGAFSTEQSRYPPHSVQYTFPNTRHQQEFAVPDYRSSHLEV<br>SQASQLLQQQQQQQLRRRPSLLSEFHPGSDRPQERRTSYEPFHPGPSPVDH<br>DSLESKRPRLEQVSDSHFQRVSAAVLPLVHPLPEGLRASADAKKDPAFGG<br>KHEAPSSPISGQPCGDDQNASPSKLSKEELIQSMDRVDREIAKVEQQILKL<br>KKKQQQLEEEAAKPPEPEKPVSPPPVEQKHRSIVQIIYDENRKKAEEAHKI<br>FEGLGPKVELPLYNQPSDTKVYHENIKTNQVMRKKLILFFKRRNHARKQ<br>REQKICQRYDSGSETPGTSESATPESMDYKDHDGDYKDHDIDYKDDDDK<br>GGSGNGGSGGEGTCAVCGDNAACQHYGVRTCEGCKGFFKRTVQKNAK<br>YVCLANKNCPVDKRRRNRCQYCRFQKCLSVGMVKEVVRTDSLKGRRGR<br>LPSKPKSPLQQEPSQPSPPSPPICMMNALVRALTDSTPRDLDYSRYCPTDQ<br>AAAGTDAEHVQQFYNLLTASIDVSRSWAEKIPGFTDLPKEDQTLLIESAFL<br>ELFVLRLSIRSNTAEDKFVFCNGLVLHRLQCLRGFGEWLDSIKDFSLNLQS<br>LNLDIQALACLSALSMITERHGLKEPKRVEELCNKITSSLKDHQSKGQALE<br>PTESKVLGALVELRKICTLGLQRIFYLKLEDLVSPPSIIDKLFLDTLPF (SEQ<br>ID NO: 35; aa 1-312 = NCOR RD1; aa 313-328 = XTEN;<br>aa 329-351 = FLAG; aa 352-360 = linker; aa 361-452 =<br>DBD; aa 453-699 = LBD) |
| DBD-T2A-<br>LBD | GEGTCAVCGDNAACQHYGVRTCEGCKGFFKRTVQKNAKYVCLANKNC<br>PVDKRRRNRCQYCRFQKCLSVGMVKEVVRTDSLKGRRGRLPSKPKGSGE<br>GRGSLLTCGDVEENPGPSPLQQEPSQPSPPSPPICMMNALVRALTDSTPRD<br>LDYSRYCPTDQAAAGTDAEHVQQFYNLLTASIDVSRSWAEKIPGFTDLPK<br>EDQTLLIESAFLELFVLRLSIRSNTAEDKFVFCNGLVLHRLQCLRGFGEWL<br>DSIKDFSLNLQSLNLDIQALACLSALSMITERHGLKEPKRVEELCNKITSSL<br>KDHQSKGQALEPTESKVLGALVELRKICTLGLQRIFYLKLEDLVSPPSIIDK<br>LFLDTLPF (SEQ ID NO: 36; aa 1-92 = DBD; aa 93-113 =<br>T2A; aa 114-360 = LBD) |
| ZF DBD for<br>AAA GGT<br>CAA (SEQ<br>ID NO: 44) | LEPGEKPYKCPECGKSFSQSGNLTEHQRTHTGEKPYKCPECGKSFSTSGH<br>LVRHQRTHTGEKPYKCPECGKSFSQRANLRAHQRTHTGKKTSGGSGPAA<br>KRVKLD (SEQ ID NO: 37; aa 1-92 = ZF; aa 93-96 =<br>linker; aa 97-105 = NLS) |
| Zinc finger<br>DBD for<br>GATATT<br>(N)GCC<br>AAT (SEQ<br>ID NO:45) | LEPGEKPYKCPECGKSFSHKNALQNHQRTHTGEKPYKCPECGKSFSTSGN<br>LVRHQRTHTGKKTSGGSGNGEGSGNGLEPGEKPYKCPECGKSFSDCRDL<br>ARHQRTHTGEKPYKCPECGKSFSTTGNLTVHQRTHTGKKTSGGSGPAAK<br>RVKLD (SEQ ID NO: 38; aa 1-64 = ZF; aa 65-76 = linker;<br>aa 77-140 ZF; aa 141-144 linker; aa 145-153 - NLS) |
| TAL for<br>binding<br>NBRE | MLTPEQVVAIASNHGGKQALETVQRLLPVCQAHGLTPEQVVAIASNIGG<br>KQALETVQRLLPVCQAHGLTPEQVVAIASNGGGKQALETVQRLLPVCQA<br>HGLTPEQVVAIASNIGGKQALETVQRLLPVCQAHGLTPEQVVAIASNGGG<br>KQALETVQRLLPVCQAHGLTPEQVVAIASNGGGKQALETVQRLLPVCQA<br>HGLTPEQVVAIASNGGGKQALETVQRLLPVCQAHGGGSGPAAKRVKLD<br>(SEQ ID NO: 39; aa 1-232 = TAL; aa 233-236 = linker;<br>aa 237-245 = NLS) |
| TAL for<br>binding<br>NurE | MLTPEQVVAIASNHGGKQALETVQRLLPVCQAHGLTPEQVVAIASNIGG<br>KQALETVQRLLPVCQAHGLTPEQVVAIASNGGGKQALETVQRLLPVCQA<br>HGLTPEQVVAIASNIGGKQALETVQRLLPVCQAHGLTPEQVVAIASNGGG<br>KQALETVQRLLPVCQAHGLTPEQVVAIASNGGGKQALETVQRLLPVCQA<br>HGLTPEQVVAIASNGGGKQALETVQRLLPVCQAHGGGSGNGEGSGNGLT<br>PEQVVAIASNIGGKQALETVQRLLPVCQAHGLTPEQVVAIASNIGGKQAL<br>ETVQRLLPVCQAHGLTPEQVVAIASNIGGKQALETVQRLLPVCQAHGLTP<br>EQVVAIASNGGGKQALETVQRLLPVCQAHGLTPEQVVAIASNHGGKQAL<br>ETVQRLLPVCQAHGLTPEQVVAIASHDGGKQALETVQRLLPVCQAHGLT<br>PEQVVAIASHDGGKQALETVQRLLPVCQAHGGGSGPAAKRVKLD (SEQ<br>ID NO: 40; aa 1-232 = TAL; aa 233-244 = linker;<br>aa 245-475 = TAL; aa 476-479 = linker;<br>aa 480-488 = NLS) |
| hsNR4A3_<br>DBD-linker-<br>diZIP | MGEGTCAVCGDNAACQHYGVRTCEGCKGFFKRTVQKNAKYVCLANKN<br>CPVDKRRRNRCQYCRFQKCLSVGMVKEVVRTDSLKGRRGRLPSKPKGG<br>SGNGSGSQDPAAAMKQLEDKVEELLSKNYHLENEVARLTKLVGGSG<br>(SEQ ID NO: 41; aa 2-93 = DBD; aa 94-101 = M-linker;<br>aa 102-137 = diZIP; aa 138-141 = S-linker) |
| hsNR4A3_<br>diZIP-<br>linker-DBD | MGGSGSQDPAAAMKQLEDKVEELLSKNYHLENEVARLTKLVGGSGNGS<br>GGGEGTCAVCGDNAACQHYGVRTCEGCKGFFKRTVQKNAKYVCLANKN<br>CPVDKRRRNRCQYCRFQKCLSVGMVKEVVRTDSLKGRRGRLPSKPK<br>(SEQ ID NO: 42; aa 2-5 = S-linker; aa 6-41 = diZIP;<br>aa 42-49 = M-linker; aa 50-141 = DBD) |
| hsRYBP-<br>hsNR4A3_<br>RYBP-<br>linker-DBD | MGGSGGDKKSPTRPKRQAKPAADEGFWDCSVCTFRNSAEAFKCSICDVR<br>KGTSTRKPRINSQLVAQQVAQQYATPPPPKKEKKEKVEKQDKEKPEKDK<br>EISPSVTKKNTNKKTKPKSDILKDPPSEANSIQSANATTKTSETNHTSRPRL<br>KNVDRSTAQQLAVTVGNVTVIITDFKEKTRSSSTSSSTVTSSAGSEQQNQS<br>SSGSESTDKGSSRSSTPKGDMSAVNDESFGGSGNGEGSGNGGEGTCAVC<br>GDNAACQHYGVRTCEGCKGFFKRTVQKNAKYVCLANKNCPVDKRRRN<br>RCQYCRFQKCLSVGMVKEVVRTDSLKGRRGRLPSKPK<br>(SEQ ID NO: 43; aa 2-5 = S-linker; aa 6-230 = hsRYBD;<br>aa 231-242 = L-liker; aa 243-334 = DBD) |

A super-repressor can comprise a sequence that is at least 90, 95%, 96%, 97%, 98%, or 99% identical to any one of SEQ ID NOs:29-43. The amino acid sequence of a super-repressor can comprise, consist essentially of, or consist of the amino acid sequence of any one of SEQ ID NOs:29-43.

III. Modified Immune Effector Cells

In some embodiments, the present disclosure provides modified immune effector cells. Herein, the term "modified immune effector cells" encompasses immune effector cells comprising a polynucleotide encoding a NR4A super-repressor and immune effector cells comprising one or more NR4A super-repressors. Herein, an "un-modified immune effector cell" or "control immune effector cell" refers to a cell or population of cells wherein the cells do not comprise a polynucleotide encoding a NR4A super-repressor or a NR4A super-repressor.

The term "immune effector cell" refers to cells involved in mounting innate and adaptive immune responses, including but not limited to lymphocytes (such as T-cells (including thymocytes) and B-cells), natural killer (NK) cells, NKT cells, macrophages, monocytes, eosinophils, basophils, neutrophils, dendritic cells, and mast cells. In some embodiments, the modified immune effector cell is a T cell, such as a CD4+ T cell, a CD8+ T cell (also referred to as a cytotoxic T cell or CTL), a regulatory T cell (Treg), a Th1 cell, a Th2 cell, or a Th17 cell.

In some embodiments, the modified immune effector cell is a T cell. In some embodiments, T cells are isolated from a subject, expanded ex vivo, and re-infused into a subject. In some embodiments, T cells are modified to express one or more exogenous receptors specific for an autologous tumor antigen, expanded ex vivo, and re-infused into the subject. Such embodiments can be modeled using in vivo mouse models wherein mice have been transplanted with a cancer cell line expressing a cancer antigen (e.g., CD19) and are treated with modified T cells that express an exogenous receptor that is specific for the cancer antigen In some embodiments, the modified immune effector cell is a T cell that has been isolated from a tumor sample (referred to herein as "tumor infiltrating lymphocytes" or "TILs"). Without wishing to be bound by theory, it is thought that TILs possess increase specificity to tumor antigens (Radvanyi et al., 2012 Clin Canc Res 18:6758-6770) and can therefore mediate tumor antigen-specific immune response (e.g., activation, proliferation, and cytotoxic activity against the cancer cell) leading to cancer cell destruction (Brudno et al., 2018 Nat Rev Clin Onc 15:31-46)) without the introduction of an exogenous engineered receptor. Therefore, in some embodiments, TILs are isolated from a tumor in a subject, expanded ex vivo, and re-infused into a subject. In some embodiments, TILs are modified to express one or more exogenous receptors specific for an autologous tumor antigen, expanded ex vivo, and re-infused into the subject. Such embodiments can be modeled using in vivo mouse models wherein mice have been transplanted with a cancer cell line expressing a cancer antigen (e.g., CD19) and are treated with modified T cells that express an exogenous receptor that is specific for the cancer antigen.

In some embodiments, the modified immune effector cell is an animal cell or is derived from an animal cell, including invertebrate animals and vertebrate animals (e.g., fish, amphibian, reptile, bird, or mammal). In some embodiments, the modified immune effector cell is a mammalian cell or is derived from a mammalian cell (e.g., a pig, a cow, a goat, a sheep, a rodent, a non-human primate, a human, etc.). In some embodiments, the modified immune effector cell is a rodent cell or is derived from a rodent cell (e.g., a rat or a mouse). In some embodiments, the modified immune effector cell is a human cell or is derived from a human cell.

In some embodiments, the modified immune effector cells comprise a polynucleotide encoding a NR4A super-repressor or a NR4A super-repressor that reduces the transcriptional activity of endogenous NR4A1, NR4A2, and/or NR4A3. In some embodiments, a polynucleotide sequence encoding a NR4A super-repressor is inserted at one or more locations in the genome.

In some embodiments, the expression of one or more NR4A target genes in a modified immune effector cell is reduced by at least 5% compared to the expression of the NR4A target genes in an unmodified immune effector cell. In some embodiments, the expression of the one or more NR4A target genes in a modified immune effector cell is reduced by at least 10%, 20%, 30%, 40%, 50%, 60%, 70%, 80%, 90%, or more compared to the expression of the NR4A target genes in an unmodified immune effector cell. In some embodiments, the modified immune effector cells described herein demonstrate reduced expression and/or function of gene products encoded by a plurality (e.g., two or more) of endogenous NR4A target genes compared to the expression of the gene products in an unmodified immune effector cell. For example, in some embodiments, a modified immune effector cell demonstrates reduced expression and/or function of gene products from 1, 2, 3, 4, 5, 6, 7, 8, 9, 10, or more endogenous NR4A target genes compared to the expression of the gene products in an unmodified immune effector cell.

In some embodiments, one or more polynucleotides encoding the NR4A super-repressor are inserted into the genome of the immune effector cell. In some embodiments, one or more polynucleotides encoding the NR4A super-repressor are expressed episomaly and are not inserted into the genome of the immune effector cell.

In some embodiments, the modified immune effector cells described herein comprise a polynucleotide encoding a super-repressor or a super-repressor and further comprise one or more exogenous transgenes inserted at one or more genomic loci (e.g., a genetic "knock-in"). In some embodiments, the one or more exogenous transgenes encode detectable tags, safety-switch systems, chimeric switch receptors, and/or engineered antigen-specific receptors.

In some embodiments, the modified immune effector cells described herein further comprise an exogenous transgene encoding a detectable tag. Examples of detectable tags include but are not limited to, FLAG tags, poly-histidine tags (e.g. 6×His), SNAP tags, Halo tags, cMyc tags, glutathione-S-transferase tags, avidin, enzymes, fluorescent proteins, luminescent proteins, chemiluminescent proteins, bioluminescent proteins, and phosphorescent proteins. In some embodiments the fluorescent protein is selected from the group consisting of blue/UV proteins (such as BFP, TagBFP, mTagBFP2, Azurite, EBFP2, mKalamal, Sirius, Sapphire, and T-Sapphire); cyan proteins (such as CFP, eCFP, Cerulean, SCFP3A, mTurquoise, mTurquoise2, monomeric Midoriishi-Cyan, TagCFP, and mTFP1); green proteins (such as: GFP, eGFP, meGFP (A208K mutation), Emerald, Superfolder GFP, Monomeric Azami Green, TagGFP2, mUKG, mWasabi, Clover, and mNeonGreen); yellow proteins (such as YFP, eYFP, Citrine, Venus, SYFP2, and TagYFP); orange proteins (such as Monomeric Kusabira-Orange, mKOK, mKO2, mOrange, and mOrange2); red proteins (such as RFP, mRaspberry, mCherry, mStrawberry, mTangerine, tdTomato, TagRFP, TagRFP-T, mApple, mRuby, and mRuby2); far-red proteins (such as mPlum, HcRed-Tandem, mKate2, mNeptune, and NirFP); near-infrared proteins (such as TagRFP657, IFP1.4, and iRFP); long stokes shift proteins (such as mKeima Red, LSS-mKate1, LSS-mKate2, and mBeRFP); photoactivatible proteins (such as PA-GFP, PAmCherryl, and PATagRFP); photoconvertible proteins (such as Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, and PSmOrange); and photoswitchable proteins (such as Dronpa). In some embodiments, the detectable tag can be selected from AmCyan, AsRed, DsRed2, DsRed Express, E2-Crimson, HcRed, ZsGreen, ZsYellow, mCherry, mStrawberry, mOrange, mBanana, mPlum, mRasberry, tdTomato, DsRed Monomer, and/or AcGFP, all of which are available from Clontech.

In some embodiments, the modified immune effector cells described herein further comprise an exogenous transgene encoding a safety-switch system. Safety-switch systems (also referred to in the art as suicide gene systems) comprise exogenous transgenes encoding for one or more proteins that enable the elimination of a modified immune effector cell after the cell has been administered to a subject. Examples of safety-switch systems are known in the art. For example, safety-switch systems include genes encoding for proteins that convert non-toxic pro-drugs into toxic compounds such as the Herpes simplex thymidine kinase (Hsv-tk) and ganciclovir (GCV) system (Hsv-tk/GCV). Hsv-tk converts non-toxic GCV into a cytotoxic compound that leads to cellular apoptosis. As such, administration of GCV to a subject that has been treated with modified immune effector cells comprising a transgene encoding the Hsv-tk protein can selectively eliminate the modified immune effector cells while sparing endogenous immune effector cells. (See e.g., Bonini et al., Science, 1997, 276(5319):1719-1724; Ciceri et al., Blood, 2007, 109(11):1828-1836; Bondanza et al., Blood 2006, 107(5):1828-1836).

Additional safety-switch systems include genes encoding for cell-surface markers, enabling elimination of modified immune effector cells by administration of a monoclonal antibody specific for the cell-surface marker via ADCC. In some embodiments, the cell-surface marker is CD20 and the modified immune effector cells can be eliminated by administration of an anti-CD20 monoclonal antibody such as Rituximab (See e.g., Introna et al., Hum Gene Ther, 2000, 11(4):611-620; Serafini et al., Hum Gene Ther, 2004, 14, 63-76; van Meerten et al., Gene Ther, 2006, 13, 789-797). Similar systems using EGF-R and Cetuximab or Panitumumab are described in International PCT Publication No. WO 2018006880. Additional safety-switch systems include transgenes encoding pro-apoptotic molecules comprising one or more binding sites for a chemical inducer of dimerization (CID), enabling elimination of modified immune effector cells by administration of a CID which induces oligomerization of the pro-apoptotic molecules and activation of the apoptosis pathway. In some embodiments, the pro-apoptotic molecule is Fas (also known as CD95) (Thomis et al., Blood, 2001, 97(5), 1249-1257). In some embodiments, the pro-apoptotic molecule is caspase-9 (Straathof et al., Blood, 2005, 105(11), 4247-4254).

In some embodiments, the modified immune effector cells described herein further comprise an exogenous transgene encoding a chimeric switch receptor. Chimeric switch receptors are engineered cell-surface receptors comprising an extracellular domain from an endogenous cell-surface receptor and a heterologous intracellular signaling domain, such that ligand recognition by the extracellular domain results in activation of a different signaling cascade than that activated by the wild type form of the cell-surface receptor. In some embodiments, the chimeric switch receptor comprises the extracellular domain of an inhibitory cell-surface receptor fused to an intracellular domain that leads to the transmission of an activating signal rather than the inhibitory signal normally transduced by the inhibitory cell-surface receptor. In particular embodiments, extracellular domains derived from cell-surface receptors known to inhibit immune effector cell activation can be fused to activating intracellular domains. Engagement of the corresponding ligand will then activate signaling cascades that increase, rather than inhibit, the activation of the immune effector cell. For example, in some embodiments, the modified immune effector cells described herein comprise a transgene encoding a PD1-CD28 switch receptor, wherein the extracellular domain of PD1 is fused to the intracellular signaling domain of CD28 (See e.g., Liu et al., Cancer Res 76:6 (2016), 1578-1590 and Moon et al., Molecular Therapy 22 (2014), S201). In some embodiments, the modified immune effector cells described herein comprise a transgene encoding the extracellular domain of CD200R and the intracellular signaling domain of CD28 (See Oda et al., Blood 130:22 (2017), 2410-2419).

In some embodiments, the modified immune effector cells described herein further comprise an engineered antigen-specific receptor recognizing a protein target expressed by a target cell, such as a tumor cell or an antigen presenting cell (APC), referred to herein as "modified receptor-engineered cells" or "modified RE-cells". The term "engineered antigen receptor" refers to a non-naturally occurring antigen-specific receptor such as a chimeric antigen receptor (CAR) or a recombinant T cell receptor (TCR). In some embodiments, the engineered antigen receptor is a CAR comprising an extracellular antigen binding domain fused via hinge and transmembrane domains to a cytoplasmic domain comprising a signaling domain. In some embodiments, the CAR extracellular domain binds to an antigen expressed by a target cell in an MHC-independent manner leading to activation and proliferation of the RE cell. In some embodiments, the extracellular domain of a CAR recognizes a tag fused to an antibody or antigen-binding fragment thereof. In such embodiments, the antigen-specificity of the CAR is dependent on the antigen-specificity of the labeled antibody, such that a single CAR construct can be used to target multiple different antigens by substituting one antibody for another (See e.g., U.S. Pat. Nos. 9,233,125 and 9,624,279; US Patent Application Publication Nos. 20150238631 and 20180104354). In some embodiments, the extracellular domain of a CAR may comprise an antigen binding fragment derived from an antibody. Antigen binding domains that are useful in the present disclosure include, for example, scFvs; antibodies; antigen binding regions of antibodies; variable regions of the heavy/light chains; and single chain antibodies.

In some embodiments, the intracellular signaling domain of a CAR may be derived from the TCR complex zeta chain (such as CD3ξ signaling domains), FcγRIII, FcεRI, or the T-lymphocyte activation domain. In some embodiments, the intracellular signaling domain of a CAR further comprises a costimulatory domain, for example a 4-1BB, CD28, CD40, MyD88, or CD70 domain. In some embodiments, the intracellular signaling domain of a CAR comprises two costimulatory domains, for example any two of 4-1BB, CD28, CD40, MyD88, or CD70 domains. Exemplary CAR structures and intracellular signaling domains are known in the art (See e.g., WO 2009/091826; US 20130287748; WO 2015/142675; WO 2014/055657; and WO 2015/090229, incorporated herein by reference).

CARs specific for a variety of tumor antigens are known in the art, for example CD171-specific CARs (Park et al., Mol Ther (2007) 15(4):825-833), EGFRvIII-specific CARs (Morgan et al., Hum Gene Ther (2012) 23(10):1043-1053), EGF-R-specific CARs (Kobold et al., J Natl Cancer Inst (2014) 107(1):364), carbonic anhydrase K-specific CARs (Lamers et al., Biochem Soc Trans (2016) 44(3):951-959), FR-α-specific CARs (Kershaw et al., Clin Cancer Res (2006) 12(20):6106-6015), HER2-specific CARs (Ahmed et al., J Clin Oncol (2015) 33(15)1688-1696; Nakazawa et al., Mol Ther (2011) 19(12):2133-2143; Ahmed et al., Mol Ther (2009) 17(10):1779-1787; Luo et al., Cell Res (2016) 26(7): 850-853; Morgan et al., Mol Ther (2010) 18(4):843-851; Grada et al., Mol Ther Nucleic Acids (2013) 9(2):32), CEA-specific CARs (Katz et al., Clin Cancer Res (2015) 21(14):3149-3159), IL13Rα2-specific CARs (Brown et al., Clin Cancer Res (2015) 21(18):4062-4072), GD2-specific CARs (Louis et al., Blood (2011) 118(23):6050-6056; Caruana et al., Nat Med (2015) 21(5):524-529), ErbB2-specific CARs (Wilkie et al., J Clin Immunol (2012) 32(5): 1059-1070), VEGF-R-specific CARs (Chinnasamy et al., Cancer Res (2016) 22(2):436-447), FAP-specific CARs (Wang et al., Cancer Immunol Res (2014) 2(2):154-166), MSLN-specific CARs (Moon et al, Clin Cancer Res (2011) 17(14):4719-30), NKG2D-specific CARs (VanSeggelen et al., Mol Ther (2015) 23(10):1600-1610), CD19-specific CARs (Axicabtagene ciloleucel (Yescarta®) and Tisagenlecleucel (Kymriah®). See also, Li et al., J Hematol and Oncol (2018) 11(22), reviewing clinical trials of tumor-specific CARs.

In some embodiments, the engineered antigen receptor is an engineered TCR. Engineered TCRs comprise TCRa and/or TCRO chains that have been isolated and cloned from T cell populations recognizing a particular target antigen. For example, TCRa and/or TCR3 genes (i.e., TRAC and TRBC) can be cloned from T cell populations isolated from individuals with particular malignancies or T cell populations that have been isolated from humanized mice immunized with specific tumor antigens or tumor cells. Engineered TCRs recognize antigen through the same mechanisms as their endogenous counterparts (e.g., by recognition of their cognate antigen presented in the context of major histocompatibility complex (MHC) proteins expressed on the surface of a target cell). This antigen engagement stimulates endogenous signal transduction pathways leading to activation and proliferation of the TCR-engineered cells.

Engineered TCRs specific for tumor antigens are known in the art, for example WT1-specific TCRs (JTCR016, Juno Therapeutics; WT1-TCRc4, described in US Patent Application Publication No. 20160083449), MART-1 specific TCRs (including the DMF4T clone, described in Morgan et al., Science 314 (2006) 126-129); the DMF5T clone, described in Johnson et al., Blood 114 (2009) 535-546); and the ID3T clone, described in van den Berg et al., Mol. Ther. 23 (2015) 1541-1550), gp100-specific TCRs (Johnson et al., Blood 114 (2009) 535-546), CEA-specific TCRs (Parkhurst et al., Mol Ther. 19 (2011) 620-626), NY-ESO and LAGE-1 specific TCRs (1G4T clone, described in Robbins et al., J Clin Oncol 26 (2011) 917-924; Robbins et al., Clin Cancer Res 21 (2015) 1019-1027; and Rapoport et al., Nature Medicine 21 (2015) 914-921), and MAGE-A3-specific TCRs (Morgan et al., J Immunother 36 (2013) 133-151) and Linette et al., Blood 122 (2013) 227-242). (See also, Debets et al., Seminars in Immunology 23 (2016) 10-21).

In some embodiments, the engineered antigen receptor is directed against a target antigen selected from a cluster of differentiation molecule, such as CD3, CD4, CD8, CD16, CD24, CD25, CD33, CD34, CD45, CD64, CD71, CD78, CD80 (also known as B7-1), CD86 (also known as B7-2), CD96, CD116, CD117, CD123, CD133, and CD138, CD371 (also known as CLL1); a tumor-associated surface antigen, such as 5T4, BCMA (also known as CD269 and TNFRSF17, UniProt #Q02223), carcinoembryonic antigen (CEA), carbonic anhydrase 9 (CAIX or MN/CAIX), CD19, CD20, CD22, CD30, CD40, disialogangliosides such as GD2, ELF2M, ductal-epithelial mucin, ephrin B2, epithelial cell adhesion molecule (EpCAM), ErbB2 (HER2/neu), FCRL5 (UniProt #Q68SN8), FKBP11 (UniProt #Q9NYL4), glioma-associated antigen, glycosphingolipids, gp36, GPRC5D (UniProt #Q9NZD1), mut hsp70-2, intestinal carboxyl esterase, IGF-I receptor, ITGA8 (UniProt #P53708), KAMP3, LAGE-la, MAGE, mesothelin, neutrophil elastase, NKG2D, Nkp30, NY-ESO-1, PAP, prostase, prostate-carcinoma tumor antigen-1 (PCTA-1), prostate specific antigen (PSA), PSMA, prostein, RAGE-1, ROR1, RU1 (SFMBTI), RU2 (DCDCl$_2$), SLAMF7 (UniProt #Q9NQ25), survivin, TAG-72, and telomerase; a major histocompatibility complex (MHC) molecule presenting a tumor-specific peptide epitope; tumor stromal antigens, such as the extra domain A (EDA) and extra domain B (EDB) of fibronectin; the A1 domain of tenascin-C (TnC A1) and fibroblast associated protein (FAP); cytokine receptors, such as epidermal growth factor receptor (EGFR), EGFR variant III (EGFRvIII), TFGβ-R or components thereof such as endoglin; a major histocompatibility complex (MHC) molecule; a virus-specific surface antigen such as an HIV-specific antigen (such as HIV gp120); an EBV-specific antigen, a CMV-specific antigen, a HPV-specific antigen, a Lassa virus-specific antigen, an Influenza virus-specific antigen as well as any derivate or variant of these surface antigens.

A. Effector Functions

In some embodiments, the modified immune effector cells described herein demonstrate an increase in one or more immune cell effector functions. Herein, the term "effector function" refers to functions of an immune cell related to the generation, maintenance, and/or enhancement of an immune response against a target cell or target antigen. In some embodiments, the modified immune effector cells described herein demonstrate one or more of the following characteristics compared to an unmodified immune effector cell: increased infiltration or migration in to a tumor, increased proliferation, increased or prolonged cell viability, increased resistance to inhibitory factors in the surrounding microenvironment such that the activation state of the cell is prolonged or increased, increased production of pro-inflammatory immune factors (e.g., pro-inflammatory cytokines, chemokines, and/or enzymes), increased cytotoxicity, and/or increased resistance to exhaustion.

In some embodiments, the modified immune effector cells described herein demonstrate increased infiltration into a tumor compared to an unmodified immune effector cell. In some embodiments, increased tumor infiltration by modified immune effector cells refers to an increase the number of modified immune effector cells infiltrating into a tumor during a given period of time compared to the number of unmodified immune effector cells that infiltrate into a tumor during the same period of time. In some embodiments, the modified immune effector cells demonstrate a 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more fold increase in tumor filtration compared to an unmodified immune cell. Tumor infiltration can be measured by isolating one or more tumors from a subject and assessing the number of modified immune cells in the sample by flow cytometry, immunohistochemistry, and/or immunofluorescence.

In some embodiments, the modified immune effector cells described herein demonstrate an increase in cell proliferation compared to an unmodified immune effector cell. In these embodiments, the result is an increase in the number of modified immune effector cells present compared to unmodified immune effector cells after a given period of time. For example, in some embodiments, modified immune effector cells demonstrate increased rates of proliferation compared to unmodified immune effector cells, wherein the modified immune effector cells divide at a more rapid rate than unmodified immune effector cells. In some embodiments, the modified immune effector cells demonstrate a 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more fold increase in the rate of proliferation compared to an unmodified immune cell. In some embodiments, modified immune effector cells demonstrate prolonged periods of proliferation compared to unmodified immune effector cells, wherein the modified immune effector cells and unmodified immune effector cells divide at similar rates, but wherein the modified immune effector cells maintain the proliferative state for a longer period of time. In some embodiments, the modified immune effector cells maintain a proliferative state for 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more times longer than an unmodified immune cell.

In some embodiments, the modified immune effector cells described herein demonstrate increased or prolonged cell viability compared to an unmodified immune effector cell. In such embodiments, the result is an increase in the number of modified immune effector cells or present compared to unmodified immune effector cells after a given period of time. For example, in some embodiments, modified immune effector cells described herein remain viable and persist for 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more times longer than an unmodified immune cell.

In some embodiments, the modified immune effector cells described herein demonstrate increased resistance to inhibitory factors compared to an unmodified immune effector cell. Exemplary inhibitory factors include signaling by immune checkpoint molecules (e.g., PD1, PDL1, CTLA4, LAG3, IDO) and/or inhibitory cytokines (e.g., IL-10, TGFβ).

In some embodiments, the modified T cells described herein demonstrate increased resistance to T cell exhaustion compared to an unmodified T cell. T cell exhaustion is a state of antigen-specific T cell dysfunction characterized by decreased effector function and leading to subsequent deletion of the antigen-specific T cells. In some embodiments, exhausted T cells lack the ability to proliferate in response to antigen, demonstrate decreased cytokine production, and/or demonstrate decreased cytotoxicity against target cells such as tumor cells. In some embodiments, exhausted T cells are identified by altered expression of cell surface markers and transcription factors, such as decreased cell surface expression of CD122 and CD127; increased expression of inhibitory cell surface markers such as PD1, LAG3, CD244, CD160, TIM3, and/or CTLA4; and/or increased expression of transcription factors such as Blimp1, NFAT, and/or BATF.

In some embodiments, exhausted T cells demonstrate altered sensitivity cytokine signaling, such as increased sensitivity to TGFβ signaling and/or decreased sensitivity to IL-7 and IL-15 signaling. T cell exhaustion can be determined, for example, by co-culturing the T cells with a population of target cells and measuring T cell proliferation, cytokine production, and/or lysis of the target cells. In some embodiments, the modified immune effector cells described herein are co-cultured with a population of target cells (e.g., autologous tumor cells or cell lines that have been engineered to express a target tumor antigen) and effector cell proliferation, cytokine production, and/or target cell lysis is measured. These results are then compared to the results obtained from co-culture of target cells with a control population of immune cells (such as unmodified immune effector cells or immune effector cells that have a control modification).

In some embodiments, resistance to T cell exhaustion is demonstrated by increased production of one or more cytokines (e.g., IFNγ, TNFα, or IL-2) from the modified immune effector cells compared to the cytokine production observed from the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in cytokine production from the modified immune effector cells compared to the cytokine production from the control population of immune cells is indicative of an increased resistance to T cell exhaustion. In some embodiments, resistance to T cell exhaustion is demonstrated by increased proliferation of the modified immune effector cells compared to the proliferation observed from the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in proliferation of the modified immune effector cells compared to the proliferation of the control population of immune cells is indicative of an increased resistance to T cell exhaustion. In some embodiments, resistance to T cell exhaustion is demonstrated by increased target cell lysis by the modified immune effector cells compared to the target cell lysis observed by the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in target cell lysis by the modified immune effector cells compared to the target cell lysis by the control population of immune cells is indicative of an increased resistance to T cell exhaustion.

In some embodiments, exhaustion of the modified immune effector cells compared to control populations of immune cells is measured during the in vitro or ex vivo manufacturing process. For example, in some embodiments, TILs isolated from tumor fragments are modified according to the methods described herein and then expanded in one or more rounds of expansion to produce a population of modified TILs. In such embodiments, the exhaustion of the modified TILs can be determined immediately after harvest and prior to a first round of expansion, after the first round of expansion but prior to a second round of expansion, and/or after the first and the second round of expansion. In some embodiments, exhaustion of the modified immune effector cells compared to control populations of immune cells is measured at one or more time points after transfer of the modified immune effector cells into a subject. For example, in some embodiments, the modified cells are produced according to the methods described herein and administered to a subject. Samples can then be taken from the subject at various time points after the transfer to determine exhaustion of the modified immune effector cells in vivo over time.

In some embodiments, the modified immune effector cells described herein demonstrate increased expression or production of pro-inflammatory immune factors compared to an unmodified immune effector cell. Examples of pro-inflammatory immune factors include cytolytic factors, such as granzyme B, perforin, and granulysin; and pro-inflammatory cytokines such as interferons (IFNα, IFNβ, IFNγ), TNFα, IL-1β, IL-12, IL-2, IL-17, CXCL8, and/or IL-6.

In some embodiments, the modified immune effector cells described herein demonstrate increased cytotoxicity against a target cell compared to an unmodified immune effector cell. In some embodiments, the modified immune effector cells demonstrate a 1, 2, 3, 4, 5, 6, 7, 8, 9, 10, 20, 30, 40, 50, 60, 70, 80, 90, 100, or more fold increase in cytotoxicity against a target cell compared to an unmodified immune cell.

Assays for measuring immune effector function are known in the art. For example, tumor infiltration can be measured by isolating tumors from a subject and determining the total number and/or phenotype of the lymphocytes present in the tumor by flow cytometry, immunohistochemistry, and/or immunofluorescence. Cell-surface receptor expression can be determined by flow cytometry, immunohistochemistry, immunofluorescence, Western blot, and/or qPCR. Cytokine and chemokine expression and production can be measured by flow cytometry, immunohistochemistry, immunofluorescence, Western blot, ELISA, and/or qPCR. Responsiveness or sensitivity to extracellular stimuli (e.g., cytokines, inhibitory ligands, or antigen) can be measured by assaying cellular proliferation and/or activation of downstream signaling pathways (e.g., phosphorylation of downstream signaling intermediates) in response to the stimuli. Cytotoxicity can be measured by target-cell lysis assays known in the art, including in vitro or ex vivo co-culture of the modified immune effector cells with target cells and in vivo murine tumor models.

IV. Methods of Producing Modified Immune Effector Cells

In some embodiments, the present disclosure provides methods for producing modified immune effector cells. In some embodiments, the methods comprise introducing a polynucleotide encoding a NR4A super-repressor or a NR4A super-repressor into a population of immune effector cells wherein the NR4A super-repressor is capable of reducing the transcriptional activity of NR4A1, NR4A2, and/or NR4A3.

The polynucleotide encoding a NR4A super-repressor or the NR4A super-repressor can be introduced into target cells in a variety of forms using a variety of delivery methods and formulations. In some embodiments, a polynucleotide encoding a NR4A super-repressor is delivered by a recombinant vector (e.g., a viral vector or plasmid). In some embodiments, a vector may also comprise a sequence encoding a signal peptide (e.g., for nuclear localization), fused to the polynucleotide encoding the NR4A super-repressor. For example, a vector may comprise a nuclear localization sequence (e.g., from SV40) fused to the polynucleotide encoding the NR4A super-repressor. In some embodiments, the introduction of the polynucleotide encoding a NR4A super-repressor or the NR4A super-repressor to the cell occurs in vitro. In some embodiments, the introduction of the polynucleotide encoding a NR4A super-repressor or the NR4A super-repressor to the cell occurs in vivo. In some embodiments, the introduction of the polynucleotide encoding a NR4A super-repressor or the NR4A super-repressor to the cell occurs ex vivo.

In some embodiments, the recombinant vector comprising a polynucleotide encoding a NR4A super-repressor described herein is a viral vector. Suitable viral vectors include, but are not limited to, viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., U.S. Pat. No. 7,078,387; Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

In some embodiments, the recombinant vector comprising a polynucleotide encoding a NR4A super-repressor described herein is a plasmid. Numerous suitable plasmid expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other plasmid vector may be used so long as it is compatible with the host cell. Depending on the cell type and NR4A super-repressor utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, a polynucleotide sequence encoding a NR4A super-repressor described herein is operably linked to a control element, e.g., a transcriptional control element, such as a promoter. The transcriptional control element may be functional in either a eukaryotic cell (e.g., a mammalian cell) or a prokaryotic cell (e.g., bacterial or archaeal cell). In some embodiments, a polynucleotide sequence encoding a NR4A super-repressor described herein is operably linked to multiple control elements that allow expression of the polynucleotide in both prokaryotic and eukaryotic cells. Depending on the cell type and NR4A super-repressor utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-1. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that are fused to the site-directed modifying polypeptide, thus resulting in a chimeric polypeptide.

In some embodiments, a polynucleotide sequence encoding a NR4A super-repressor described herein is operably linked to an inducible promoter. In some embodiments, a polynucleotide sequence encoding a NR4A super-repressor described herein is operably linked to a constitutive promoter.

Methods of introducing polynucleotides and recombinant vectors into a host cell are known in the art, and any known method can be used to introduce a polynucleotide encoding a NR4A super-repressor into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., Adv Drug Deliv Rev. 2012 Sep. 13. pii: S0169-409X(12)00283-9), microfluidics delivery methods (See e.g., International PCT Publication No. WO 2013/059343), and the like. In some embodiments, delivery via electroporation comprises mixing the cells with a polynucleotide encoding a NR4A super-repressor in a cartridge, chamber, or cuvette and applying one or more electrical impulses of defined duration and amplitude. In some embodiments, cells are mixed with a polynucleotide encoding a NR4A super-repressor in a vessel connected to a device (e.g., a pump) which feeds the mixture into a cartridge, chamber, or cuvette wherein one or more electrical impulses of defined duration and amplitude are applied, after which the cells are delivered to a second vessel.

In some embodiments, a polynucleotide encoding a NR4A super-repressor or a NR4A super-repressor described herein are introduced to a cell in a non-viral delivery vehicle, such as a transposon, a nanoparticle (e.g., a lipid nanoparticle), a liposome, an exosome, an attenuated bacterium, or a virus-like particle. In some embodiments, the vehicle is an attenuated bacterium (e.g., naturally or artificially engineered to be invasive but attenuated to prevent pathogenesis including Listeria monocytogenes, certain Salmonella strains, Bifidobacterium longum, and modified Escherichia coli), bacteria having nutritional and tissue-specific tropism to target specific cells, and bacteria having modified surface proteins to alter target cell specificity. In some embodiments, the vehicle is a genetically modified bacteriophage (e.g., engineered phages having large packaging capacity, less immunogenicity, containing mammalian plasmid maintenance sequences and having incorporated targeting ligands). In some embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In some embodiments, the vehicle is a biological liposome. For example, the biological liposome is a phospholipid-based particle derived from human cells (e.g., erythrocyte ghosts, which are red blood cells broken down into spherical structures derived from the subject and wherein tissue targeting can be achieved by attachment of various tissue or cell-specific ligands), secretory exosomes, or subject-derived membrane-bound nanovesicles (30-100 nm) of endocytic origin (e.g., can be produced from various cell types and can therefore be taken up by cells without the need for targeting ligands).

In some embodiments, the methods of modifying immune effector cells described herein comprise obtaining a population of immune effector cells from a sample. In some embodiments, a sample comprises a tissue sample, a fluid sample, a cell sample, a protein sample, or a DNA or RNA sample. In some embodiments, a tissue sample may be derived from any tissue type including, but not limited to skin, hair (including roots), bone marrow, bone, muscle, salivary gland, esophagus, stomach, small intestine (e.g., tissue from the duodenum, jejunum, or ileum), large intestine, liver, gallbladder, pancreas, lung, kidney, bladder, uterus, ovary, vagina, placenta, testes, thyroid, adrenal gland, cardiac tissue, thymus, spleen, lymph node, spinal cord, brain, eye, ear, tongue, cartilage, white adipose tissue, or brown adipose tissue. In some embodiments, a tissue sample may be derived from a cancerous, pre-cancerous, or non-cancerous tumor. In some embodiments, a fluid sample comprises buccal swabs, blood, plasma, oral mucous, vaginal mucous, peripheral blood, cord blood, saliva, semen, urine, ascites fluid, pleural fluid, spinal fluid, pulmonary lavage, tears, sweat, semen, seminal fluid, seminal plasma, prostatic fluid, pre-ejaculatory fluid (Cowper's fluid), excreta, cerebrospinal fluid, lymph, cell culture media comprising one or more populations of cells, buffered solutions comprising one or more populations of cells, and the like.

In some embodiments, the sample is processed to enrich or isolate a particular cell type, such as an immune effector cell, from the remainder of the sample. In certain embodiments, the sample is a peripheral blood sample which is then subject to leukapheresis to separate the red blood cells and platelets and to isolate lymphocytes. In some embodiments, the sample is a leukopak from which immune effector cells can be isolated or enriched. In some embodiments, the sample is a tumor sample that is further processed to isolate lymphocytes present in the tumor (i.e., to isolate tumor infiltrating lymphocytes).

In some embodiments, the isolated immune effector cells are expanded in culture to produce an expanded population of immune effector cells. One or more activating or growth factors may be added to the culture system during the expansion process. For example, in some embodiments, one or more cytokines (such as IL-2, IL-15, and/or IL-7) can be added to the culture system to enhance or promote cell proliferation and expansion. In some embodiments, one or more activating antibodies, such as an anti-CD3 antibody, may be added to the culture system to enhance or promote cell proliferation and expansion. In some embodiments, the immune effector cells may be co-cultured with feeder cells during the expansion process. In some embodiments, the methods provided herein comprise one or more expansion phases. For example, in some embodiments, the immune effector cells can be expanded after isolation from a sample, allowed to rest, and then expanded again. In some embodiments, the immune effector cells can be expanded in one set of expansion conditions followed by a second round of expansion in a second, different, set of expansion conditions. Methods for ex vivo expansion of immune cells are known in the art, for example, as described in US Patent Application Publication Nos. 20180282694 and 20170152478 and U.S. Pat. Nos. 8,383,099 and 8,034,334.

At any point during the culture and expansion process, the polynucleotide encoding a NR4A super-repressor or the NR4A super-repressor described herein can be introduced to the immune effector cells to produce a population of modified immune effector cells. In some embodiments, the polynucleotide encoding a NR4A super-repressor or the NR4A super-repressor is introduced to the population of immune effector cells immediately after enrichment from a sample. In some embodiments, the polynucleotide encoding a NR4A super-repressor or the NR4A super-repressor is introduced to the population of immune effector cells before, during, or after the one or more expansion process. In some embodiments, the polynucleotide encoding a NR4A super-repressor or the NR4A super-repressor is introduced to the population of immune effector cells immediately after enrichment from a sample or harvest from a subject, and prior to any expansion rounds. In some embodiments, the polynucleotide encoding a NR4A super-repressor or the NR4A super-repressor is introduced to the population of immune effector cells after a first round of expansion and prior to a second round of expansion. In some embodiments, the polynucleotide encoding a NR4A super-repressor or the NR4A super-repressor is introduced to the population of immune effector cells after a first and a second round of expansion.

In some embodiments, the modified immune effector cells produced by the methods described herein may be used immediately. Alternatively, the cells may be frozen at liquid nitrogen temperatures and stored for long periods of time, being thawed and capable of being reused. In such cases, the cells will usually be frozen in 10% dimethylsulfoxide (DMSO), 50% serum, 40% buffered medium, or some other such solution as is commonly used in the art to preserve cells at such freezing temperatures, and thawed in a manner as commonly known in the art for thawing frozen cultured cells.

In some embodiments, the modified immune effector cells may be cultured in vitro under various culture conditions. The cells may be expanded in culture, i.e. grown under conditions that promote their proliferation. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the regulatory T cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

V. Compositions and Kits

The term "composition" as used herein refers to a formulation of a polynucleotide encoding a NR4A super-repressor or the NR4A super-repressor or a modified immune effector cell described herein that is capable of being administered or delivered to a subject or cell. Typically, formulations include all physiologically acceptable compositions including derivatives and/or prodrugs, solvates, stereoisomers, racemates, or tautomers thereof with any physiologically acceptable carriers, diluents, and/or excipients. A "therapeutic composition" or "pharmaceutical composition" (used interchangeably herein) is a composition of a polynucleotide encoding a NR4A super-repressor or a NR4A super-repressor or a modified immune effector cell capable of being administered to a subject for the treatment of a particular disease or disorder or contacted with a cell for inhibition of transcription of one or more endogenous NR4A target genes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some embodiments, the present disclosure provides kits for carrying out a method described herein. In some embodiments, a kit can include (a) one or more polynucleotides encoding a NR4A super-repressor or (b) one or more NR4A super-repressors (c) a modified immune effector cell described herein; or (d) any combination thereof.

In some embodiments, the kits described herein further comprise one or more immune checkpoint inhibitors. Several immune checkpoint inhibitors are known in the art and have received FDA approval for the treatment of one or more cancers. For example, FDA-approved PD-L1 inhibitors include Atezolizumab (Tecentriq®, Genentech), Avelumab (Bavencio®, Pfizer), and Durvalumab (Imfinzi®, AstraZeneca); FDA-approved PD-1 inhibitors include Pembrolizumab (Keytruda®, Merck) and Nivolumab (Opdivo®, Bristol-Myers Squibb); and FDA-approved CTLA4 inhibitors include Ipilimumab (Yervoy®, Bristol-Myers Squibb). Additional inhibitory immune checkpoint molecules that may be the target of future therapeutics include A2AR, B7-H3, B7-H4, BTLA, IDO, LAG3 (e.g., BMS-986016, under development by BSM), KIR (e.g., Lirilumab, under development by BSM), TIM3, TIGIT, and VISTA.

In some embodiments, the kits described herein comprise one or more polynucleotides encoding an NR4A super-repressor or one or more NR4A super-repressor and one or more immune checkpoint inhibitors known in the art (e.g., a PD1 inhibitor, a CTLA4 inhibitor, a PDL1 inhibitor, etc.). In some embodiments, the kits described herein comprise one or more polynucleotides encoding an NR4A super-repressor or one or more NR4A super-repressor and an anti-PD1 antibody (e.g., Pembrolizumab or Nivolumab). In some embodiments, the kits described herein comprise a modified immune effector cell described herein (or population thereof) and one or more immune checkpoint inhibitors known in the art (e.g., a PD1 inhibitor, a CTLA4 inhibitor, a PDL1 inhibitor, etc.). In some embodiments, the kits described herein comprise a modified immune effector cell described herein (or population thereof) and an anti-PD1 antibody (e.g., Pembrolizumab or Nivolumab).

In some embodiments, the kit comprises one or more NR4A super-repressor or one or more polynucleotides encoding the NR4A super-repressor and a reagent for reconstituting and/or diluting the NR4A super-repressor or polynucleotide. In some embodiments, a kit comprising NR4A super-repressor or one or more polynucleotides encoding the NR4A super-repressor further comprises one or more additional reagents, where such additional reagents can be selected from: a buffer for introducing the NR4A super-repressor or polynucleotide encoding the NR4A super-repressor into a cell; a wash buffer; a control reagent; a control expression vector or RNA polynucleotide; a reagent for in vitro production of the NR4A super-repressor from DNA, and the like. Components of a kit can be in separate containers or can be combined in a single container.

In addition to above-mentioned components, in some embodiments a kit further comprises instructions for using the components of the kit to practice the methods of the present disclosure. The instructions for practicing the methods are generally recorded on a suitable recording medium. For example, the instructions may be printed on a substrate, such as paper or plastic, etc. As such, the instructions may be present in the kits as a package insert or in the labeling of the container of the kit or components thereof (i.e., associated with the packaging or sub-packaging). In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

VI. Therapeutic Methods and Applications

In some embodiments, the modified immune effector cells, NR4A super-repressors, and polynucleotides encoding NR4A super-repressors described herein may be used in a variety of therapeutic applications. For example, in some embodiments the modified immune effector cells, NR4A super-repressors, and/or polynucleotides encoding NR4A super-repressors described herein may be administered to a subject for purposes such as gene therapy, e.g. to treat a disease, for use as an antiviral, for use as an anti-pathogenic, for use as an anti-cancer therapeutic, or for biological research.

In some embodiments, the subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mice, rats, guinea pigs, hamsters, rabbits, etc.) may be used for experimental investigations.

Administration of the modified immune effector cells described herein, populations thereof, and compositions thereof can occur by injection, irrigation, inhalation, consumption, electro-osmosis, hemodialysis, iontophoresis, and other methods known in the art. In some embodiments, administration route is local or systemic. In some embodiments administration route is intraarterial, intracranial, intradermal, intraduodenal, intramammary, intrameningeal, intraperitoneal, intrathecal, intratumoral, intravenous, intravitreal, ophthalmic, parenteral, spinal, subcutaneous, ureteral, urethral, vaginal, or intrauterine.

In some embodiments, the administration route is by infusion (e.g., continuous or bolus). Examples of methods for local administration, that is, delivery to the site of injury or disease, include through an Ommaya reservoir, e.g. for intrathecal delivery (See e.g., U.S. Pat. Nos. 5,222,982 and 5,385,582, incorporated herein by reference); by bolus injection, e.g. by a syringe, e.g. into a joint; by continuous infusion, e.g. by cannulation, such as with convection (See e.g., US Patent Application Publication No. 2007-0254842, incorporated herein by reference); or by implanting a device upon which the cells have been reversibly affixed (see e.g.

US Patent Application Publication Nos. 2008-0081064 and 2009-0196903, incorporated herein by reference). In some embodiments, the administration route is by topical administration or direct injection. In some embodiments, the modified immune effector cells described herein may be provided to the subject alone or with a suitable substrate or matrix, e.g. to support their growth and/or organization in the tissue to which they are being transplanted.

In some embodiments, at least $1\times10^3$ cells are administered to a subject. In some embodiments, at least $5\times10^3$ cells, $1\times10^4$ cells, $5\times10^4$ cells, $1\times10^5$ cells, $5\times10^5$ cells, $1\times10^6$, $2\times10^6$, $3\times10^6$, $4\times10^6$, $5\times10^6$, $1\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more cells are administered to a subject. In some embodiments, between about $1\times10^7$ and about $1\times10^{12}$ cells are administered to a subject. In some embodiments, between about $1\times10^8$ and about $1\times10^{12}$ cells are administered to a subject. In some embodiments, between about $1\times10^9$ and about $1\times10^{12}$ cells are administered to a subject. In some embodiments, between about $1\times10^{10}$ and about $1\times10^{12}$ cells are administered to a subject. In some embodiments, between about $1\times10^{11}$ and about $1\times10^{12}$ cells are administered to a subject. In some embodiments, between about $1\times10^7$ and about $1\times10^{11}$ cells are administered to a subject. In some embodiments, between about $1\times10^7$ and about $1\times10^{10}$ cells are administered to a subject. In some embodiments, between about $1\times10^7$ and about $1\times10^9$ cells are administered to a subject. In some embodiments, between about $1\times10^7$ and about $1\times10^8$ cells are administered to a subject. The number of administrations of treatment to a subject may vary. In some embodiments, introducing the modified immune effector cells into the subject may be a one-time event. In some embodiments, such treatment may require an on-going series of repeated treatments. In some embodiments, multiple administrations of the modified immune effector cells may be required before an effect is observed. The exact protocols depend upon the disease or condition, the stage of the disease and parameters of the individual subject being treated.

In some embodiments, the polynucleotides encoding NR4A super-repressors or the NR4A super-repressors described herein are employed to modify transcription of NR4A target genes in vivo, such as for gene therapy or for biological research. In such embodiments, a polynucleotide encoding an NR4A super-repressor or a NR4A super-repressor may be administered directly to the subject, such as by the methods described supra. In some embodiments, the polynucleotide encoding an NR4A super-repressor or the NR4A super-repressor described herein are employed for the ex vivo or in vitro modification of a population of immune effector cells. In such embodiments, the polynucleotide encoding an NR4A super-repressor or the NR4A super-repressor described herein are administered to a sample comprising immune effector cells.

In some embodiments, the modified immune effector cells described herein are administered to a subject. In some embodiments, the modified immune effector cells described herein administered to a subject are autologous immune effector cells. The term "autologous" in this context refers to cells that have been derived from the same subject to which they are administered. For example, immune effector cells may be obtained from a subject, modified ex vivo according to the methods described herein, and then administered to the same subject in order to treat a disease. In such embodiments, the cells administered to the subject are autologous immune effector cells. In some embodiments, the modified immune effector cells, or compositions thereof, administered to a subject are allogenic immune effector cells. The term "allogenic" in this context refers to cells that have been derived from one subject and are administered to another subject. For example, immune effector cells may be obtained from a first subject, modified ex vivo according to the methods described herein and then administered to a second subject in order to treat a disease. In such embodiments, the cells administered to the subject are allogenic immune effector cells.

In some embodiments, the modified immune effector cells described herein are administered to a subject in order to treat a disease. In some embodiments, treatment comprises delivering an effective amount of a population of cells (e.g., a population of modified immune effector cells) or composition thereof to a subject in need thereof. In some embodiments, treating refers to the treatment of a disease in a mammal, e.g., in a human, including (a) inhibiting the disease, i.e., arresting disease development or preventing disease progression; (b) relieving the disease, i.e., causing regression of the disease state or relieving one or more symptoms of the disease; and (c) curing the disease, i.e., remission of one or more disease symptoms. In some embodiments, treatment may refer to a short-term (e.g., temporary and/or acute) and/or a long-term (e.g., sustained) reduction in one or more disease symptoms. In some embodiments, treatment results in an improvement or remediation of the symptoms of the disease. The improvement is an observable or measurable improvement, or may be an improvement in the general feeling of well-being of the subject.

The effective amount of a modified immune effector cell administered to a particular subject will depend on a variety of factors, several of which will differ from patient to patient including the disorder being treated and the severity of the disorder; activity of the specific agent(s) employed; the age, body weight, general health, sex and diet of the patient; the timing of administration, route of administration; the duration of the treatment; drugs used in combination; the judgment of the prescribing physician; and like factors known in the medical arts.

In some embodiments, the effective amount of a modified immune effector cell may be the number of cells required to result in at least 1, 2, 3, 4, 5, 6, 7, 8, 9, 10, 20, 30, 40, 50, 60, 70, 80, 90, 100, or more fold decrease in tumor mass or volume, decrease in the number of tumor cells, or decrease in the number of metastases. In some embodiments, the effective amount of a modified immune effector cell may be the number of cells required to achieve an increase in life expectancy, an increase in progression-free or disease-free survival, or amelioration of various physiological symptoms associated with the disease being treated. In some embodiments, an effective amount of modified immune effector cells will be at least $1 \times 10^3$ cells, for example $5 \times 10^3$ cells, $1 \times 10^4$ cells, $5 \times 10^4$ cells, $1 \times 10^5$ cells, $5 \times 10^5$ cells, $1 \times 10^6$, $2 \times 10^6$, $3 \times 10^6$, $4 \times 10^6$, $5 \times 10^6$, $1 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, or more cells.

In some embodiments, the modified immune effector cells, polynucleotides encoding an NR4A super-repressor, or NR4A super-repressors described herein may be used in the treatment of a cell-proliferative disorder, such as a cancer. Cancers that may be treated using the compositions and methods disclosed herein include cancers of the blood and solid tumors. For example, cancers that may be treated using the compositions and methods disclosed herein include, but are not limited to, adenoma, carcinoma, sarcoma, leukemia or lymphoma. In some embodiments, the cancer is chronic lymphocytic leukemia (CLL), B cell acute lymphocytic leukemia (B-ALL), acute lymphoblastic leukemia (ALL), acute myeloid leukemia (AML), non-Hodgkin's lymphoma (NHL), diffuse large cell lymphoma (DLCL), diffuse large B cell lymphoma (DLBCL), Hodgkin's lymphoma, multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma, and liver cancer.

As described above, several immune checkpoint inhibitors are currently approved for use in a variety of oncologic indications (e.g., CTLA4 inhibitors, PD1 inhibitors, PDL1 inhibitors, etc.). In some embodiments, administration of a modified immune effector cell comprising reduced expression and/or function of an endogenous target gene described herein results in an enhanced therapeutic effect (e.g., a more significant reduction in tumor growth, an increase in tumor infiltration by lymphocytes, an increase in the length of progression free survival, etc.) than is observed after treatment with an immune checkpoint inhibitor.

Further, some oncologic indications are non-responsive (i.e., are insensitive) to treatment with immune checkpoint inhibitors. Further still, some oncologic indications that are initially responsive (i.e., sensitive) to treatment with immune checkpoint inhibitors develop an inhibitor-resistant phenotype during the course of treatment. Therefore, in some embodiments, the modified immune effector cells described herein, or compositions thereof, are administered to treat a cancer that is resistant (or partially resistant) or insensitive (or partially insensitive) to treatment with one or more immune checkpoint inhibitors. In some embodiments, administration of the modified immune effector cells or compositions thereof to a subject suffering from a cancer that is resistant (or partially resistant) or insensitive (or partially insensitive) to treatment with one or more immune checkpoint inhibitors results in treatment of the cancer (e.g., reduction in tumor growth, an increase in the length of progression free survival, etc.). In some embodiments, the cancer is resistant (or partially resistant) or insensitive (or partially insensitive) to treatment with a PD1 inhibitor.

In some embodiments, the modified immune effector cells or compositions thereof are administered in combination with an immune checkpoint inhibitor. In some embodiments, administration of the modified immune effector cells in combination with the immune checkpoint inhibitor results in an enhanced therapeutic effect in a cancer that is resistant, refractory, or insensitive to treatment by an immune checkpoint inhibitor than is observed by treatment with either the modified immune effector cells or the immune checkpoint inhibitor alone. In some embodiments, administration of the modified immune effector cells in combination with the immune checkpoint inhibitor results in an enhanced therapeutic effect in a cancer that is partially resistant, partially refractory, or partially insensitive to treatment by an immune checkpoint inhibitor than is observed by treatment with either the modified immune effector cells or the immune checkpoint inhibitor alone. In some embodiments, the cancer is resistant (or partially resistant), refractory (or partially refractory), or insensitive (or partially insensitive) to treatment with a PD1 inhibitor.

In some embodiments, administration of a modified immune effector cell described herein or composition thereof in combination with an anti-PD1 antibody results in an enhanced therapeutic effect in a cancer that is resistant or insensitive to treatment by the anti-PD1 antibody alone. In some embodiments, administration of a modified immune effector cell described herein or composition thereof in combination with an anti-PD1 antibody results in an enhanced therapeutic effect in a cancer that is partially resistant or partially insensitive to treatment by the anti-PD1 antibody alone.

Cancers that demonstrate resistance or sensitivity to immune checkpoint inhibition are known in the art and can be tested in a variety of in vivo and in vitro models. For example, some melanomas are sensitive to treatment with an immune checkpoint inhibitor such as an anti-PD1 antibody and can be modeled in an in vivo B16-Ova tumor model. Further, some colorectal cancers are known to be resistant to treatment with an immune checkpoint inhibitor such as an anti-PD1 antibody and can be modeled in a PMEL/MC38-gp100 model. Further still, some lymphomas are known to be insensitive to treatment with an immune checkpoint inhibitor such as an anti-PD1 antibody and can be modeled in a various models by adoptive transfer or subcutaneous administration of lymphoma cell lines, such as Raji cells.

In some embodiments, the modified immune effector cells, polynucleotides encoding an NR4A super-repressor, or NR4A super-repressors described herein may be used in the treatment of a viral infection. In some embodiments, the virus is selected from one of adenoviruses, herpesviruses (including, for example, herpes simplex virus and Epstein Barr virus, and herpes zoster virus), poxviruses, papovaviruses, hepatitis viruses, (including, for example, hepatitis B virus and hepatitis C virus), papilloma viruses, orthomyxoviruses (including, for example, influenza A, influenza B, and influenza C), paramyxoviruses, coronaviruses, picornaviruses, reoviruses, togaviruses, flaviviruses, bunyaviridae, rhabdoviruses, rotavirus, respiratory syncitial virus, human immunodeficiency virus, or retroviruses.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

EXAMPLES

Example 1: Design of NR4A Super-Repressors

Genome-wide knock-out screens in CD8-specific T cells demonstrated that knocking out NR4A1, NR4A2, and NR4A3 drove robust tumor killing effects. All three of nuclear receptor transcription factors NR4A1, NR4A2, and NR4A3 bind as monomers to the response element NBRE, which has the sequence AAAGGTC (SEQ ID NO:46) (Wilson et al., *Science* 256: 107-110 (1992)) or as dimers to the palindromic NurRE, which has the sequence TGATATTTACCTCCAAATGCCA (SEQ ID NO:47) (Philips et al, *Molecular and Cellular Biology* 17: 5946-5951 (1997)). The dimers that bind to NurRE can be homodimers or heterodimers. The domain structure of these NR4A proteins is shown as the "wild-type" structure in FIG. 1. Transcriptional co-activators bind to the N-terminal transactivation (TAF) domain of the protein. The DNA binding domain (DBD) in the middle of the protein binds to NBRE and NurRE elements, and the ligand binding domain (LBD) at the C-terminus of the protein. No native ligands of NR4A proteins have been identified yet.

Figure 1:
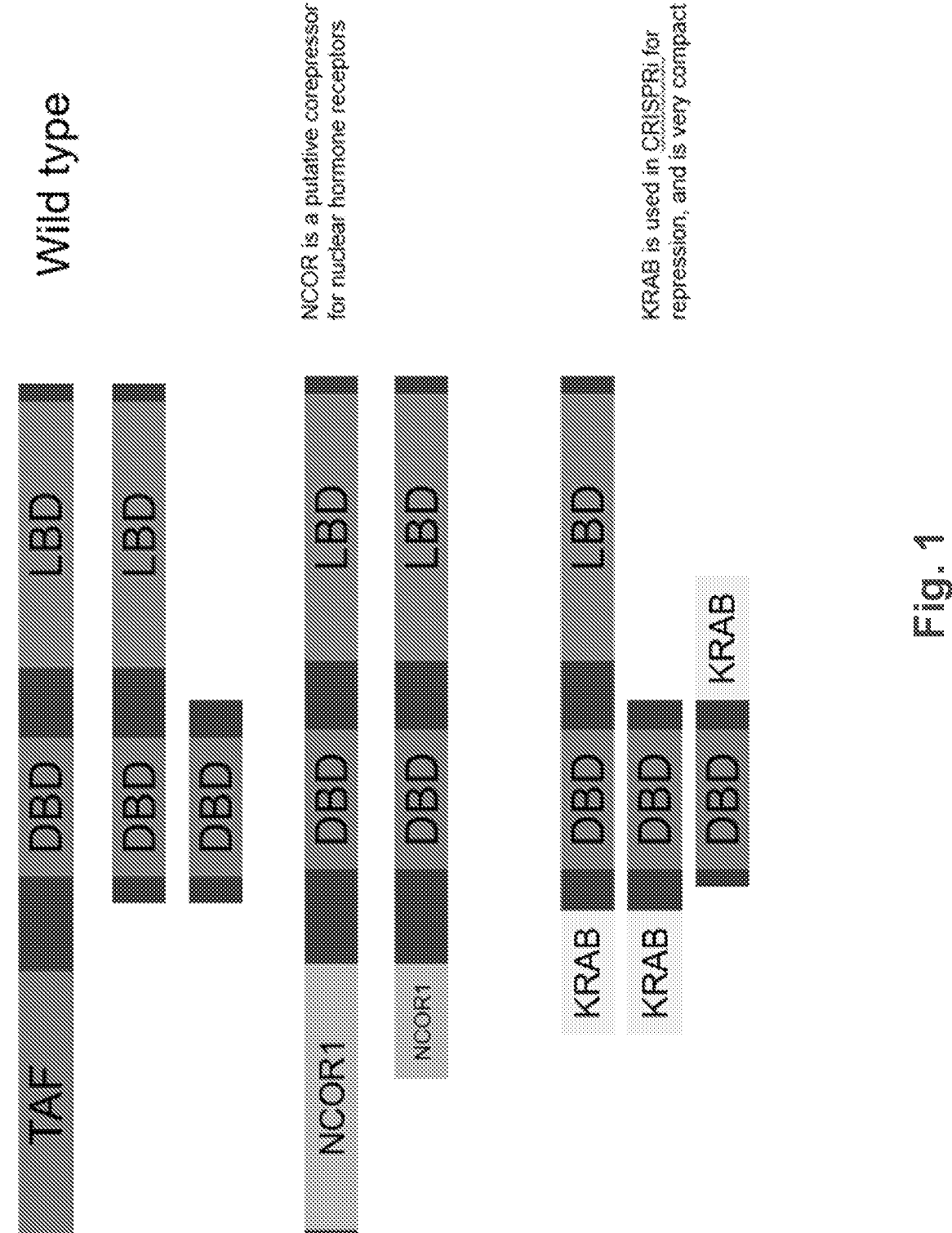
FIG. 1 depicts the domain structures of "wild-type" NR4A proteins and NR4A super-repressor proteins. The wild-type NR4A proteins contain a TAF transactivation domain, a DNA-binding domain (DBD), and a ligand-binding domain (LBD). The NR4A super-repressor proteins

Super-repressor proteins were designed using the DBD of the NR4A proteins. Exemplary super-repressor proteins are depicted in FIG. 1. For example, a dominant negative repressive effect can be obtained by removing the transactivation domain of NR4A, leaving only the DNA binding domain, and optionally the ligand binding domain. The resulting truncated factors can behave as a competitive inhibitor of transcription. The truncated factors can also be fused to repressor domains such as NCOR1 or the KRAB (Krüppel associated box) domain of Kox1. NCOR is a putative co-repressor for nuclear hormone receptors (Cher Yeo et al., *Nature Methods* 15: 611-616 (2018)). KRAB is a repressive chromatin modifier domain that has been used in CRISPR interference (CRISPRi) to increase the potency of silencing (Gilbert et al., *Cell* 154: 442-451 (2013)).

Example 2: Evaluation of NR4A Super-Repressors

A cell-based assay was designed to evaluate the ability of proteins to function as NR4A super-repressors by silencing the expression of NR4A target genes. FIG. 2 provides a schematic of the experimental setup. In brief, Jurkat cells were transfected with NurRE (5×) or NBRE (8×) Nano-luciferase reporter plasmids together with pcDNA3.1 vectors encoding potential super-repressors, and pcDNA3.1. The pcDNA3.1 was added to ensure that the total quantity of DNA in each transfection was equivalent because a reverse correlation between DNA concentration and cell survival has been observed. Firefly-Luciferase reporter plasmid (Promega) was co-transfected as an internal control. Cells were cultured overnight and stimulated with T-cell activator (Stemcell Technology)(CD3/28/2) for 6 hours. In the absence of a repressor, the stimulation results in the up-regulation of NR4A target genes, so increased nano-luciferase expression is observed. (See $7^{th}$ and $8^{th}$ bars in graphs in FIGS. 3-7.) In contrast, if the pcDNA3.1 vector encodes a protein that blocks expression of NR4A target genes, the protein will inhibit the increase in nano-luciferase expression. Luciferase activity was determined using the Nano-Glo Dual Luciferase Reporter system, according to the manufacturer's protocol.

The reporter activity was compared to Jurkat cells in which NR4A1, 2, and 3 were genetically deleted using sgRNAs against NR4A, 1, 2 and 3 (Jurkat-NR4A-TKO). To confirm successful knockdown of NR4A family members, genomic DNA was extracted from the cells, and amplicons spanning the recognition sites for the individual sgRNAs were amplified by polymerase chain reaction (PCR) and sequenced by next-generation sequencing (NGS). In cells where NR4A1, 2, and 3 were knocked down, stimulation with the tetramer did not increase luciferase activity. (See the $9^{th}$ and $10^{th}$ bars in the graphs in FIGS. 3-7.)

This assay was used to test the activity of several potential super-repressors. The results are shown in FIGS. 3-7. In each of these figures, three concentrations (0.5, 0.17, and 0.056 μg) of the NR4A super-repressors ("SR") are tested with and without T-cell activator stimulation. For comparison, the results obtained with no NR4A super-repressor and the results obtained with a triple knock out of NR4A1, NR4A2, and NR4A3 (TKO) are shown. FIG. 3 shows a construct containing only the DBD of NR4A3 inhibited the (CD3/28/2) stimulated induction of luciferase in a dose-dependent fashion from both the NurRE and NBRE elements. FIG. 4 shows the results obtained using a construct that contains both the DBD and LBD of NR4A. Although this construct also inhibited the induction of luciferase, it was not as effective as the DBD alone. FIG. 5 shows the results obtained using a construct that contains NCOR1 fused to the DBD and LBD of NR4A. This construct was even less effective at inhibiting the induction of luciferase. Accordingly, a construct containing a truncated portion of NCOR1 fused to the DBD and LBD of NR4A was assayed. The results, shown in FIG. 6, demonstrate that truncating NCOR1 increased repressor activity. FIG. 7 shows the results obtained using a construct containing the DBD of NR4A fused to the KRAB domain. This construct showed similar repressive activity as the DBD alone on the NurRE element, but it was less effective than the DBD alone on the NBRE element.

These results demonstrate that multiple constructs containing the DBD of NR4A can inhibit transcription from the NurRE and NBRE elements.

Example 3: Effect of NR4A Super-Repressors on Tumors

The effect of super-repressors on tumors can be evaluated, for example, in murine models. Naïve CD8+ T cells from Rag1-deficient mice can be transduced with a retrovirus encoding a CAR and encoding an NR4A super-repressor. As a control, the T cells can be transduced with a retrovirus only encoding the CAR. The resulting cells (e.g., $3 \times 10^6$ cells) can be adoptively transferred into Rag1-deficient mice 7 days after tumor inoculation, and tumor growth can be measured. Smaller tumor sizes in the mice receiving the T cells expressing CAR and the NR4A super-repressor as compared to the mice receiving T cells expressing only the CAR indicate that the super-repressors are effective in reducing tumor growth.

---

The invention claimed is:

1. A method of treating cancer in a subject in need thereof comprising administering to the subject an effective amount of cells comprising a polynucleotide comprising a nucleic acid encoding a polypeptide comprising a DNA-binding domain that specifically binds to both the NBRE element and the NurRE element, wherein (a) the polypeptide inhibits the activity of NR4A1, NR4A2, and NR4A3; or (b) the polypeptide is capable of inhibiting transcription of a gene operably associated with both the NBRE element and the NurRE element.

2. The method of claim 1, wherein the polypeptide does not comprise a transcription activation domain.

3. The method of claim 1, wherein the cells are T cells.

4. The method of claim 3, wherein the cells further comprise an engineered immune receptor.

5. A method of treating cancer in a subject in need thereof comprising administering to the subject an effective amount of cells comprising a polynucleotide comprising a nucleic acid encoding a polypeptide comprising a DNA-binding domain that specifically binds to both the NBRE element and the NurRE element, wherein the polypeptide does not comprise a transcription activation domain.

6. The method of claim 5, wherein the DNA-binding domain is a polypeptide comprising the amino acid sequence of the DNA-binding domain of NR4A1, NR4A2, or NR4A3.

7. The method of claim 6, wherein the DNA-binding domain comprises the amino acid sequence of the DNA-binding domain of NR4A3.

8. The method of claim 7, wherein the DNA-binding domain of NR4A3 is a polypeptide comprising the amino acid sequence of SEQ ID NO:4.

9. The method of claim 5, wherein the DNA-binding domain is a polypeptide comprising the amino acid sequence of any one of SEQ ID NOs: 4, 5, and 50-53.

10. The method of claim 5, wherein the DNA-binding domain comprises a TAL effector DNA binding domain, a zinc finger, or a DNA-binding domain from a meganuclease.

11. The method of claim 5, wherein the polypeptide further comprises the amino acid sequence of the ligand-binding domain (LBD) of NR4A1, NR4A2, or NR4A3.

12. The method of claim 5, wherein the polypeptide further comprises a dimerization domain, a transcriptional repressor domain, or a chromatin compaction domain.

13. The method of claim 5, wherein the polypeptide comprises the amino acid sequence of any one of SEQ ID NOs: 29-43.

14. The method of claim 5, wherein the polypeptide further comprises a Krüppel-associated box (KRAB) domain.

15. The method of claim 5, wherein the polypeptide further comprises NCOR1 or a fragment thereof.

16. The method of claim 5, wherein the DNA-binding domain is a polypeptide comprising the amino acid sequence of the DNA-binding domain of NR4A3.

17. The method of claim 16, wherein the DNA-binding domain of NR4A3 is a polypeptide comprising the amino acid sequence of SEQ ID NO:4.

18. The method of claim 5, wherein the cells are T cells.

19. The method of claim 18, wherein the cells further comprise an engineered immune receptor.

* * * * *

SEQUENCE LISTING

<160> NUMBER OF SEQ ID NOS: 53

<210> SEQ ID NO 1
<211> LENGTH: 598
<212> TYPE: PRT
<213> ORGANISM: Homo sapiens

<400> SEQUENCE: 1

```
Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
                20                  25                  30

Pro Thr Met Asp Leu Ala Ser Pro Glu Ala Ala Pro Ala Ala Pro Thr
            35                  40                  45

Ala Leu Pro Ser Phe Ser Thr Phe Met Asp Gly Tyr Thr Gly Glu Phe
        50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ser Ala Thr Ser Pro
                85                  90                  95

Ala Ser Ala Ser Phe Lys Phe Glu Asp Phe Gln Val Tyr Gly Cys Tyr
            100                 105                 110

Pro Gly Pro Leu Ser Gly Pro Val Asp Glu Ala Leu Ser Ser Ser Gly
        115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
        195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
```

```
                    245                 250                 255

Ser Gly Ala Pro Gly Gly Ser Glu Gly Arg Cys Ala Val Cys Gly Asp
                260                 265                 270

Asn Ala Ser Cys Gln His Tyr Gly Val Arg Thr Cys Glu Gly Cys Lys
                275                 280                 285

Gly Phe Phe Lys Arg Thr Val Gln Lys Asn Ala Lys Tyr Ile Cys Leu
    290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
                340                 345                 350

Pro Lys Gln Pro Pro Asp Ala Ser Pro Ala Asn Leu Leu Thr Ser Leu
                355                 360                 365

Val Arg Ala His Leu Asp Ser Gly Pro Ser Thr Ala Lys Leu Asp Tyr
    370                 375                 380

Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
                420                 425                 430

Ala Asp Gln Asp Leu Leu Leu Glu Ser Ala Phe Leu Glu Leu Phe Ile
                435                 440                 445

Leu Arg Leu Ala Tyr Arg Ser Lys Pro Gly Glu Gly Lys Leu Ile Phe
    450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
                500                 505                 510

Thr Asp Arg His Gly Leu Gln Glu Pro Arg Arg Val Glu Glu Leu Gln
                515                 520                 525

Asn Arg Ile Ala Ser Cys Leu Lys Glu His Val Ala Ala Val Ala Gly
    530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ile Ile Asp Lys Ile Phe
                580                 585                 590

Met Asp Thr Leu Pro Phe
        595

<210> SEQ ID NO 2
<211> LENGTH: 598
<212> TYPE: PRT
<213> ORGANISM: Homo Sapiens

<400> SEQUENCE: 2

Met Pro Cys Val Gln Ala Gln Tyr Gly Ser Ser Pro Gln Gly Ala Ser
1               5                   10                  15
```

```
Pro Ala Ser Gln Ser Tyr Ser Tyr His Ser Ser Gly Glu Tyr Ser Ser
        20                  25              30

Asp Phe Leu Thr Pro Glu Phe Val Lys Phe Ser Met Asp Leu Thr Asn
        35              40              45

Thr Glu Ile Thr Ala Thr Thr Ser Leu Pro Ser Phe Ser Thr Phe Met
    50                  55              60

Asp Asn Tyr Ser Thr Gly Tyr Asp Val Lys Pro Pro Cys Leu Tyr Gln
65                  70                  75              80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100             105             110

Met Met Pro His Ser Gly Ser Val Tyr Tyr Lys Pro Ser Ser Pro Pro
            115             120             125

Thr Pro Thr Thr Pro Gly Phe Gln Val Gln His Ser Pro Met Trp Asp
        130             135             140

Asp Pro Gly Ser Leu His Asn Phe His Gln Asn Tyr Val Ala Thr Thr
145             150             155             160

His Met Ile Glu Gln Arg Lys Thr Pro Val Ser Arg Leu Ser Leu Phe
                165             170             175

Ser Phe Lys Gln Ser Pro Pro Gly Thr Pro Val Ser Ser Cys Gln Met
            180             185             190

Arg Phe Asp Gly Pro Leu His Val Pro Met Asn Pro Glu Pro Ala Gly
            195             200             205

Ser His His Val Val Asp Gly Gln Thr Phe Ala Val Pro Asn Pro Ile
        210             215             220

Arg Lys Pro Ala Ser Met Gly Phe Pro Gly Leu Gln Ile Gly His Ala
225             230             235             240

Ser Gln Leu Leu Asp Thr Gln Val Pro Ser Pro Ser Arg Gly Ser
                245             250             255

Pro Ser Asn Glu Gly Leu Cys Ala Val Cys Gly Asp Asn Ala Ala Cys
            260             265             270

Gln His Tyr Gly Val Arg Thr Cys Glu Gly Cys Lys Gly Phe Phe Lys
            275             280             285

Arg Thr Val Gln Lys Asn Ala Lys Tyr Val Cys Leu Ala Asn Lys Asn
        290             295             300

Cys Pro Val Asp Lys Arg Arg Arg Asn Arg Cys Gln Tyr Cys Arg Phe
305             310             315             320

Gln Lys Cys Leu Ala Val Gly Met Val Lys Glu Val Val Arg Thr Asp
            325             330             335

Ser Leu Lys Gly Arg Arg Gly Arg Leu Pro Ser Lys Pro Lys Ser Pro
            340             345             350

Gln Glu Pro Ser Pro Pro Ser Pro Pro Val Ser Leu Ile Ser Ala Leu
            355             360             365

Val Arg Ala His Val Asp Ser Asn Pro Ala Met Thr Ser Leu Asp Tyr
        370             375             380

Ser Arg Phe Gln Ala Asn Pro Asp Tyr Gln Met Ser Gly Asp Asp Thr
385             390             395             400

Gln His Ile Gln Gln Phe Tyr Asp Leu Leu Thr Gly Ser Met Glu Ile
                405             410             415

Ile Arg Gly Trp Ala Glu Lys Ile Pro Gly Phe Ala Asp Leu Pro Lys
            420             425             430

Ala Asp Gln Asp Leu Leu Phe Glu Ser Ala Phe Leu Glu Leu Phe Val
```

-continued

```
              435                 440                 445
Leu Arg Leu Ala Tyr Arg Ser Asn Pro Val Glu Gly Lys Leu Ile Phe
    450                 455                 460
Cys Asn Gly Val Val Leu His Arg Leu Gln Cys Val Arg Gly Phe Gly
465                 470                 475                 480
Glu Trp Ile Asp Ser Ile Val Glu Phe Ser Ser Asn Leu Gln Asn Met
                485                 490                 495
Asn Ile Asp Ile Ser Ala Phe Ser Cys Ile Ala Ala Leu Ala Met Val
                500                 505                 510
Thr Glu Arg His Gly Leu Lys Glu Pro Lys Arg Val Glu Glu Leu Gln
                515                 520                 525
Asn Lys Ile Val Asn Cys Leu Lys Asp His Val Thr Phe Asn Asn Gly
        530                 535                 540
Gly Leu Asn Arg Pro Asn Tyr Leu Ser Lys Leu Leu Gly Lys Leu Pro
545                 550                 555                 560
Glu Leu Arg Thr Leu Cys Thr Gln Gly Leu Gln Arg Ile Phe Tyr Leu
                565                 570                 575
Lys Leu Glu Asp Leu Val Pro Pro Pro Ala Ile Ile Asp Lys Leu Phe
                580                 585                 590
Leu Asp Thr Leu Pro Phe
        595

<210> SEQ ID NO 3
<211> LENGTH: 626
<212> TYPE: PRT
<213> ORGANISM: Homo Sapiens

<400> SEQUENCE: 3

Met Pro Cys Val Gln Ala Gln Tyr Ser Pro Ser Pro Pro Gly Ser Ser
1               5                   10                  15
Tyr Ala Ala Gln Thr Tyr Ser Ser Glu Tyr Thr Thr Glu Ile Met Asn
                20                  25                  30
Pro Asp Tyr Thr Lys Leu Thr Met Asp Leu Gly Ser Thr Glu Ile Thr
            35                  40                  45
Ala Thr Ala Thr Thr Ser Leu Pro Ser Ile Ser Thr Phe Val Glu Gly
        50                  55                  60
Tyr Ser Ser Asn Tyr Glu Leu Lys Pro Ser Cys Val Tyr Gln Met Gln
65                  70                  75                  80
Arg Pro Leu Ile Lys Val Glu Glu Gly Arg Ala Pro Ser Tyr His His
                85                  90                  95
His His His His His His His His His His His Gln Gln Gln His
                100                 105                 110
Gln Gln Pro Ser Ile Pro Pro Ala Ser Ser Pro Glu Asp Glu Val Leu
        115                 120                 125
Pro Ser Thr Ser Met Tyr Phe Lys Gln Ser Pro Pro Ser Thr Pro Thr
    130                 135                 140
Thr Pro Ala Phe Pro Pro Gln Ala Gly Ala Leu Trp Asp Glu Ala Leu
145                 150                 155                 160
Pro Ser Ala Pro Gly Cys Ile Ala Pro Gly Pro Leu Leu Asp Pro Pro
                165                 170                 175
Met Lys Ala Val Pro Thr Val Ala Gly Ala Arg Phe Pro Leu Phe His
                180                 185                 190
Phe Lys Pro Ser Pro Pro His Pro Pro Ala Pro Ser Pro Ala Gly Gly
        195                 200                 205
```

-continued

```
His His Leu Gly Tyr Asp Pro Thr Ala Ala Ala Ala Leu Ser Leu Pro
    210             215                 220
```

```
Leu Gly Ala Ala Ala Ala Ala Gly Ser Gln Ala Ala Ala Leu Glu Ser
225             230                 235                 240
```

```
His Pro Tyr Gly Leu Pro Leu Ala Lys Arg Ala Ala Pro Leu Ala Phe
            245                 250                 255
```

```
Pro Pro Leu Gly Leu Thr Pro Ser Pro Thr Ala Ser Ser Leu Leu Gly
            260             265                 270
```

```
Glu Ser Pro Ser Leu Pro Ser Pro Pro Ser Arg Ser Ser Ser Ser Gly
        275                 280                 285
```

```
Glu Gly Thr Cys Ala Val Cys Gly Asp Asn Ala Ala Cys Gln His Tyr
    290             295                 300
```

```
Gly Val Arg Thr Cys Glu Gly Cys Lys Gly Phe Phe Lys Arg Thr Val
305             310                 315                 320
```

```
Gln Lys Asn Ala Lys Tyr Val Cys Leu Ala Asn Lys Asn Cys Pro Val
                325                 330                 335
```

```
Asp Lys Arg Arg Arg Asn Arg Cys Gln Tyr Cys Arg Phe Gln Lys Cys
            340                 345                 350
```

```
Leu Ser Val Gly Met Val Lys Glu Val Val Arg Thr Asp Ser Leu Lys
        355                 360                 365
```

```
Gly Arg Arg Gly Arg Leu Pro Ser Lys Pro Lys Ser Pro Leu Gln Gln
    370             375                 380
```

```
Glu Pro Ser Gln Pro Ser Pro Ser Pro Pro Ile Cys Met Met Asn
385                 390                 395                 400
```

```
Ala Leu Val Arg Ala Leu Thr Asp Ser Thr Pro Arg Asp Leu Asp Tyr
            405                 410                 415
```

```
Ser Arg Tyr Cys Pro Thr Asp Gln Ala Ala Ala Gly Thr Asp Ala Glu
            420                 425                 430
```

```
His Val Gln Gln Phe Tyr Asn Leu Leu Thr Ala Ser Ile Asp Val Ser
        435                 440                 445
```

```
Arg Ser Trp Ala Glu Lys Ile Pro Gly Phe Thr Asp Leu Pro Lys Glu
    450                 455                 460
```

```
Asp Gln Thr Leu Leu Ile Glu Ser Ala Phe Leu Glu Leu Phe Val Leu
465                 470                 475                 480
```

```
Arg Leu Ser Ile Arg Ser Asn Thr Ala Glu Asp Lys Phe Val Phe Cys
            485                 490                 495
```

```
Asn Gly Leu Val Leu His Arg Leu Gln Cys Leu Arg Gly Phe Gly Glu
            500                 505                 510
```

```
Trp Leu Asp Ser Ile Lys Asp Phe Ser Leu Asn Leu Gln Ser Leu Asn
            515                 520                 525
```

```
Leu Asp Ile Gln Ala Leu Ala Cys Leu Ser Ala Leu Ser Met Ile Thr
    530                 535                 540
```

```
Glu Arg His Gly Leu Lys Glu Pro Lys Arg Val Glu Glu Leu Cys Asn
545                 550                 555                 560
```

```
Lys Ile Thr Ser Ser Leu Lys Asp His Gln Ser Lys Gly Gln Ala Leu
                565                 570                 575
```

```
Glu Pro Thr Glu Ser Lys Val Leu Gly Ala Leu Val Glu Leu Arg Lys
            580                 585                 590
```

```
Ile Cys Thr Leu Gly Leu Gln Arg Ile Phe Tyr Leu Lys Leu Glu Asp
            595                 600                 605
```

```
Leu Val Ser Pro Pro Ser Ile Ile Asp Lys Leu Phe Leu Asp Thr Leu
    610                 615                 620
```

```
Pro Phe
```

-continued

625

<210> SEQ ID NO 4
<211> LENGTH: 92
<212> TYPE: PRT
<213> ORGANISM: Artificial Sequence
<220> FEATURE:
<223> OTHER INFORMATION: synthetic peptide

<400> SEQUENCE: 4

Gly Glu Gly Thr Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
                20                  25                  30

Val Gln Lys Asn Ala Lys Tyr Val Cys Leu Ala Asn Lys Asn Cys Pro
        35                  40                  45

Val Asp Lys Arg Arg Arg Asn Arg Cys Gln Tyr Cys Arg Phe Gln Lys
    50                  55                  60

Cys Leu Ser Val Gly Met Val Lys Glu Val Val Arg Thr Asp Ser Leu
65                  70                  75                  80

Lys Gly Arg Arg Gly Arg Leu Pro Ser Lys Pro Lys
                85                  90

<210> SEQ ID NO 5
<211> LENGTH: 93
<212> TYPE: PRT
<213> ORGANISM: Artificial Sequence
<220> FEATURE:
<223> OTHER INFORMATION: synthetic peptide

<400> SEQUENCE: 5

Gly Glu Gly Thr Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
                20                  25                  30

Val Gln Lys Asn Ala Lys Tyr Val Cys Leu Ala Asn Lys Asn Cys Pro
        35                  40                  45

Val Asp Lys Arg Arg Arg Asn Arg Cys Gln Tyr Cys Arg Phe Gln Lys
    50                  55                  60

Cys Leu Ser Val Gly Met Val Lys Glu Val Val Arg Thr Asp Ser Leu
65                  70                  75                  80

Lys Gly Arg Arg Gly Arg Leu Pro Ser Lys Pro Lys Ser
                85                  90

<210> SEQ ID NO 6
<211> LENGTH: 232
<212> TYPE: PRT
<213> ORGANISM: Artificial Sequence
<220> FEATURE:
<223> OTHER INFORMATION: synthetic peptide

<400> SEQUENCE: 6

Met Leu Thr Pro Glu Gln Val Val Ala Ile Ala Ser Asn His Gly Gly
1               5                   10                  15

Lys Gln Ala Leu Glu Thr Val Gln Arg Leu Leu Pro Val Cys Gln Ala
                20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Cys Gln
    50                  55                  60

```
Ala His Gly Leu Thr Pro Glu Gln Val Val Ala Ile Ala Ser Asn Gly
65                  70                  75                  80

Gly Gly Lys Gln Ala Leu Glu Thr Val Gln Arg Leu Leu Pro Val Cys
                85                  90                  95

Gln Ala His Gly Leu Thr Pro Glu Gln Val Val Ala Ile Ala Ser Asn
            100                 105                 110

Ile Gly Gly Lys Gln Ala Leu Glu Thr Val Gln Arg Leu Leu Pro Val
        115                 120                 125

Cys Gln Ala His Gly Leu Thr Pro Glu Gln Val Val Ala Ile Ala Ser
    130                 135                 140

Asn Gly Gly Gly Lys Gln Ala Leu Glu Thr Val Gln Arg Leu Leu Pro
145                 150                 155                 160

Val Cys Gln Ala His Gly Leu Thr Pro Glu Gln Val Val Ala Ile Ala
                165                 170                 175

Ser Asn Gly Gly Gly Lys Gln Ala Leu Glu Thr Val Gln Arg Leu Leu
            180                 185                 190

Pro Val Cys Gln Ala His Gly Leu Thr Pro Glu Gln Val Val Ala Ile
        195                 200                 205

Ala Ser Asn Gly Gly Gly Lys Gln Ala Leu Glu Thr Val Gln Arg Leu
    210                 215                 220

Leu Pro Val Cys Gln Ala His Gly
225                 230

<210> SEQ ID NO 7
<211> LENGTH: 232
<212> TYPE: PRT
<213> ORGANISM: Artificial Sequence
<220> FEATURE:
<223> OTHER INFORMATION: synthetic peptide

<400> SEQUENCE: 7

Met Leu Thr Pro Glu Gln Val Val Ala Ile Ala Ser Asn His Gly Gly
1               5                   10                  15

Lys Gln Ala Leu Glu Thr Val Gln Arg Leu Leu Pro Val Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Cys Gln
    50                  55                  60

Ala His Gly Leu Thr Pro Glu Gln Val Val Ala Ile Ala Ser Asn Gly
65                  70                  75                  80

Gly Gly Lys Gln Ala Leu Glu Thr Val Gln Arg Leu Leu Pro Val Cys
                85                  90                  95

Gln Ala His Gly Leu Thr Pro Glu Gln Val Val Ala Ile Ala Ser Asn
            100                 105                 110

Ile Gly Gly Lys Gln Ala Leu Glu Thr Val Gln Arg Leu Leu Pro Val
        115                 120                 125

Cys Gln Ala His Gly Leu Thr Pro Glu Gln Val Val Ala Ile Ala Ser
    130                 135                 140

Asn Gly Gly Gly Lys Gln Ala Leu Glu Thr Val Gln Arg Leu Leu Pro
145                 150                 155                 160

Val Cys Gln Ala His Gly Leu Thr Pro Glu Gln Val Val Ala Ile Ala
                165                 170                 175

Ser Asn Gly Gly Gly Lys Gln Ala Leu Glu Thr Val Gln Arg Leu Leu
            180                 185                 190
```

Pro Val Cys Gln Ala His Gly Leu Thr Pro Glu Gln Val Val Ala Ile
        195                 200                 205

Ala Ser Asn Gly Gly Gly Lys Gln Ala Leu Glu Thr Val Gln Arg Leu
        210                 215                 220

Leu Pro Val Cys Gln Ala His Gly
225                 230

<210> SEQ ID NO 8
<211> LENGTH: 231
<212> TYPE: PRT
<213> ORGANISM: Artificial Sequence
<220> FEATURE:
<223> OTHER INFORMATION: synthetic peptide

<400> SEQUENCE: 8

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Cys Gln Ala His
        20                  25                  30

Gly Leu Thr Pro Glu Gln Val Val Ala Ile Ala Ser Asn Ile Gly Gly
        35                  40                  45

Lys Gln Ala Leu Glu Thr Val Gln Arg Leu Leu Pro Val Cys Gln Ala
        50                  55                  60

His Gly Leu Thr Pro Glu Gln Val Val Ala Ile Ala Ser Asn Ile Gly
65                  70                  75                  80

Gly Lys Gln Ala Leu Glu Thr Val Gln Arg Leu Leu Pro Val Cys Gln
                85                  90                  95

Ala His Gly Leu Thr Pro Glu Gln Val Val Ala Ile Ala Ser Asn Gly
        100                 105                 110

Gly Gly Lys Gln Ala Leu Glu Thr Val Gln Arg Leu Leu Pro Val Cys
        115                 120                 125

Gln Ala His Gly Leu Thr Pro Glu Gln Val Val Ala Ile Ala Ser Asn
        130                 135                 140

His Gly Gly Lys Gln Ala Leu Glu Thr Val Gln Arg Leu Leu Pro Val
145                 150                 155                 160

Cys Gln Ala His Gly Leu Thr Pro Glu Gln Val Val Ala Ile Ala Ser
                165                 170                 175

His Asp Gly Gly Lys Gln Ala Leu Glu Thr Val Gln Arg Leu Leu Pro
        180                 185                 190

Val Cys Gln Ala His Gly Leu Thr Pro Glu Gln Val Val Ala Ile Ala
        195                 200                 205

Ser His Asp Gly Gly Lys Gln Ala Leu Glu Thr Val Gln Arg Leu Leu
        210                 215                 220

Pro Val Cys Gln Ala His Gly
225                 230

<210> SEQ ID NO 9
<211> LENGTH: 12
<212> TYPE: PRT
<213> ORGANISM: Artificial Sequence
<220> FEATURE:
<223> OTHER INFORMATION: synthetic peptide

<400> SEQUENCE: 9

Gly Gly Ser Gly Asn Gly Glu Gly Ser Gly Asn Gly
1               5                   10

-continued

```
<210> SEQ ID NO 10
<211> LENGTH: 475
<212> TYPE: PRT
<213> ORGANISM: Artificial Sequence
<220> FEATURE:
<223> OTHER INFORMATION: synthetic peptide

<400> SEQUENCE: 10

Met Leu Thr Pro Glu Gln Val Val Ala Ile Ala Ser Asn His Gly Gly
1               5                   10                  15

Lys Gln Ala Leu Glu Thr Val Gln Arg Leu Leu Pro Val Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Cys Gln
    50                  55                  60

Ala His Gly Leu Thr Pro Glu Gln Val Val Ala Ile Ala Ser Asn Gly
65                  70                  75                  80

Gly Gly Lys Gln Ala Leu Glu Thr Val Gln Arg Leu Leu Pro Val Cys
                85                  90                  95

Gln Ala His Gly Leu Thr Pro Glu Gln Val Val Ala Ile Ala Ser Asn
                100                 105                 110

Ile Gly Gly Lys Gln Ala Leu Glu Thr Val Gln Arg Leu Leu Pro Val
            115                 120                 125

Cys Gln Ala His Gly Leu Thr Pro Glu Gln Val Val Ala Ile Ala Ser
        130                 135                 140

Asn Gly Gly Gly Lys Gln Ala Leu Glu Thr Val Gln Arg Leu Leu Pro
145                 150                 155                 160

Val Cys Gln Ala His Gly Leu Thr Pro Glu Gln Val Val Ala Ile Ala
                165                 170                 175

Ser Asn Gly Gly Gly Lys Gln Ala Leu Glu Thr Val Gln Arg Leu Leu
            180                 185                 190

Pro Val Cys Gln Ala His Gly Leu Thr Pro Glu Gln Val Val Ala Ile
            195                 200                 205

Ala Ser Asn Gly Gly Gly Lys Gln Ala Leu Glu Thr Val Gln Arg Leu
    210                 215                 220

Leu Pro Val Cys Gln Ala His Gly Gly Gly Ser Gly Asn Gly Glu Gly
225                 230                 235                 240

Ser Gly Asn Gly Leu Thr Pro Glu Gln Val Val Ala Ile Ala Ser Asn
                245                 250                 255

Ile Gly Gly Lys Gln Ala Leu Glu Thr Val Gln Arg Leu Leu Pro Val
            260                 265                 270

Cys Gln Ala His Gly Leu Thr Pro Glu Gln Val Val Ala Ile Ala Ser
        275                 280                 285

Asn Ile Gly Gly Lys Gln Ala Leu Glu Thr Val Gln Arg Leu Leu Pro
    290                 295                 300

Val Cys Gln Ala His Gly Leu Thr Pro Glu Gln Val Val Ala Ile Ala
305                 310                 315                 320

Ser Asn Ile Gly Gly Lys Gln Ala Leu Glu Thr Val Gln Arg Leu Leu
            325                 330                 335

Pro Val Cys Gln Ala His Gly Leu Thr Pro Glu Gln Val Val Ala Ile
            340                 345                 350

Ala Ser Asn Gly Gly Gly Lys Gln Ala Leu Glu Thr Val Gln Arg Leu
        355                 360                 365

Leu Pro Val Cys Gln Ala His Gly Leu Thr Pro Glu Gln Val Val Ala
```

```
        370                375                380

Ile Ala Ser Asn His Gly Gly Lys Gln Ala Leu Glu Thr Val Gln Arg
385                390                395                400

Leu Leu Pro Val Cys Gln Ala His Gly Leu Thr Pro Glu Gln Val Val
                405                410                415

Ala Ile Ala Ser His Asp Gly Gly Lys Gln Ala Leu Glu Thr Val Gln
                420                425                430

Arg Leu Leu Pro Val Cys Gln Ala His Gly Leu Thr Pro Glu Gln Val
        435                440                445

Val Ala Ile Ala Ser His Asp Gly Gly Lys Gln Ala Leu Glu Thr Val
        450                455                460

Gln Arg Leu Leu Pro Val Cys Gln Ala His Gly
465                470                475
```

```
<210> SEQ ID NO 11
<211> LENGTH: 92
<212> TYPE: PRT
<213> ORGANISM: Artificial Sequence
<220> FEATURE:
<223> OTHER INFORMATION: synthetic peptide

<400> SEQUENCE: 11

Leu Glu Pro Gly Glu Lys Pro Tyr Lys Cys Pro Glu Cys Gly Lys Ser
1                5                10                15

Phe Ser Gln Ser Gly Asn Leu Thr Glu His Gln Arg Thr His Thr Gly
                20                25                30

Glu Lys Pro Tyr Lys Cys Pro Glu Cys Gly Lys Ser Phe Ser Thr Ser
        35                40                45

Gly His Leu Val Arg His Gln Arg Thr His Thr Gly Glu Lys Pro Tyr
    50                55                60

Lys Cys Pro Glu Cys Gly Lys Ser Phe Ser Gln Arg Ala Asn Leu Arg
65                70                75                80

Ala His Gln Arg Thr His Thr Gly Lys Lys Thr Ser
                85                90
```

```
<210> SEQ ID NO 12
<211> LENGTH: 64
<212> TYPE: PRT
<213> ORGANISM: Artificial Sequence
<220> FEATURE:
<223> OTHER INFORMATION: synthetic peptide

<400> SEQUENCE: 12

Leu Glu Pro Gly Glu Lys Pro Tyr Lys Cys Pro Glu Cys Gly Lys Ser
1                5                10                15

Phe Ser His Lys Asn Ala Leu Gln Asn His Gln Arg Thr His Thr Gly
                20                25                30

Glu Lys Pro Tyr Lys Cys Pro Glu Cys Gly Lys Ser Phe Ser Thr Ser
        35                40                45

Gly Asn Leu Val Arg His Gln Arg Thr His Thr Gly Lys Lys Thr Ser
    50                55                60
```

```
<210> SEQ ID NO 13
<211> LENGTH: 64
<212> TYPE: PRT
<213> ORGANISM: Artificial Sequence
<220> FEATURE:
<223> OTHER INFORMATION: synthetic peptide

<400> SEQUENCE: 13
```

```
Leu Glu Pro Gly Glu Lys Pro Tyr Lys Cys Pro Glu Cys Gly Lys Ser
1               5                   10                  15

Phe Ser Asp Cys Arg Asp Leu Ala Arg His Gln Arg Thr His Thr Gly
            20                  25                  30

Glu Lys Pro Tyr Lys Cys Pro Glu Cys Gly Lys Ser Phe Ser Thr Thr
        35                  40                  45

Gly Asn Leu Thr Val His Gln Arg Thr His Thr Gly Lys Lys Thr Ser
    50                  55                  60
```

<210> SEQ ID NO 14
<211> LENGTH: 140
<212> TYPE: PRT
<213> ORGANISM: Artificial Sequence
<220> FEATURE:
<223> OTHER INFORMATION: synthetic peptide

<400> SEQUENCE: 14

```
Leu Glu Pro Gly Glu Lys Pro Tyr Lys Cys Pro Glu Cys Gly Lys Ser
1               5                   10                  15

Phe Ser His Lys Asn Ala Leu Gln Asn His Gln Arg Thr His Thr Gly
            20                  25                  30

Glu Lys Pro Tyr Lys Cys Pro Glu Cys Gly Lys Ser Phe Ser Thr Ser
        35                  40                  45

Gly Asn Leu Val Arg His Gln Arg Thr His Thr Gly Lys Lys Thr Ser
    50                  55                  60

Gly Gly Ser Gly Asn Gly Glu Gly Ser Gly Asn Gly Leu Glu Pro Gly
65                  70                  75                  80

Glu Lys Pro Tyr Lys Cys Pro Glu Cys Gly Lys Ser Phe Ser Asp Cys
                85                  90                  95

Arg Asp Leu Ala Arg His Gln Arg Thr His Thr Gly Glu Lys Pro Tyr
            100                 105                 110

Lys Cys Pro Glu Cys Gly Lys Ser Phe Ser Thr Thr Gly Asn Leu Thr
        115                 120                 125

Val His Gln Arg Thr His Thr Gly Lys Lys Thr Ser
    130                 135                 140
```

<210> SEQ ID NO 15
<211> LENGTH: 246
<212> TYPE: PRT
<213> ORGANISM: Artificial Sequence
<220> FEATURE:
<223> OTHER INFORMATION: synthetic peptide

<400> SEQUENCE: 15

```
Pro Leu Gln Gln Glu Pro Ser Gln Pro Ser Pro Pro Ser Pro Pro Ile
1               5                   10                  15

Cys Met Met Asn Ala Leu Val Arg Ala Leu Thr Asp Ser Thr Pro Arg
            20                  25                  30

Asp Leu Asp Tyr Ser Arg Tyr Cys Pro Thr Asp Gln Ala Ala Ala Gly
            35                  40                  45

Thr Asp Ala Glu His Val Gln Gln Phe Tyr Asn Leu Leu Thr Ala Ser
    50                  55                  60

Ile Asp Val Ser Arg Ser Trp Ala Glu Lys Ile Pro Gly Phe Thr Asp
65                  70                  75                  80

Leu Pro Lys Glu Asp Gln Thr Leu Leu Ile Glu Ser Ala Phe Leu Glu
                85                  90                  95

Leu Phe Val Leu Arg Leu Ser Ile Arg Ser Asn Thr Ala Glu Asp Lys
```

-continued

```
                   100                 105                 110
Phe Val Phe Cys Asn Gly Leu Val Leu His Arg Leu Gln Cys Leu Arg
            115                 120                 125

Gly Phe Gly Glu Trp Leu Asp Ser Ile Lys Asp Phe Ser Leu Asn Leu
    130                 135                 140

Gln Ser Leu Asn Leu Asp Ile Gln Ala Leu Ala Cys Leu Ser Ala Leu
145                 150                 155                 160

Ser Met Ile Thr Glu Arg His Gly Leu Lys Glu Pro Lys Arg Val Glu
                165                 170                 175

Glu Leu Cys Asn Lys Ile Thr Ser Ser Leu Lys Asp His Gln Ser Lys
            180                 185                 190

Gly Gln Ala Leu Glu Pro Thr Glu Ser Lys Val Leu Gly Ala Leu Val
    195                 200                 205

Glu Leu Arg Lys Ile Cys Thr Leu Gly Leu Gln Arg Ile Phe Tyr Leu
    210                 215                 220

Lys Leu Glu Asp Leu Val Ser Pro Pro Ser Ile Ile Asp Lys Leu Phe
225                 230                 235                 240

Leu Asp Thr Leu Pro Phe
                245
```

```
<210> SEQ ID NO 16
<211> LENGTH: 247
<212> TYPE: PRT
<213> ORGANISM: Artificial Sequence
<220> FEATURE:
<223> OTHER INFORMATION: synthetic peptide

<400> SEQUENCE: 16

Ser Pro Leu Gln Gln Glu Pro Ser Gln Pro Ser Pro Ser Pro Pro
1               5                   10                  15

Ile Cys Met Met Asn Ala Leu Val Arg Ala Leu Thr Asp Ser Thr Pro
                20                  25                  30

Arg Asp Leu Asp Tyr Ser Arg Tyr Cys Pro Thr Asp Gln Ala Ala Ala
            35                  40                  45

Gly Thr Asp Ala Glu His Val Gln Gln Phe Tyr Asn Leu Leu Thr Ala
    50                  55                  60

Ser Ile Asp Val Ser Arg Ser Trp Ala Glu Lys Ile Pro Gly Phe Thr
65                  70                  75                  80

Asp Leu Pro Lys Glu Asp Gln Thr Leu Leu Ile Glu Ser Ala Phe Leu
                85                  90                  95

Glu Leu Phe Val Leu Arg Leu Ser Ile Arg Ser Asn Thr Ala Glu Asp
            100                 105                 110

Lys Phe Val Phe Cys Asn Gly Leu Val Leu His Arg Leu Gln Cys Leu
            115                 120                 125

Arg Gly Phe Gly Glu Trp Leu Asp Ser Ile Lys Asp Phe Ser Leu Asn
    130                 135                 140

Leu Gln Ser Leu Asn Leu Asp Ile Gln Ala Leu Ala Cys Leu Ser Ala
145                 150                 155                 160

Leu Ser Met Ile Thr Glu Arg His Gly Leu Lys Glu Pro Lys Arg Val
                165                 170                 175

Glu Glu Leu Cys Asn Lys Ile Thr Ser Ser Leu Lys Asp His Gln Ser
            180                 185                 190

Lys Gly Gln Ala Leu Glu Pro Thr Glu Ser Lys Val Leu Gly Ala Leu
    195                 200                 205

Val Glu Leu Arg Lys Ile Cys Thr Leu Gly Leu Gln Arg Ile Phe Tyr
```

```
        210             215             220

Leu Lys Leu Glu Asp Leu Val Ser Pro Pro Ser Ile Ile Asp Lys Leu
225                 230             235             240

Phe Leu Asp Thr Leu Pro Phe
                245

<210> SEQ ID NO 17
<211> LENGTH: 23
<212> TYPE: PRT
<213> ORGANISM: Artificial Sequence
<220> FEATURE:
<223> OTHER INFORMATION: synthetic peptide

<400> SEQUENCE: 17

Met Asp Tyr Lys Asp His Asp Gly Asp Tyr Lys Asp His Asp Ile Asp
1               5               10              15

Tyr Lys Asp Asp Asp Asp Lys
                20

<210> SEQ ID NO 18
<211> LENGTH: 72
<212> TYPE: PRT
<213> ORGANISM: Artificial Sequence
<220> FEATURE:
<223> OTHER INFORMATION: synthetic peptide

<400> SEQUENCE: 18

Met Asp Ala Lys Ser Leu Thr Ala Trp Ser Arg Thr Leu Val Thr Phe
1               5               10              15

Lys Asp Val Phe Val Asp Phe Thr Arg Glu Glu Trp Lys Leu Leu Asp
                20              25              30

Thr Ala Gln Gln Ile Val Tyr Arg Asn Val Met Leu Glu Asn Tyr Lys
            35              40              45

Asn Leu Val Ser Leu Gly Tyr Gln Leu Thr Lys Pro Asp Val Ile Leu
    50              55              60

Arg Leu Glu Lys Gly Glu Glu Pro
65                  70

<210> SEQ ID NO 19
<211> LENGTH: 71
<212> TYPE: PRT
<213> ORGANISM: Artificial Sequence
<220> FEATURE:
<223> OTHER INFORMATION: synthetic peptide

<400> SEQUENCE: 19

Met Asn Met Asn Gly Leu Met Glu Asp Pro Met Lys Val Tyr Lys Asp
1               5               10              15

Arg Gln Phe Met Asn Val Trp Thr Asp His Glu Lys Glu Ile Phe Lys
                20              25              30

Asp Lys Phe Ile Gln His Pro Lys Asn Phe Gly Leu Ile Ala Ser Tyr
            35              40              45

Leu Glu Arg Lys Ser Val Pro Asp Cys Val Leu Tyr Tyr Tyr Leu Thr
    50              55              60

Lys Lys Asn Glu Asn Tyr Lys
65                  70

<210> SEQ ID NO 20
<211> LENGTH: 312
<212> TYPE: PRT
<213> ORGANISM: Artificial Sequence
```

-continued

```
<220> FEATURE:
<223> OTHER INFORMATION: synthetic peptide

<400> SEQUENCE: 20

Met Ser Ser Ser Gly Tyr Pro Pro Asn Gln Gly Ala Phe Ser Thr Glu
1               5                   10                  15

Gln Ser Arg Tyr Pro Pro His Ser Val Gln Tyr Thr Phe Pro Asn Thr
            20                  25                  30

Arg His Gln Gln Glu Phe Ala Val Pro Asp Tyr Arg Ser Ser His Leu
        35                  40                  45

Glu Val Ser Gln Ala Ser Gln Leu Leu Gln Gln Gln Gln Gln Gln Gln
    50                  55                  60

Leu Arg Arg Arg Pro Ser Leu Leu Ser Glu Phe His Pro Gly Ser Asp
65                  70                  75                  80

Arg Pro Gln Glu Arg Arg Thr Ser Tyr Glu Pro Phe His Pro Gly Pro
                85                  90                  95

Ser Pro Val Asp His Asp Ser Leu Glu Ser Lys Arg Pro Arg Leu Glu
            100                 105                 110

Gln Val Ser Asp Ser His Phe Gln Arg Val Ser Ala Ala Val Leu Pro
        115                 120                 125

Leu Val His Pro Leu Pro Glu Gly Leu Arg Ala Ser Ala Asp Ala Lys
    130                 135                 140

Lys Asp Pro Ala Phe Gly Gly Lys His Glu Ala Pro Ser Ser Pro Ile
145                 150                 155                 160

Ser Gly Gln Pro Cys Gly Asp Asp Gln Asn Ala Ser Pro Ser Lys Leu
                165                 170                 175

Ser Lys Glu Glu Leu Ile Gln Ser Met Asp Arg Val Asp Arg Glu Ile
            180                 185                 190

Ala Lys Val Glu Gln Gln Ile Leu Lys Leu Lys Lys Lys Gln Gln Gln
            195                 200                 205

Leu Glu Glu Glu Ala Ala Lys Pro Pro Glu Pro Glu Lys Pro Val Ser
    210                 215                 220

Pro Pro Pro Val Glu Gln Lys His Arg Ser Ile Val Gln Ile Ile Tyr
225                 230                 235                 240

Asp Glu Asn Arg Lys Lys Ala Glu Glu Ala His Lys Ile Phe Glu Gly
                245                 250                 255

Leu Gly Pro Lys Val Glu Leu Pro Leu Tyr Asn Gln Pro Ser Asp Thr
                260                 265                 270

Lys Val Tyr His Glu Asn Ile Lys Thr Asn Gln Val Met Arg Lys Lys
            275                 280                 285

Leu Ile Leu Phe Phe Lys Arg Arg Asn His Ala Arg Lys Gln Arg Glu
    290                 295                 300

Gln Lys Ile Cys Gln Arg Tyr Asp
305                 310

<210> SEQ ID NO 21
<211> LENGTH: 21
<212> TYPE: PRT
<213> ORGANISM: Artificial Sequence
<220> FEATURE:
<223> OTHER INFORMATION: synthetic peptide

<400> SEQUENCE: 21

Gly Ser Gly Glu Gly Arg Gly Ser Leu Leu Thr Cys Gly Asp Val Glu
1               5                   10                  15

Glu Asn Pro Gly Pro
```

-continued
```
              20

<210> SEQ ID NO 22
<211> LENGTH: 9
<212> TYPE: PRT
<213> ORGANISM: Artificial Sequence
<220> FEATURE:
<223> OTHER INFORMATION: synthetic peptide

<400> SEQUENCE: 22

Pro Ala Ala Lys Arg Val Lys Leu Asp
1               5

<210> SEQ ID NO 23
<211> LENGTH: 36
<212> TYPE: PRT
<213> ORGANISM: Artificial Sequence
<220> FEATURE:
<223> OTHER INFORMATION: synthetic peptide

<400> SEQUENCE: 23

Ser Gln Asp Pro Ala Ala Ala Met Lys Gln Leu Glu Asp Lys Val Glu
1               5                  10                  15

Glu Leu Leu Ser Lys Asn Tyr His Leu Glu Asn Glu Val Ala Arg Leu
            20                  25                  30

Thr Lys Leu Val
        35

<210> SEQ ID NO 24
<211> LENGTH: 228
<212> TYPE: PRT
<213> ORGANISM: Artificial Sequence
<220> FEATURE:
<223> OTHER INFORMATION: synthetic peptide

<400> SEQUENCE: 24

Met Thr Met Gly Asp Lys Lys Ser Pro Thr Arg Pro Lys Arg Gln Ala
1               5                  10                  15

Lys Pro Ala Ala Asp Glu Gly Phe Trp Asp Cys Ser Val Cys Thr Phe
            20                  25                  30

Arg Asn Ser Ala Glu Ala Phe Lys Cys Ser Ile Cys Asp Val Arg Lys
        35                  40                  45

Gly Thr Ser Thr Arg Lys Pro Arg Ile Asn Ser Gln Leu Val Ala Gln
    50                  55                  60

Gln Val Ala Gln Gln Tyr Ala Thr Pro Pro Pro Lys Lys Glu Lys
65                  70                  75                  80

Lys Glu Lys Val Glu Lys Gln Asp Lys Glu Lys Pro Glu Lys Asp Lys
                85                  90                  95

Glu Ile Ser Pro Ser Val Thr Lys Lys Asn Thr Asn Lys Lys Thr Lys
            100                 105                 110

Pro Lys Ser Asp Ile Leu Lys Asp Pro Pro Ser Glu Ala Asn Ser Ile
        115                 120                 125

Gln Ser Ala Asn Ala Thr Thr Lys Thr Ser Glu Thr Asn His Thr Ser
    130                 135                 140

Arg Pro Arg Leu Lys Asn Val Asp Arg Ser Thr Ala Gln Gln Leu Ala
145                 150                 155                 160

Val Thr Val Gly Asn Val Thr Val Ile Ile Thr Asp Phe Lys Glu Lys
                165                 170                 175

Thr Arg Ser Ser Ser Thr Ser Ser Ser Thr Val Thr Ser Ser Ala Gly
            180                 185                 190
```

-continued

```
Ser Glu Gln Gln Asn Gln Ser Ser Ser Gly Ser Glu Ser Thr Asp Lys
        195                 200                 205

Gly Ser Ser Arg Ser Ser Thr Pro Lys Gly Asp Met Ser Ala Val Asn
    210                 215                 220

Asp Glu Ser Phe
225

<210> SEQ ID NO 25
<211> LENGTH: 4
<212> TYPE: PRT
<213> ORGANISM: Artificial Sequence
<220> FEATURE:
<223> OTHER INFORMATION: synthetic peptide

<400> SEQUENCE: 25

Gly Gly Ser Gly
1

<210> SEQ ID NO 26
<211> LENGTH: 9
<212> TYPE: PRT
<213> ORGANISM: Artificial Sequence
<220> FEATURE:
<223> OTHER INFORMATION: synthetic peptide

<400> SEQUENCE: 26

Gly Gly Ser Gly Asn Gly Gly Ser Gly
1               5

<210> SEQ ID NO 27
<211> LENGTH: 12
<212> TYPE: PRT
<213> ORGANISM: Artificial Sequence
<220> FEATURE:
<223> OTHER INFORMATION: synthetic peptide

<400> SEQUENCE: 27

Gly Gly Ser Gly Asn Gly Glu Gly Ser Gly Asn Gly
1               5                   10

<210> SEQ ID NO 28
<211> LENGTH: 15
<212> TYPE: PRT
<213> ORGANISM: Artificial Sequence
<220> FEATURE:
<223> OTHER INFORMATION: synthetic peptide

<400> SEQUENCE: 28

Gly Ser Glu Thr Pro Gly Thr Ser Glu Ser Ala Thr Pro Glu Ser
1               5                   10                  15

<210> SEQ ID NO 29
<211> LENGTH: 124
<212> TYPE: PRT
<213> ORGANISM: Artificial Sequence
<220> FEATURE:
<223> OTHER INFORMATION: synthetic peptide

<400> SEQUENCE: 29

Met Asp Tyr Lys Asp His Asp Gly Asp Tyr Lys Asp His Asp Ile Asp
1               5                   10                  15

Tyr Lys Asp Asp Asp Asp Lys Gly Gly Ser Gly Asn Gly Gly Ser Gly
            20                  25                  30

Gly Glu Gly Thr Cys Ala Val Cys Gly Asp Asn Ala Ala Cys Gln His
```

-continued

```
              35                    40                    45
Tyr Gly Val Arg Thr Cys Glu Gly Cys Lys Gly Phe Phe Lys Arg Thr
    50                    55                    60
Val Gln Lys Asn Ala Lys Tyr Val Cys Leu Ala Asn Lys Asn Cys Pro
65                    70                    75                    80
Val Asp Lys Arg Arg Arg Asn Arg Cys Gln Tyr Cys Arg Phe Gln Lys
                  85                    90                    95
Cys Leu Ser Val Gly Met Val Lys Glu Val Val Arg Thr Asp Ser Leu
              100                   105                   110
Lys Gly Arg Arg Gly Arg Leu Pro Ser Lys Pro Lys
          115                   120
```

```
<210> SEQ ID NO 30
<211> LENGTH: 371
<212> TYPE: PRT
<213> ORGANISM: Artificial Sequence
<220> FEATURE:
<223> OTHER INFORMATION: synthetic peptide

<400> SEQUENCE: 30

Met Asp Tyr Lys Asp His Asp Gly Asp Tyr Lys Asp His Asp Ile Asp
1                 5                    10                   15
Tyr Lys Asp Asp Asp Asp Lys Gly Gly Ser Gly Asn Gly Gly Ser Gly
                  20                   25                   30
Gly Glu Gly Thr Cys Ala Val Cys Gly Asp Asn Ala Ala Cys Gln His
              35                    40                    45
Tyr Gly Val Arg Thr Cys Glu Gly Cys Lys Gly Phe Phe Lys Arg Thr
    50                    55                    60
Val Gln Lys Asn Ala Lys Tyr Val Cys Leu Ala Asn Lys Asn Cys Pro
65                    70                    75                    80
Val Asp Lys Arg Arg Arg Asn Arg Cys Gln Tyr Cys Arg Phe Gln Lys
                  85                    90                    95
Cys Leu Ser Val Gly Met Val Lys Glu Val Val Arg Thr Asp Ser Leu
              100                   105                   110
Lys Gly Arg Arg Gly Arg Leu Pro Ser Lys Pro Lys Ser Pro Leu Gln
          115                   120                   125
Gln Glu Pro Ser Gln Pro Ser Pro Ser Pro Pro Ile Cys Met Met
      130                   135                   140
Asn Ala Leu Val Arg Ala Leu Thr Asp Ser Thr Pro Arg Asp Leu Asp
145                   150                   155                   160
Tyr Ser Arg Tyr Cys Pro Thr Asp Gln Ala Ala Ala Gly Thr Asp Ala
              165                   170                   175
Glu His Val Gln Gln Phe Tyr Asn Leu Leu Thr Ala Ser Ile Asp Val
              180                   185                   190
Ser Arg Ser Trp Ala Glu Lys Ile Pro Gly Phe Thr Asp Leu Pro Lys
          195                   200                   205
Glu Asp Gln Thr Leu Leu Ile Glu Ser Ala Phe Leu Glu Leu Phe Val
      210                   215                   220
Leu Arg Leu Ser Ile Arg Ser Asn Thr Ala Glu Asp Lys Phe Val Phe
225                   230                   235                   240
Cys Asn Gly Leu Val Leu His Arg Leu Gln Cys Leu Arg Gly Phe Gly
                  245                   250                   255
Glu Trp Leu Asp Ser Ile Lys Asp Phe Ser Leu Asn Leu Gln Ser Leu
              260                   265                   270
Asn Leu Asp Ile Gln Ala Leu Ala Cys Leu Ser Ala Leu Ser Met Ile
```

-continued 275                    280                    285

Thr Glu Arg His Gly Leu Lys Glu Pro Lys Arg Val Glu Glu Leu Cys
    290                    295                    300

Asn Lys Ile Thr Ser Ser Leu Lys Asp His Gln Ser Lys Gly Gln Ala
305                    310                    315                    320

Leu Glu Pro Thr Glu Ser Lys Val Leu Gly Ala Leu Val Glu Leu Arg
                    325                    330                    335

Lys Ile Cys Thr Leu Gly Leu Gln Arg Ile Phe Tyr Leu Lys Leu Glu
                    340                    345                    350

Asp Leu Val Ser Pro Pro Ser Ile Ile Asp Lys Leu Phe Leu Asp Thr
                    355                    360                    365

Leu Pro Phe
    370

<210> SEQ ID NO 31
<211> LENGTH: 212
<212> TYPE: PRT
<213> ORGANISM: Artificial Sequence
<220> FEATURE:
<223> OTHER INFORMATION: synthetic peptide

<400> SEQUENCE: 31

Met Asp Tyr Lys Asp His Asp Gly Asp Tyr Lys Asp His Asp Ile Asp
1                    5                    10                    15

Tyr Lys Asp Asp Asp Lys Gly Gly Ser Gly Asn Gly Gly Ser Gly
                    20                    25                    30

Gly Glu Gly Thr Cys Ala Val Cys Gly Asp Asn Ala Ala Cys Gln His
                    35                    40                    45

Tyr Gly Val Arg Thr Cys Glu Gly Cys Lys Gly Phe Phe Lys Arg Thr
    50                    55                    60

Val Gln Lys Asn Ala Lys Tyr Val Cys Leu Ala Asn Lys Asn Cys Pro
65                    70                    75                    80

Val Asp Lys Arg Arg Arg Asn Arg Cys Gln Tyr Cys Arg Phe Gln Lys
                    85                    90                    95

Cys Leu Ser Val Gly Met Val Lys Glu Val Val Arg Thr Asp Ser Leu
                    100                    105                    110

Lys Gly Arg Arg Gly Arg Leu Pro Ser Lys Pro Lys Ser Gly Ser Glu
                    115                    120                    125

Thr Pro Gly Thr Ser Glu Ser Ala Thr Pro Glu Ser Met Asp Ala Lys
    130                    135                    140

Ser Leu Thr Ala Trp Ser Arg Thr Leu Val Thr Phe Lys Asp Val Phe
145                    150                    155                    160

Val Asp Phe Thr Arg Glu Glu Trp Lys Leu Leu Asp Thr Ala Gln Gln
                    165                    170                    175

Ile Val Tyr Arg Asn Val Met Leu Glu Asn Tyr Lys Asn Leu Val Ser
                    180                    185                    190

Leu Gly Tyr Gln Leu Thr Lys Pro Asp Val Ile Leu Arg Leu Glu Lys
                    195                    200                    205

Gly Glu Glu Pro
    210

<210> SEQ ID NO 32
<211> LENGTH: 212
<212> TYPE: PRT
<213> ORGANISM: Artificial Sequence
<220> FEATURE:
<223> OTHER INFORMATION: synthetic peptide

```
<400> SEQUENCE: 32

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
            20                  25                  30

Thr Ala Gln Gln Ile Val Tyr Arg Asn Val Met Leu Glu Asn Tyr Lys
        35                  40                  45

Asn Leu Val Ser Leu Gly Tyr Gln Leu Thr Lys Pro Asp Val Ile Leu
    50                  55                  60

Arg Leu Glu Lys Gly Glu Glu Pro Gly Ser Glu Thr Pro Gly Thr Ser
65                  70                  75                  80

Glu Ser Ala Thr Pro Glu Ser Met Asp Tyr Lys Asp His Asp Gly Asp
                85                  90                  95

Tyr Lys Asp His Asp Ile Asp Tyr Lys Asp Asp Asp Asp Lys Gly Gly
            100                 105                 110

Ser Gly Asn Gly Gly Ser Gly Gly Glu Gly Thr Cys Ala Val Cys Gly
        115                 120                 125

Asp Asn Ala Ala Cys Gln His Tyr Gly Val Arg Thr Cys Glu Gly Cys
    130                 135                 140

Lys Gly Phe Phe Lys Arg Thr Val Gln Lys Asn Ala Lys Tyr Val Cys
145                 150                 155                 160

Leu Ala Asn Lys Asn Cys Pro Val Asp Lys Arg Arg Arg Asn Arg Cys
                165                 170                 175

Gln Tyr Cys Arg Phe Gln Lys Cys Leu Ser Val Gly Met Val Lys Glu
            180                 185                 190

Val Val Arg Thr Asp Ser Leu Lys Gly Arg Arg Gly Arg Leu Pro Ser
            195                 200                 205

Lys Pro Lys Ser
        210

<210> SEQ ID NO 33
<211> LENGTH: 458
<212> TYPE: PRT
<213> ORGANISM: Artificial Sequence
<220> FEATURE:
<223> OTHER INFORMATION: synthetic peptide

<400> SEQUENCE: 33

Met Asn Met Asn Gly Leu Met Glu Asp Pro Met Lys Val Tyr Lys Asp
1               5                   10                  15

Arg Gln Phe Met Asn Val Trp Thr Asp His Glu Lys Glu Ile Phe Lys
            20                  25                  30

Asp Lys Phe Ile Gln His Pro Lys Asn Phe Gly Leu Ile Ala Ser Tyr
        35                  40                  45

Leu Glu Arg Lys Ser Val Pro Asp Cys Val Leu Tyr Tyr Tyr Leu Thr
    50                  55                  60

Lys Lys Asn Glu Asn Tyr Lys Ser Gly Ser Glu Thr Pro Gly Thr Ser
65                  70                  75                  80

Glu Ser Ala Thr Pro Glu Ser Met Asp Tyr Lys Asp His Asp Gly Asp
                85                  90                  95

Tyr Lys Asp His Asp Ile Asp Tyr Lys Asp Asp Asp Asp Lys Gly Gly
            100                 105                 110

Ser Gly Asn Gly Gly Ser Gly Gly Glu Gly Thr Cys Ala Val Cys Gly
        115                 120                 125
```

-continued

```
Asp Asn Ala Ala Cys Gln His Tyr Gly Val Arg Thr Cys Glu Gly Cys
    130                 135                 140

Lys Gly Phe Phe Lys Arg Thr Val Gln Lys Asn Ala Lys Tyr Val Cys
145                 150                 155                 160

Leu Ala Asn Lys Asn Cys Pro Val Asp Lys Arg Arg Arg Asn Arg Cys
                165                 170                 175

Gln Tyr Cys Arg Phe Gln Lys Cys Leu Ser Val Gly Met Val Lys Glu
                180                 185                 190

Val Val Arg Thr Asp Ser Leu Lys Gly Arg Arg Gly Arg Leu Pro Ser
                195                 200                 205

Lys Pro Lys Ser Pro Leu Gln Gln Glu Pro Ser Gln Pro Ser Pro Pro
    210                 215                 220

Ser Pro Pro Ile Cys Met Met Asn Ala Leu Val Arg Ala Leu Thr Asp
225                 230                 235                 240

Ser Thr Pro Arg Asp Leu Asp Tyr Ser Arg Tyr Cys Pro Thr Asp Gln
                245                 250                 255

Ala Ala Ala Gly Thr Asp Ala Glu His Val Gln Gln Phe Tyr Asn Leu
                260                 265                 270

Leu Thr Ala Ser Ile Asp Val Ser Arg Ser Trp Ala Glu Lys Ile Pro
                275                 280                 285

Gly Phe Thr Asp Leu Pro Lys Glu Asp Gln Thr Leu Leu Ile Glu Ser
    290                 295                 300

Ala Phe Leu Glu Leu Phe Val Leu Arg Leu Ser Ile Arg Ser Asn Thr
305                 310                 315                 320

Ala Glu Asp Lys Phe Val Phe Cys Asn Gly Leu Val Leu His Arg Leu
                325                 330                 335

Gln Cys Leu Arg Gly Phe Gly Glu Trp Leu Asp Ser Ile Lys Asp Phe
                340                 345                 350

Ser Leu Asn Leu Gln Ser Leu Asn Leu Asp Ile Gln Ala Leu Ala Cys
    355                 360                 365

Leu Ser Ala Leu Ser Met Ile Thr Glu Arg His Gly Leu Lys Glu Pro
    370                 375                 380

Lys Arg Val Glu Glu Leu Cys Asn Lys Ile Thr Ser Ser Leu Lys Asp
385                 390                 395                 400

His Gln Ser Lys Gly Gln Ala Leu Glu Pro Thr Glu Ser Lys Val Leu
                405                 410                 415

Gly Ala Leu Val Glu Leu Arg Lys Ile Cys Thr Leu Gly Leu Gln Arg
                420                 425                 430

Ile Phe Tyr Leu Lys Leu Glu Asp Leu Val Ser Pro Pro Ser Ile Ile
                435                 440                 445

Asp Lys Leu Phe Leu Asp Thr Leu Pro Phe
    450                 455
```

```
<210> SEQ ID NO 34
<211> LENGTH: 459
<212> TYPE: PRT
<213> ORGANISM: Artificial Sequence
<220> FEATURE:
<223> OTHER INFORMATION: synthetic peptide

<400> SEQUENCE: 34

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
                20                  25                  30
```

```
Thr Ala Gln Gln Ile Val Tyr Arg Asn Val Met Leu Glu Asn Tyr Lys
        35                  40                  45

Asn Leu Val Ser Leu Gly Tyr Gln Leu Thr Lys Pro Asp Val Ile Leu
        50                  55                  60

Arg Leu Glu Lys Gly Glu Glu Pro Ser Gly Ser Glu Thr Pro Gly Thr
65                  70                  75                  80

Ser Glu Ser Ala Thr Pro Glu Ser Met Asp Tyr Lys Asp His Asp Gly
                85                  90                  95

Asp Tyr Lys Asp His Asp Ile Asp Tyr Lys Asp Asp Asp Lys Gly
                100                 105                 110

Gly Ser Gly Asn Gly Gly Ser Gly Gly Glu Gly Thr Cys Ala Val Cys
        115                 120                 125

Gly Asp Asn Ala Ala Cys Gln His Tyr Gly Val Arg Thr Cys Glu Gly
        130                 135                 140

Cys Lys Gly Phe Phe Lys Arg Thr Val Gln Lys Asn Ala Lys Tyr Val
145                 150                 155                 160

Cys Leu Ala Asn Lys Asn Cys Pro Val Asp Lys Arg Arg Arg Asn Arg
                165                 170                 175

Cys Gln Tyr Cys Arg Phe Gln Lys Cys Leu Ser Val Gly Met Val Lys
                180                 185                 190

Glu Val Val Arg Thr Asp Ser Leu Lys Gly Arg Arg Gly Arg Leu Pro
        195                 200                 205

Ser Lys Pro Lys Ser Pro Leu Gln Gln Glu Pro Ser Gln Pro Ser Pro
        210                 215                 220

Pro Ser Pro Pro Ile Cys Met Met Asn Ala Leu Val Arg Ala Leu Thr
225                 230                 235                 240

Asp Ser Thr Pro Arg Asp Leu Asp Tyr Ser Arg Tyr Cys Pro Thr Asp
                245                 250                 255

Gln Ala Ala Ala Gly Thr Asp Ala Glu His Val Gln Gln Phe Tyr Asn
                260                 265                 270

Leu Leu Thr Ala Ser Ile Asp Val Ser Arg Ser Trp Ala Glu Lys Ile
        275                 280                 285

Pro Gly Phe Thr Asp Leu Pro Lys Glu Asp Gln Thr Leu Leu Ile Glu
        290                 295                 300

Ser Ala Phe Leu Glu Leu Phe Val Leu Arg Leu Ser Ile Arg Ser Asn
305                 310                 315                 320

Thr Ala Glu Asp Lys Phe Val Phe Cys Asn Gly Leu Val Leu His Arg
                325                 330                 335

Leu Gln Cys Leu Arg Gly Phe Gly Glu Trp Leu Asp Ser Ile Lys Asp
                340                 345                 350

Phe Ser Leu Asn Leu Gln Ser Leu Asn Leu Asp Ile Gln Ala Leu Ala
        355                 360                 365

Cys Leu Ser Ala Leu Ser Met Ile Thr Glu Arg His Gly Leu Lys Glu
        370                 375                 380

Pro Lys Arg Val Glu Glu Leu Cys Asn Lys Ile Thr Ser Ser Leu Lys
385                 390                 395                 400

Asp His Gln Ser Lys Gly Gln Ala Leu Glu Pro Thr Glu Ser Lys Val
                405                 410                 415

Leu Gly Ala Leu Val Glu Leu Arg Lys Ile Cys Thr Leu Gly Leu Gln
        420                 425                 430

Arg Ile Phe Tyr Leu Lys Leu Glu Asp Leu Val Ser Pro Pro Ser Ile
        435                 440                 445

Ile Asp Lys Leu Phe Leu Asp Thr Leu Pro Phe
```

-continued

```
              450                 455

<210> SEQ ID NO 35
<211> LENGTH: 699
<212> TYPE: PRT
<213> ORGANISM: Artificial Sequence
<220> FEATURE:
<223> OTHER INFORMATION: synthetic peptide

<400> SEQUENCE: 35

Met Ser Ser Ser Gly Tyr Pro Pro Asn Gln Gly Ala Phe Ser Thr Glu
1               5                   10                  15

Gln Ser Arg Tyr Pro Pro His Ser Val Gln Tyr Thr Phe Pro Asn Thr
            20                  25                  30

Arg His Gln Gln Glu Phe Ala Val Pro Asp Tyr Arg Ser Ser His Leu
        35                  40                  45

Glu Val Ser Gln Ala Ser Gln Leu Leu Gln Gln Gln Gln Gln Gln Gln
    50                  55                  60

Leu Arg Arg Arg Pro Ser Leu Leu Ser Glu Phe His Pro Gly Ser Asp
65                  70                  75                  80

Arg Pro Gln Glu Arg Arg Thr Ser Tyr Glu Pro Phe His Pro Gly Pro
                85                  90                  95

Ser Pro Val Asp His Asp Ser Leu Glu Ser Lys Arg Pro Arg Leu Glu
            100                 105                 110

Gln Val Ser Asp Ser His Phe Gln Arg Val Ser Ala Ala Val Leu Pro
            115                 120                 125

Leu Val His Pro Leu Pro Glu Gly Leu Arg Ala Ser Ala Asp Ala Lys
        130                 135                 140

Lys Asp Pro Ala Phe Gly Gly Lys His Glu Ala Pro Ser Ser Pro Ile
145                 150                 155                 160

Ser Gly Gln Pro Cys Gly Asp Asp Gln Asn Ala Ser Pro Ser Lys Leu
                165                 170                 175

Ser Lys Glu Glu Leu Ile Gln Ser Met Asp Arg Val Asp Arg Glu Ile
            180                 185                 190

Ala Lys Val Glu Gln Gln Ile Leu Lys Leu Lys Lys Lys Gln Gln Gln
            195                 200                 205

Leu Glu Glu Glu Ala Ala Lys Pro Pro Glu Pro Glu Lys Pro Val Ser
        210                 215                 220

Pro Pro Pro Val Glu Gln Lys His Arg Ser Ile Val Gln Ile Ile Tyr
225                 230                 235                 240

Asp Glu Asn Arg Lys Lys Ala Glu Glu Ala His Lys Ile Phe Glu Gly
                245                 250                 255

Leu Gly Pro Lys Val Glu Leu Pro Leu Tyr Asn Gln Pro Ser Asp Thr
            260                 265                 270

Lys Val Tyr His Glu Asn Ile Lys Thr Asn Gln Val Met Arg Lys Lys
            275                 280                 285

Leu Ile Leu Phe Phe Lys Arg Arg Asn His Ala Arg Lys Gln Arg Glu
        290                 295                 300

Gln Lys Ile Cys Gln Arg Tyr Asp Ser Gly Ser Glu Thr Pro Gly Thr
305                 310                 315                 320

Ser Glu Ser Ala Thr Pro Glu Ser Met Asp Tyr Lys Asp His Asp Gly
                325                 330                 335

Asp Tyr Lys Asp His Asp Ile Asp Tyr Lys Asp Asp Asp Asp Lys Gly
            340                 345                 350

Gly Ser Gly Asn Gly Gly Ser Gly Gly Glu Gly Thr Cys Ala Val Cys
```

```
             355                 360                 365

Gly Asp Asn Ala Ala Cys Gln His Tyr Gly Val Arg Thr Cys Glu Gly
    370                 375                 380

Cys Lys Gly Phe Phe Lys Arg Thr Val Gln Lys Asn Ala Lys Tyr Val
385                 390                 395                 400

Cys Leu Ala Asn Lys Asn Cys Pro Val Asp Lys Arg Arg Arg Asn Arg
                405                 410                 415

Cys Gln Tyr Cys Arg Phe Gln Lys Cys Leu Ser Val Gly Met Val Lys
            420                 425                 430

Glu Val Val Arg Thr Asp Ser Leu Lys Gly Arg Arg Gly Arg Leu Pro
            435                 440                 445

Ser Lys Pro Lys Ser Pro Leu Gln Gln Glu Pro Ser Gln Pro Ser Pro
    450                 455                 460

Pro Ser Pro Pro Ile Cys Met Met Asn Ala Leu Val Arg Ala Leu Thr
465                 470                 475                 480

Asp Ser Thr Pro Arg Asp Leu Asp Tyr Ser Arg Tyr Cys Pro Thr Asp
                485                 490                 495

Gln Ala Ala Ala Gly Thr Asp Ala Glu His Val Gln Gln Phe Tyr Asn
                500                 505                 510

Leu Leu Thr Ala Ser Ile Asp Val Ser Arg Ser Trp Ala Glu Lys Ile
            515                 520                 525

Pro Gly Phe Thr Asp Leu Pro Lys Glu Asp Gln Thr Leu Leu Ile Glu
    530                 535                 540

Ser Ala Phe Leu Glu Leu Phe Val Leu Arg Leu Ser Ile Arg Ser Asn
545                 550                 555                 560

Thr Ala Glu Asp Lys Phe Val Phe Cys Asn Gly Leu Val Leu His Arg
                565                 570                 575

Leu Gln Cys Leu Arg Gly Phe Gly Glu Trp Leu Asp Ser Ile Lys Asp
            580                 585                 590

Phe Ser Leu Asn Leu Gln Ser Leu Asn Leu Asp Ile Gln Ala Leu Ala
            595                 600                 605

Cys Leu Ser Ala Leu Ser Met Ile Thr Glu Arg His Gly Leu Lys Glu
    610                 615                 620

Pro Lys Arg Val Glu Glu Leu Cys Asn Lys Ile Thr Ser Ser Leu Lys
625                 630                 635                 640

Asp His Gln Ser Lys Gly Gln Ala Leu Glu Pro Thr Glu Ser Lys Val
                645                 650                 655

Leu Gly Ala Leu Val Glu Leu Arg Lys Ile Cys Thr Leu Gly Leu Gln
                660                 665                 670

Arg Ile Phe Tyr Leu Lys Leu Glu Asp Leu Val Ser Pro Pro Ser Ile
            675                 680                 685

Ile Asp Lys Leu Phe Leu Asp Thr Leu Pro Phe
    690                 695

<210> SEQ ID NO 36
<211> LENGTH: 360
<212> TYPE: PRT
<213> ORGANISM: Artificial Sequence
<220> FEATURE:
<223> OTHER INFORMATION: synthetic peptide

<400> SEQUENCE: 36

Gly Glu Gly Thr Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
```

-continued

```
                20                  25                  30

Val Gln Lys Asn Ala Lys Tyr Val Cys Leu Ala Asn Lys Asn Cys Pro
            35                  40                  45

Val Asp Lys Arg Arg Arg Asn Arg Cys Gln Tyr Cys Arg Phe Gln Lys
        50                  55                  60

Cys Leu Ser Val Gly Met Val Lys Glu Val Val Arg Thr Asp Ser Leu
65                  70                  75                  80

Lys Gly Arg Arg Gly Arg Leu Pro Ser Lys Pro Lys Gly Ser Gly Glu
                85                  90                  95

Gly Arg Gly Ser Leu Leu Thr Cys Gly Asp Val Glu Glu Asn Pro Gly
            100                 105                 110

Pro Ser Pro Leu Gln Gln Glu Pro Ser Gln Pro Ser Pro Pro Ser Pro
            115                 120                 125

Pro Ile Cys Met Met Asn Ala Leu Val Arg Ala Leu Thr Asp Ser Thr
            130                 135                 140

Pro Arg Asp Leu Asp Tyr Ser Arg Tyr Cys Pro Thr Asp Gln Ala Ala
145                 150                 155                 160

Ala Gly Thr Asp Ala Glu His Val Gln Gln Phe Tyr Asn Leu Leu Thr
                165                 170                 175

Ala Ser Ile Asp Val Ser Arg Ser Trp Ala Glu Lys Ile Pro Gly Phe
                180                 185                 190

Thr Asp Leu Pro Lys Glu Asp Gln Thr Leu Leu Ile Glu Ser Ala Phe
                195                 200                 205

Leu Glu Leu Phe Val Leu Arg Leu Ser Ile Arg Ser Asn Thr Ala Glu
        210                 215                 220

Asp Lys Phe Val Phe Cys Asn Gly Leu Val Leu His Arg Leu Gln Cys
225                 230                 235                 240

Leu Arg Gly Phe Gly Glu Trp Leu Asp Ser Ile Lys Asp Phe Ser Leu
                245                 250                 255

Asn Leu Gln Ser Leu Asn Leu Asp Ile Gln Ala Leu Ala Cys Leu Ser
                260                 265                 270

Ala Leu Ser Met Ile Thr Glu Arg His Gly Leu Lys Glu Pro Lys Arg
                275                 280                 285

Val Glu Glu Leu Cys Asn Lys Ile Thr Ser Ser Leu Lys Asp His Gln
        290                 295                 300

Ser Lys Gly Gln Ala Leu Glu Pro Thr Glu Ser Lys Val Leu Gly Ala
305                 310                 315                 320

Leu Val Glu Leu Arg Lys Ile Cys Thr Leu Gly Leu Gln Arg Ile Phe
                325                 330                 335

Tyr Leu Lys Leu Glu Asp Leu Val Ser Pro Pro Ser Ile Ile Asp Lys
            340                 345                 350

Leu Phe Leu Asp Thr Leu Pro Phe
            355                 360

<210> SEQ ID NO 37
<211> LENGTH: 105
<212> TYPE: PRT
<213> ORGANISM: Artificial Sequence
<220> FEATURE:
<223> OTHER INFORMATION: synthetic peptide

<400> SEQUENCE: 37

Leu Glu Pro Gly Glu Lys Pro Tyr Lys Cys Pro Glu Cys Gly Lys Ser
1               5                   10                  15

Phe Ser Gln Ser Gly Asn Leu Thr Glu His Gln Arg Thr His Thr Gly
```

-continued

```
                20               25               30

Glu Lys Pro Tyr Lys Cys Pro Glu Cys Gly Lys Ser Phe Ser Thr Ser
            35               40               45

Gly His Leu Val Arg His Gln Arg Thr His Thr Gly Glu Lys Pro Tyr
    50               55               60

Lys Cys Pro Glu Cys Gly Lys Ser Phe Ser Gln Arg Ala Asn Leu Arg
65               70               75               80

Ala His Gln Arg Thr His Thr Gly Lys Lys Thr Ser Gly Gly Ser Gly
            85               90               95

Pro Ala Ala Lys Arg Val Lys Leu Asp
            100              105
```

<210> SEQ ID NO 38
<211> LENGTH: 153
<212> TYPE: PRT
<213> ORGANISM: Artificial Sequence
<220> FEATURE:
<223> OTHER INFORMATION: synthetic peptide

<400> SEQUENCE: 38

```
Leu Glu Pro Gly Glu Lys Pro Tyr Lys Cys Pro Glu Cys Gly Lys Ser
1               5                10               15

Phe Ser His Lys Asn Ala Leu Gln Asn His Gln Arg Thr His Thr Gly
            20               25               30

Glu Lys Pro Tyr Lys Cys Pro Glu Cys Gly Lys Ser Phe Ser Thr Ser
            35               40               45

Gly Asn Leu Val Arg His Gln Arg Thr His Thr Gly Lys Lys Thr Ser
    50               55               60

Gly Gly Ser Gly Asn Gly Glu Gly Ser Gly Asn Gly Leu Glu Pro Gly
65               70               75               80

Glu Lys Pro Tyr Lys Cys Pro Glu Cys Gly Lys Ser Phe Ser Asp Cys
            85               90               95

Arg Asp Leu Ala Arg His Gln Arg Thr His Thr Gly Glu Lys Pro Tyr
            100              105              110

Lys Cys Pro Glu Cys Gly Lys Ser Phe Ser Thr Thr Gly Asn Leu Thr
            115              120              125

Val His Gln Arg Thr His Thr Gly Lys Lys Thr Ser Gly Gly Ser Gly
    130              135              140

Pro Ala Ala Lys Arg Val Lys Leu Asp
145              150
```

<210> SEQ ID NO 39
<211> LENGTH: 245
<212> TYPE: PRT
<213> ORGANISM: Artificial Sequence
<220> FEATURE:
<223> OTHER INFORMATION: synthetic peptide

<400> SEQUENCE: 39

```
Met Leu Thr Pro Glu Gln Val Val Ala Ile Ala Ser Asn His Gly Gly
1               5                10               15

Lys Gln Ala Leu Glu Thr Val Gln Arg Leu Leu Pro Val Cys Gln Ala
            20               25               30

His Gly Leu Thr Pro Glu Gln Val Val Ala Ile Ala Ser Asn Ile Gly
            35               40               45

Gly Lys Gln Ala Leu Glu Thr Val Gln Arg Leu Leu Pro Val Cys Gln
    50               55               60
```

-continued

```
Ala His Gly Leu Thr Pro Glu Gln Val Val Ala Ile Ala Ser Asn Gly
65                  70                  75                  80

Gly Gly Lys Gln Ala Leu Glu Thr Val Gln Arg Leu Leu Pro Val Cys
                85                  90                  95

Gln Ala His Gly Leu Thr Pro Glu Gln Val Val Ala Ile Ala Ser Asn
            100                 105                 110

Ile Gly Gly Lys Gln Ala Leu Glu Thr Val Gln Arg Leu Leu Pro Val
        115                 120                 125

Cys Gln Ala His Gly Leu Thr Pro Glu Gln Val Val Ala Ile Ala Ser
    130                 135                 140

Asn Gly Gly Gly Lys Gln Ala Leu Glu Thr Val Gln Arg Leu Leu Pro
145                 150                 155                 160

Val Cys Gln Ala His Gly Leu Thr Pro Glu Gln Val Val Ala Ile Ala
            165                 170                 175

Ser Asn Gly Gly Gly Lys Gln Ala Leu Glu Thr Val Gln Arg Leu Leu
            180                 185                 190

Pro Val Cys Gln Ala His Gly Leu Thr Pro Glu Gln Val Val Ala Ile
        195                 200                 205

Ala Ser Asn Gly Gly Gly Lys Gln Ala Leu Glu Thr Val Gln Arg Leu
    210                 215                 220

Leu Pro Val Cys Gln Ala His Gly Gly Gly Ser Gly Pro Ala Ala Lys
225                 230                 235                 240

Arg Val Lys Leu Asp
                245
```

```
<210> SEQ ID NO 40
<211> LENGTH: 488
<212> TYPE: PRT
<213> ORGANISM: Artificial Sequence
<220> FEATURE:
<223> OTHER INFORMATION: synthetic peptide

<400> SEQUENCE: 40
```

```
Met Leu Thr Pro Glu Gln Val Val Ala Ile Ala Ser Asn His Gly Gly
1               5                   10                  15

Lys Gln Ala Leu Glu Thr Val Gln Arg Leu Leu Pro Val Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Cys Gln
    50                  55                  60

Ala His Gly Leu Thr Pro Glu Gln Val Val Ala Ile Ala Ser Asn Gly
65                  70                  75                  80

Gly Gly Lys Gln Ala Leu Glu Thr Val Gln Arg Leu Leu Pro Val Cys
                85                  90                  95

Gln Ala His Gly Leu Thr Pro Glu Gln Val Val Ala Ile Ala Ser Asn
            100                 105                 110

Ile Gly Gly Lys Gln Ala Leu Glu Thr Val Gln Arg Leu Leu Pro Val
        115                 120                 125

Cys Gln Ala His Gly Leu Thr Pro Glu Gln Val Val Ala Ile Ala Ser
    130                 135                 140

Asn Gly Gly Gly Lys Gln Ala Leu Glu Thr Val Gln Arg Leu Leu Pro
145                 150                 155                 160

Val Cys Gln Ala His Gly Leu Thr Pro Glu Gln Val Val Ala Ile Ala
            165                 170                 175
```

-continued

```
Ser Asn Gly Gly Gly Lys Gln Ala Leu Glu Thr Val Gln Arg Leu Leu
                180             185             190

Pro Val Cys Gln Ala His Gly Leu Thr Pro Glu Gln Val Val Ala Ile
            195             200             205

Ala Ser Asn Gly Gly Gly Lys Gln Ala Leu Glu Thr Val Gln Arg Leu
        210             215             220

Leu Pro Val Cys Gln Ala His Gly Gly Gly Ser Gly Asn Gly Glu Gly
225             230             235             240

Ser Gly Asn Gly Leu Thr Pro Glu Gln Val Val Ala Ile Ala Ser Asn
            245             250             255

Ile Gly Gly Lys Gln Ala Leu Glu Thr Val Gln Arg Leu Leu Pro Val
        260             265             270

Cys Gln Ala His Gly Leu Thr Pro Glu Gln Val Val Ala Ile Ala Ser
        275             280             285

Asn Ile Gly Gly Lys Gln Ala Leu Glu Thr Val Gln Arg Leu Leu Pro
    290             295             300

Val Cys Gln Ala His Gly Leu Thr Pro Glu Gln Val Val Ala Ile Ala
305             310             315             320

Ser Asn Ile Gly Gly Lys Gln Ala Leu Glu Thr Val Gln Arg Leu Leu
            325             330             335

Pro Val Cys Gln Ala His Gly Leu Thr Pro Glu Gln Val Val Ala Ile
            340             345             350

Ala Ser Asn Gly Gly Gly Lys Gln Ala Leu Glu Thr Val Gln Arg Leu
        355             360             365

Leu Pro Val Cys Gln Ala His Gly Leu Thr Pro Glu Gln Val Val Ala
    370             375             380

Ile Ala Ser Asn His Gly Gly Lys Gln Ala Leu Glu Thr Val Gln Arg
385             390             395             400

Leu Leu Pro Val Cys Gln Ala His Gly Leu Thr Pro Glu Gln Val Val
            405             410             415

Ala Ile Ala Ser His Asp Gly Gly Lys Gln Ala Leu Glu Thr Val Gln
            420             425             430

Arg Leu Leu Pro Val Cys Gln Ala His Gly Leu Thr Pro Glu Gln Val
        435             440             445

Val Ala Ile Ala Ser His Asp Gly Gly Lys Gln Ala Leu Glu Thr Val
    450             455             460

Gln Arg Leu Leu Pro Val Cys Gln Ala His Gly Gly Gly Ser Gly Pro
465             470             475             480

Ala Ala Lys Arg Val Lys Leu Asp
                485
```

```
<210> SEQ ID NO 41
<211> LENGTH: 141
<212> TYPE: PRT
<213> ORGANISM: Artificial Sequence
<220> FEATURE:
<223> OTHER INFORMATION: synthetic peptide

<400> SEQUENCE: 41

Met Gly Glu Gly Thr Cys Ala Val Cys Gly Asp Asn Ala Ala Cys Gln
1               5               10              15

His Tyr Gly Val Arg Thr Cys Glu Gly Cys Lys Gly Phe Phe Lys Arg
                20              25              30

Thr Val Gln Lys Asn Ala Lys Tyr Val Cys Leu Ala Asn Lys Asn Cys
        35              40              45
```

-continued

```
Pro Val Asp Lys Arg Arg Arg Asn Arg Cys Gln Tyr Cys Arg Phe Gln
    50              55                  60

Lys Cys Leu Ser Val Gly Met Val Lys Glu Val Val Arg Thr Asp Ser
65              70                  75                  80

Leu Lys Gly Arg Arg Gly Arg Leu Pro Ser Lys Pro Lys Gly Gly Ser
                85                  90                  95

Gly Asn Gly Ser Gly Ser Gln Asp Pro Ala Ala Ala Met Lys Gln Leu
            100                 105                 110

Glu Asp Lys Val Glu Glu Leu Leu Ser Lys Asn Tyr His Leu Glu Asn
        115                 120                 125

Glu Val Ala Arg Leu Thr Lys Leu Val Gly Gly Ser Gly
    130                 135                 140
```

```
<210> SEQ ID NO 42
<211> LENGTH: 141
<212> TYPE: PRT
<213> ORGANISM: Artificial Sequence
<220> FEATURE:
<223> OTHER INFORMATION: synthetic peptide

<400> SEQUENCE: 42

Met Gly Gly Ser Gly Ser Gln Asp Pro Ala Ala Ala Met Lys Gln Leu
1               5                   10                  15

Glu Asp Lys Val Glu Glu Leu Leu Ser Lys Asn Tyr His Leu Glu Asn
                20                  25                  30

Glu Val Ala Arg Leu Thr Lys Leu Val Gly Gly Ser Gly Asn Gly Ser
            35                  40                  45

Gly Gly Glu Gly Thr Cys Ala Val Cys Gly Asp Asn Ala Ala Cys Gln
    50              55                  60

His Tyr Gly Val Arg Thr Cys Glu Gly Cys Lys Gly Phe Phe Lys Arg
65              70                  75                  80

Thr Val Gln Lys Asn Ala Lys Tyr Val Cys Leu Ala Asn Lys Asn Cys
                85                  90                  95

Pro Val Asp Lys Arg Arg Arg Asn Arg Cys Gln Tyr Cys Arg Phe Gln
            100                 105                 110

Lys Cys Leu Ser Val Gly Met Val Lys Glu Val Val Arg Thr Asp Ser
        115                 120                 125

Leu Lys Gly Arg Arg Gly Arg Leu Pro Ser Lys Pro Lys
    130                 135                 140
```

```
<210> SEQ ID NO 43
<211> LENGTH: 334
<212> TYPE: PRT
<213> ORGANISM: Artificial Sequence
<220> FEATURE:
<223> OTHER INFORMATION: synthetic peptide

<400> SEQUENCE: 43

Met Gly Gly Ser Gly Gly Asp Lys Lys Ser Pro Thr Arg Pro Lys Arg
1               5                   10                  15

Gln Ala Lys Pro Ala Ala Asp Glu Gly Phe Trp Asp Cys Ser Val Cys
                20                  25                  30

Thr Phe Arg Asn Ser Ala Glu Ala Phe Lys Cys Ser Ile Cys Asp Val
            35                  40                  45

Arg Lys Gly Thr Ser Thr Arg Lys Pro Arg Ile Asn Ser Gln Leu Val
    50              55                  60

Ala Gln Gln Val Ala Gln Gln Tyr Ala Thr Pro Pro Pro Lys Lys
65              70                  75                  80
```

```
Glu Lys Lys Glu Lys Val Glu Lys Gln Asp Lys Glu Lys Pro Glu Lys
                85              90              95

Asp Lys Glu Ile Ser Pro Ser Val Thr Lys Lys Asn Thr Asn Lys Lys
            100             105             110

Thr Lys Pro Lys Ser Asp Ile Leu Lys Asp Pro Pro Ser Glu Ala Asn
        115             120             125

Ser Ile Gln Ser Ala Asn Ala Thr Thr Lys Thr Ser Glu Thr Asn His
    130             135             140

Thr Ser Arg Pro Arg Leu Lys Asn Val Asp Arg Ser Thr Ala Gln Gln
145             150             155             160

Leu Ala Val Thr Val Gly Asn Val Thr Val Ile Ile Thr Asp Phe Lys
                165             170             175

Glu Lys Thr Arg Ser Ser Ser Thr Ser Ser Ser Thr Val Thr Ser Ser
            180             185             190

Ala Gly Ser Glu Gln Gln Asn Gln Ser Ser Ser Gly Ser Glu Ser Thr
        195             200             205

Asp Lys Gly Ser Ser Arg Ser Ser Thr Pro Lys Gly Asp Met Ser Ala
    210             215             220

Val Asn Asp Glu Ser Phe Gly Gly Ser Gly Asn Gly Glu Gly Ser Gly
225             230             235             240

Asn Gly Gly Glu Gly Thr Cys Ala Val Cys Gly Asp Asn Ala Ala Cys
            245             250             255

Gln His Tyr Gly Val Arg Thr Cys Glu Gly Cys Lys Gly Phe Phe Lys
            260             265             270

Arg Thr Val Gln Lys Asn Ala Lys Tyr Val Cys Leu Ala Asn Lys Asn
            275             280             285

Cys Pro Val Asp Lys Arg Arg Arg Asn Arg Cys Gln Tyr Cys Arg Phe
    290             295             300

Gln Lys Cys Leu Ser Val Gly Met Val Lys Glu Val Val Arg Thr Asp
305             310             315             320

Ser Leu Lys Gly Arg Arg Gly Arg Leu Pro Ser Lys Pro Lys
            325             330
```

```
<210> SEQ ID NO 44
<211> LENGTH: 9
<212> TYPE: DNA
<213> ORGANISM: Artificial Sequence
<220> FEATURE:
<223> OTHER INFORMATION: synthetic polynucleotide

<400> SEQUENCE: 44 aaaggtcaa                                                          9

<210> SEQ ID NO 45
<211> LENGTH: 13
<212> TYPE: DNA
<213> ORGANISM: Artificial polynucleotide
<220> FEATURE:
<223> OTHER INFORMATION: synthetic polynucleotide
<220> FEATURE:
<221> NAME/KEY: misc_feature
<222> LOCATION: (7)..(7)
<223> OTHER INFORMATION: n is a gap of any nucleotide(s)

<400> SEQUENCE: 45
gatattngcc aat                                                     13

<210> SEQ ID NO 46
```

```
<211> LENGTH: 7
<212> TYPE: DNA
<213> ORGANISM: Artificial Sequence
<220> FEATURE:
<223> OTHER INFORMATION: synthetic polynucleotide

<400> SEQUENCE: 46 aaaggtc                                                                7

<210> SEQ ID NO 47
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 47
tgatatttac ctccaaatgc ca                                               22

<210> SEQ ID NO 48
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 48 gatatt                                                                 6

<210> SEQ ID NO 49
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 49 gccaat                                                                 6

<210> SEQ ID NO 50
<211> LENGTH: 92
<212> TYPE: PRT
<213> ORGANISM: Artificial Sequence
<220> FEATURE:
<223> OTHER INFORMATION: synthetic peptide

<400> SEQUENCE: 50

Ser Glu Gly Arg Cys Ala Val Cys Gly Asp Asn Ala Ser Cys Gln His
1               5                   10                  15

Tyr Gly Val Arg Thr Cys Glu Gly Cys Lys Gly Phe Phe Lys Arg Thr
            20                  25                  30

Val Gln Lys Asn Ala Lys Tyr Ile Cys Leu Ala Asn Lys Asp Cys Pro
        35                  40                  45

Val Asp Lys Arg Arg Arg Asn Arg Cys Gln Phe Cys Arg Phe Gln Lys
    50                  55                  60

Cys Leu Ala Val Gly Met Val Lys Glu Val Val Arg Thr Asp Ser Leu
65                  70                  75                  80

Lys Gly Arg Arg Gly Arg Leu Pro Ser Lys Pro Lys
                85                  90

<210> SEQ ID NO 51
<211> LENGTH: 93
<212> TYPE: PRT
<213> ORGANISM: Artificial Sequence
```

<220> FEATURE:
<223> OTHER INFORMATION: synthetic peptide

<400> SEQUENCE: 51

Ser Glu Gly Arg Cys Ala Val Cys Gly Asp Asn Ala Ser Cys Gln His
1               5                   10                  15

Tyr Gly Val Arg Thr Cys Glu Gly Cys Lys Gly Phe Phe Lys Arg Thr
            20                  25                  30

Val Gln Lys Asn Ala Lys Tyr Ile Cys Leu Ala Asn Lys Asp Cys Pro
        35                  40                  45

Val Asp Lys Arg Arg Arg Asn Arg Cys Gln Phe Cys Arg Phe Gln Lys
    50                  55                  60

Cys Leu Ala Val Gly Met Val Lys Glu Val Val Arg Thr Asp Ser Leu
65                  70                  75                  80

Lys Gly Arg Arg Gly Arg Leu Pro Ser Lys Pro Lys Gln
            85                  90

<210> SEQ ID NO 52
<211> LENGTH: 92
<212> TYPE: PRT
<213> ORGANISM: Artificial Sequence
<220> FEATURE:
<223> OTHER INFORMATION: synthetic peptide

<400> SEQUENCE: 52

Asn Glu Gly Leu Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
            20                  25                  30

Val Gln Lys Asn Ala Lys Tyr Val Cys Leu Ala Asn Lys Asn Cys Pro
        35                  40                  45

Val Asp Lys Arg Arg Arg Asn Arg Cys Gln Tyr Cys Arg Phe Gln Lys
    50                  55                  60

Cys Leu Ala Val Gly Met Val Lys Glu Val Val Arg Thr Asp Ser Leu
65                  70                  75                  80

Lys Gly Arg Arg Gly Arg Leu Pro Ser Lys Pro Lys
            85                  90

<210> SEQ ID NO 53
<211> LENGTH: 93
<212> TYPE: PRT
<213> ORGANISM: Artificial Sequence
<220> FEATURE:
<223> OTHER INFORMATION: synthetic peptide

<400> SEQUENCE: 53

Asn Glu Gly Leu Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
            20                  25                  30

Val Gln Lys Asn Ala Lys Tyr Val Cys Leu Ala Asn Lys Asn Cys Pro
        35                  40                  45

Val Asp Lys Arg Arg Arg Asn Arg Cys Gln Tyr Cys Arg Phe Gln Lys
    50                  55                  60

Cys Leu Ala Val Gly Met Val Lys Glu Val Val Arg Thr Asp Ser Leu
65                  70                  75                  80

Lys Gly Arg Arg Gly Arg Leu Pro Ser Lys Pro Lys Ser
            85                  90